(12) United States Patent
Goldstein et al.

(10) Patent No.: US 12,349,097 B2
(45) Date of Patent: Jul. 1, 2025

(54) INFORMATION PROCESSING USING A POPULATION OF DATA ACQUISITION DEVICES

(71) Applicant: ST FamTech, LLC

(72) Inventors: Steven W. Goldstein, Delray Beach, FL (US); John P Keady, Fairfax Station, VA (US)

(73) Assignee: ST FamTech, LLC, Delray Beach, FL (US)

( * ) Notice: Subject to any disclaimer, the term of this patent is extended or adjusted under 35 U.S.C. 154(b) by 365 days.

(21) Appl. No.: 17/962,083

(22) Filed: Oct. 7, 2022

(65) Prior Publication Data

US 2023/0087729 A1   Mar. 23, 2023

Related U.S. Application Data

(63) Continuation-in-part of application No. 17/235,130, filed on Apr. 20, 2021, now Pat. No. 11,589,329,
(Continued)

(51) Int. Cl.
*G16H 40/63* (2018.01)
*G16H 50/80* (2018.01)
(Continued)

(52) U.S. Cl.
CPC ............ *H04W 64/00* (2013.01); *G16H 40/63* (2018.01); *G16H 50/80* (2018.01);
(Continued)

(58) Field of Classification Search
CPC .............................. G16H 50/80; G16H 40/63
See application file for complete search history.

(56) References Cited

U.S. PATENT DOCUMENTS 3,876,843 A   4/1975 Moen
4,054,749 A   10/1977 Suzuki et al.
(Continued)

FOREIGN PATENT DOCUMENTS

EP   0495653 A1   7/1992
EP   1385324      1/2004
(Continued)

OTHER PUBLICATIONS

Olwal, A. and Feiner S. Interaction Techniques Using Prosodic Features of Speech and Audio Localization. Proceedings of IUI 2005 (International Conference on Intelligent User Interfaces), San Diego, CA, Jan. 9-12, 2005, p. 284-286.
(Continued)

*Primary Examiner* — Myron Wyche
(74) *Attorney, Agent, or Firm* — Akerman LLP; Peter A. Chiabotti; David A. Fernandez-Fidalgo

(57) ABSTRACT

Distributed wearable and non-wearable devices, controllers and methods for processing information from a plurality of devices are provided. A distributed system includes a plurality of devices distributed in an environment. Each device has at least a communication capability for interchanging information with others of the devices and/or with a communication system. Each of at least some of the devices has one or more sensors for acquiring sensor data related to the environment proximate to the device. At least one of the communication system or one or more of the devices is configured as a controller configured to: select a subset of devices from among the plurality of devices, receive information based on the acquired sensor data of the selected subset, and combine the received information from the selected subset to determine a characteristic of the environment proximate to one or more of the devices.

14 Claims, 11 Drawing Sheets

Related U.S. Application Data which is a continuation of application No. 16/736,820, filed on Jan. 8, 2020, now Pat. No. 10,986,604, which is a continuation of application No. 16/055,488, filed on Aug. 6, 2018, now Pat. No. 10,602,474, which is a continuation of application No. 13/976,636, filed as application No. PCT/US2011/068103 on Dec. 30, 2011, now Pat. No. 10,045,321.

(60) Provisional application No. 61/431,507, filed on Jan. 11, 2011, provisional application No. 61/428,369, filed on Dec. 30, 2010.

(51) Int. Cl.
*H04W 64/00* (2009.01)
*G06F 11/30* (2006.01)
*H04M 1/72403* (2021.01)

(52) U.S. Cl.
CPC ...... *G06F 11/3013* (2013.01); *G06F 11/3058* (2013.01); *H04M 1/72403* (2021.01); *H04M 2250/12* (2013.01)

(56) References Cited

U.S. PATENT DOCUMENTS

| | | |
|---|---|---|
| 4,088,849 A | 5/1978 | Usami et al. |
| 4,455,677 A | 6/1984 | Fox |
| 4,827,458 A | 5/1989 | D'Alayer de Costemore D'Arc |
| 4,891,841 A | 1/1990 | Bohn |
| 4,947,432 A | 8/1990 | Topholm |
| 4,947,440 A | 8/1990 | Bateman et al. |
| 5,027,410 A | 6/1991 | Williamson et al. |
| 5,182,774 A | 1/1993 | Bourk |
| 5,202,927 A | 4/1993 | Topholm |
| 5,208,867 A | 5/1993 | Stites, III |
| 5,251,263 A | 10/1993 | Andrea |
| 5,267,321 A | 11/1993 | Langberg |
| 5,276,740 A | 1/1994 | Inanaga et al. |
| 5,317,273 A | 5/1994 | Hanson |
| 5,327,506 A | 7/1994 | Stites |
| 5,524,056 A | 6/1996 | Killion et al. |
| 5,550,923 A | 8/1996 | Hotvet |
| 5,577,511 A | 11/1996 | Killion |
| 5,606,621 A | 2/1997 | Reiter et al. |
| 5,636,351 A | 6/1997 | Lee |
| 5,647,011 A | 7/1997 | Garvis |
| 5,740,262 A | 4/1998 | Yoshida et al. |
| 5,748,754 A | 5/1998 | Maag et al. |
| 5,826,064 A | 10/1998 | Loring et al. |
| 5,862,065 A | 1/1999 | Muthusamy |
| 5,903,868 A | 5/1999 | Yuen et al. |
| 5,923,624 A | 7/1999 | Groeger |
| 5,930,751 A | 7/1999 | Cohrs et al. |
| 5,933,510 A | 8/1999 | Bryant |
| 5,946,050 A | 8/1999 | Wolff |
| 6,005,525 A | 12/1999 | Kivela |
| 6,021,207 A | 2/2000 | Puthuff et al. |
| 6,021,325 A | 2/2000 | Hall |
| 6,028,514 A | 2/2000 | Lemelson |
| 6,048,320 A | 4/2000 | Brainard, II |
| 6,056,698 A | 5/2000 | Iseberg |
| 6,118,877 A | 9/2000 | Lindemann |
| 6,163,338 A | 12/2000 | Johnson et al. |
| 6,163,508 A | 12/2000 | Kim et al. |
| 6,226,389 B1 | 5/2001 | Lemelson et al. |
| 6,298,323 B1 | 10/2001 | Kaemmerer |
| 6,359,993 B2 | 3/2002 | Brimhall |
| 6,400,652 B1 | 6/2002 | Goldberg et al. |
| 6,408,272 B1 | 6/2002 | White |
| 6,415,034 B1 | 7/2002 | Hietanen |
| 6,567,524 B1 | 5/2003 | Svean et al. |
| 6,606,598 B1 | 8/2003 | Holthouse |
| 6,639,987 B2 | 10/2003 | McIntosh |
| 6,647,368 B2 | 11/2003 | Nemirovski |
| RE38,351 E | 12/2003 | Iseberg et al. |
| 6,661,901 B1 | 12/2003 | Svean et al. |
| 6,671,379 B2 | 12/2003 | Nemirovski |
| 6,687,377 B2 | 2/2004 | Voix et al. |
| 6,728,385 B2 | 4/2004 | Kvaloy et al. |
| 6,748,238 B1 | 6/2004 | Lau |
| 6,754,359 B1 | 6/2004 | Svean et al. |
| 6,760,754 B1 | 7/2004 | Isaacs et al. |
| 6,782,106 B1 | 8/2004 | Kong et al. |
| 6,738,482 B1 | 9/2004 | Jaber |
| 6,804,638 B2 | 10/2004 | Fiedler |
| 6,804,643 B1 | 10/2004 | Kiss |
| 6,826,286 B1 | 11/2004 | Arndt et al. |
| 7,003,099 B1 | 2/2006 | Zhang |
| 7,039,195 B1 | 5/2006 | Svean |
| 7,039,585 B2 | 5/2006 | Wilmot |
| 7,050,592 B1 | 5/2006 | Iseberg |
| 7,072,482 B2 | 7/2006 | Van Doorn et al. |
| 7,107,109 B1 | 9/2006 | Nathan et al. |
| 7,158,643 B2 | 1/2007 | Lavoie et al. |
| 7,158,933 B2 | 1/2007 | Balan |
| 7,177,433 B2 | 2/2007 | Sibbald |
| 7,209,569 B2 | 4/2007 | Boesen |
| 7,280,849 B1 | 10/2007 | Bailey |
| 7,430,299 B2 | 9/2008 | Armstrong et al. |
| 7,433,714 B2 | 10/2008 | Howard et al. |
| 7,444,353 B1 | 10/2008 | Chen |
| 7,450,730 B2 | 11/2008 | Bertg et al. |
| 7,464,029 B2 | 12/2008 | Visser |
| 7,477,756 B2 | 1/2009 | Wickstrom et al. |
| 7,512,245 B2 | 3/2009 | Rasmussen |
| 7,529,379 B2 | 5/2009 | Zurek |
| 7,562,020 B2 | 6/2009 | Le et al. |
| 7,574,917 B2 | 8/2009 | Von Dach |
| 7,715,577 B2 | 5/2010 | Allen et al. |
| 7,729,912 B1 | 6/2010 | Bacchiani et al. |
| 7,756,285 B2 | 7/2010 | Sjursen et al. |
| 7,774,202 B2 | 8/2010 | Spengler et al. |
| 7,778,434 B2 | 8/2010 | Juneau et al. |
| 7,801,726 B2 | 9/2010 | Ariu |
| 7,844,248 B2 | 11/2010 | Sotack |
| 7,853,031 B2 | 12/2010 | Hamacher |
| 7,861,008 B2 | 12/2010 | Batson et al. |
| 7,903,825 B1 | 3/2011 | Melanson |
| 7,903,826 B2 | 3/2011 | Boersma |
| 7,920,557 B2 | 4/2011 | Moote |
| 7,936,885 B2 | 5/2011 | Frank |
| 7,983,907 B2 | 7/2011 | Visser |
| 8,014,553 B2 | 9/2011 | Radivojevic et al. |
| 8,018,337 B2 | 9/2011 | Jones |
| 8,045,840 B2 | 10/2011 | Murata |
| 8,081,780 B2 | 12/2011 | Goldstein et al. |
| 8,086,093 B2 | 12/2011 | Stuckman |
| 8,111,839 B2 | 2/2012 | Goldstein et al. |
| 8,140,325 B2 | 3/2012 | Kanevsky |
| 8,150,044 B2 | 4/2012 | Goldstein |
| 8,160,261 B2 | 4/2012 | Schulein |
| 8,160,273 B2 | 4/2012 | Visser |
| 8,162,846 B2 | 4/2012 | Epley |
| 8,180,078 B2 | 5/2012 | Zellner |
| 8,189,803 B2 | 5/2012 | Bergeron |
| 8,208,642 B2 | 6/2012 | Edwards |
| 8,209,181 B2 | 6/2012 | Heckerman et al. |
| 8,218,784 B2 | 7/2012 | Schulein |
| 8,254,591 B2 | 8/2012 | Goldstein |
| 8,270,629 B2 | 9/2012 | Bothra |
| 8,315,400 B2 | 11/2012 | Goldstein et al. |
| 8,401,198 B2 | 3/2013 | Oh et al. |
| 8,401,200 B2 | 3/2013 | Tiscareno |
| 8,477,955 B2 | 7/2013 | Engle |
| 8,488,799 B2 | 7/2013 | Goldstein et al. |
| 8,493,204 B2 | 7/2013 | Wong et al. |
| 8,522,916 B2 | 9/2013 | Keady |
| 8,577,062 B2 | 11/2013 | Goldstein |
| 8,594,341 B2 | 11/2013 | Rothschild |
| 8,611,560 B2 | 12/2013 | Goldstein |
| 8,625,818 B2 | 1/2014 | Stultz |
| 8,718,305 B2 | 5/2014 | Usher |

(56) References Cited

U.S. PATENT DOCUMENTS

| | | |
|---|---|---|
| 8,750,295 B2 | 6/2014 | Liron |
| 8,774,433 B2 | 7/2014 | Goldstein |
| 8,798,278 B2 | 8/2014 | Isabelle |
| 8,851,372 B2 | 10/2014 | Zhou |
| 8,855,343 B2 | 10/2014 | Usher |
| 8,917,894 B2 | 12/2014 | Goldstein |
| 8,983,081 B2 | 3/2015 | Bayley |
| 9,013,351 B2 | 4/2015 | Park |
| 9,037,458 B2 | 5/2015 | Park et al. |
| 9,053,697 B2 | 6/2015 | Park |
| 9,112,701 B2 | 8/2015 | Sano |
| 9,113,240 B2 | 8/2015 | Ramakrishman |
| 9,123,343 B2 | 9/2015 | Kurki-Suonio |
| 9,124,982 B2 | 9/2015 | Goldstein et al. |
| 9,135,797 B2 | 9/2015 | Couper et al. |
| 9,191,740 B2 | 11/2015 | McIntosh |
| 9,196,247 B2 | 11/2015 | Harada |
| 9,270,244 B2 | 2/2016 | Usher et al. |
| 9,491,542 B2 | 11/2016 | Usher |
| 9,609,424 B2 | 3/2017 | Goldstein |
| 9,628,896 B2 | 4/2017 | Ichimura |
| 9,684,778 B2 | 6/2017 | Tharappel |
| 10,142,332 B2 | 11/2018 | Ravindran |
| 10,365,883 B2 | 7/2019 | Goldstein et al. |
| 10,709,339 B1 | 7/2020 | Lusted |
| 10,848,827 B2 | 11/2020 | Sengupta et al. |
| 10,966,015 B2 | 3/2021 | Usher |
| 10,970,375 B2 | 4/2021 | Manikantan |
| 10,979,836 B2 | 4/2021 | Usher et al. |
| 11,039,259 B2 | 6/2021 | Goldstein et al. |
| 11,057,701 B2 | 7/2021 | Goldstein et al. |
| 11,217,237 B2 | 1/2022 | Usher et al. |
| 11,244,666 B2 | 2/2022 | Goldstein et al. |
| 11,277,682 B2 | 3/2022 | Usher |
| 11,393,486 B1 | 7/2022 | Woodruff et al. |
| 11,610,587 B2 | 3/2023 | Goldstein et al. |
| 11,659,315 B2 | 5/2023 | Perez et al. |
| 11,665,493 B2 | 5/2023 | Usher et al. |
| 11,710,473 B2 | 7/2023 | Goldstein et al. |
| 11,750,965 B2 | 9/2023 | Usher et al. |
| 2001/0046304 A1 | 11/2001 | Rast |
| 2002/0018798 A1 | 2/2002 | Sewing et al. |
| 2002/0026311 A1 | 2/2002 | Okitsu |
| 2002/0076057 A1 | 6/2002 | Voix |
| 2002/0098878 A1 | 7/2002 | Mooney |
| 2002/0106091 A1 | 8/2002 | Furst et al. |
| 2002/0111798 A1 | 8/2002 | Huang |
| 2002/0116541 A1 | 8/2002 | Parker et al. |
| 2002/0118798 A1 | 8/2002 | Langhart et al. |
| 2002/0165719 A1 | 11/2002 | Wang |
| 2002/0193130 A1 | 12/2002 | Yang |
| 2003/0032447 A1 | 2/2003 | Bulthuis |
| 2003/0035551 A1 | 2/2003 | Ligh |
| 2003/0130016 A1 | 7/2003 | Matsuura |
| 2003/0138118 A1 | 7/2003 | Stahl |
| 2003/0152359 A1 | 8/2003 | Kim |
| 2003/0161097 A1 | 8/2003 | Le et al. |
| 2003/0165246 A1 | 9/2003 | Kvaloy et al. |
| 2003/0165319 A1 | 9/2003 | Barber |
| 2003/0198359 A1 | 10/2003 | Killion |
| 2004/0042103 A1 | 3/2004 | Mayer |
| 2004/0086138 A1 | 5/2004 | Kuth |
| 2004/0109668 A1 | 6/2004 | Stuckman |
| 2004/0109579 A1 | 7/2004 | Izuchi |
| 2004/0125965 A1 | 7/2004 | Alberth, Jr. et al. |
| 2004/0133421 A1 | 7/2004 | Burnett |
| 2004/0179694 A1 | 9/2004 | Alley |
| 2004/0190737 A1 | 9/2004 | Kuhnel et al. |
| 2004/0196992 A1 | 10/2004 | Ryan |
| 2004/0202340 A1 | 10/2004 | Armstrong |
| 2004/0203351 A1 | 10/2004 | Shearer et al. |
| 2004/0264938 A1 | 12/2004 | Felder |
| 2005/0028212 A1 | 2/2005 | Laronne |
| 2005/0049854 A1 | 3/2005 | Reding et al. |
| 2005/0058313 A1 | 3/2005 | Victorian |
| 2005/0068171 A1 | 3/2005 | Kelliher |
| 2005/0071158 A1 | 3/2005 | Byford |
| 2005/0077102 A1 | 4/2005 | Banter et al. |
| 2005/0078838 A1 | 4/2005 | Simon |
| 2005/0096899 A1 | 5/2005 | Padhi et al. |
| 2005/0102142 A1 | 5/2005 | Soufflet |
| 2005/0123146 A1 | 6/2005 | Voix et al. |
| 2005/0157891 A1 | 7/2005 | Johansen |
| 2005/0182620 A1 | 8/2005 | Kabi et al. |
| 2005/0207605 A1 | 9/2005 | Dehe |
| 2005/0227674 A1 | 10/2005 | Kopra |
| 2005/0281422 A1 | 12/2005 | Armstrong |
| 2005/0281423 A1 | 12/2005 | Armstrong |
| 2005/0288057 A1 | 12/2005 | Lai et al. |
| 2006/0018496 A1 | 1/2006 | Niederdrank et al. |
| 2006/0067551 A1 | 3/2006 | Cartwright et al. |
| 2006/0083387 A1 | 4/2006 | Emoto |
| 2006/0083390 A1 | 4/2006 | Kaderavek |
| 2006/0083395 A1 | 4/2006 | Allen et al. |
| 2006/0092043 A1 | 5/2006 | Lagassey |
| 2006/0116175 A1 | 6/2006 | Chu |
| 2006/0120545 A1 | 6/2006 | Rasmussen |
| 2006/0140425 A1 | 6/2006 | Berg |
| 2006/0153394 A1 | 7/2006 | Beasley |
| 2006/0167687 A1 | 7/2006 | Kates |
| 2006/0173563 A1 | 8/2006 | Borovitski |
| 2006/0182287 A1 | 8/2006 | Schulein |
| 2006/0182295 A1 | 8/2006 | Dijkstra et al. |
| 2006/0188075 A1 | 8/2006 | Peterson |
| 2006/0188105 A1 | 8/2006 | Baskerville |
| 2006/0195322 A1 | 8/2006 | Broussard et al. |
| 2006/0204014 A1 | 9/2006 | Isenberg et al. |
| 2006/0223547 A1 | 10/2006 | Chin et al. |
| 2006/0241948 A1 | 10/2006 | Abrash et al. |
| 2006/0262944 A1 | 11/2006 | Rasmussen et al. |
| 2006/0264176 A1 | 11/2006 | Hong |
| 2006/0287014 A1 | 12/2006 | Matsuura |
| 2007/0003090 A1 | 1/2007 | Anderson |
| 2007/0021148 A1 | 1/2007 | Mahini |
| 2007/0021958 A1 | 1/2007 | Visser et al. |
| 2007/0027676 A1 | 2/2007 | Chambers et al. |
| 2007/0036377 A1 | 2/2007 | Stirnemann |
| 2007/0041589 A1 | 2/2007 | Patel et al. |
| 2007/0043563 A1 | 2/2007 | Comerford et al. |
| 2007/0014423 A1 | 4/2007 | Darbut |
| 2007/0086600 A1 | 4/2007 | Boesen |
| 2007/0092087 A1 | 4/2007 | Bothra |
| 2007/0100637 A1 | 5/2007 | McCune |
| 2007/0127660 A1 | 6/2007 | Roberts et al. |
| 2007/0143820 A1 | 6/2007 | Pawlowski |
| 2007/0160243 A1 | 7/2007 | Dijkstra |
| 2007/0172087 A1 | 7/2007 | Olsen |
| 2007/0177743 A1 | 8/2007 | Mertens |
| 2007/0189544 A1 | 8/2007 | Rosenberg |
| 2007/0201705 A1 | 8/2007 | Dorogusker et al. |
| 2007/0223717 A1 | 9/2007 | Boersma |
| 2007/0253569 A1 | 11/2007 | Bose |
| 2007/0255435 A1 | 11/2007 | Cohen |
| 2007/0281744 A1 | 12/2007 | Andreasson |
| 2007/0291953 A1 | 12/2007 | Ngia et al. |
| 2008/0037801 A1 | 2/2008 | Alves et al. |
| 2008/0063228 A1 | 3/2008 | Mejia |
| 2008/0079571 A1 | 4/2008 | Samadani |
| 2008/0089530 A1 | 4/2008 | Bostick et al. |
| 2008/0091421 A1 | 4/2008 | Gustavsson |
| 2008/0107297 A1 | 5/2008 | Fischer et al. |
| 2008/0129520 A1 | 6/2008 | Lee |
| 2008/0130908 A1 | 6/2008 | Cohen |
| 2008/0137873 A1 | 6/2008 | Goldstein |
| 2008/0145032 A1 | 6/2008 | Lindroos |
| 2008/0159547 A1 | 7/2008 | Schuler |
| 2008/0162133 A1 | 7/2008 | Couper et al. |
| 2008/0165988 A1 | 7/2008 | Terlizzi et al. |
| 2008/0175411 A1 | 7/2008 | Greve |
| 2008/0181419 A1 | 7/2008 | Goldstein et al. |
| 2008/0221880 A1 | 9/2008 | Cerra et al. |
| 2008/0240458 A1 | 10/2008 | Goldstein et al. |
| 2009/0010456 A1 | 1/2009 | Goldstein et al. |
| 2009/0024234 A1 | 1/2009 | Archibald |

(56) References Cited

U.S. PATENT DOCUMENTS

| | | |
|---|---|---|
| 2009/0076821 A1 | 3/2009 | Brenner |
| 2009/0085873 A1 | 4/2009 | Betts |
| 2009/0122996 A1 | 5/2009 | Klein |
| 2009/0286515 A1 | 5/2009 | Othmer |
| 2010/0061564 A1 | 3/2010 | Clemow et al. |
| 2010/0119077 A1 | 5/2010 | Platz |
| 2010/0296668 A1 | 11/2010 | Lee et al. |
| 2010/0316033 A1 | 12/2010 | Atwal |
| 2010/0328224 A1 | 12/2010 | Kerr et al. |
| 2011/0026724 A1 | 2/2011 | Doclo |
| 2011/0055256 A1 | 3/2011 | Phillips |
| 2011/0096939 A1 | 4/2011 | Ichimura |
| 2011/0116643 A1 | 5/2011 | Tiscareno |
| 2011/0187640 A1 | 8/2011 | Jacobsen et al. |
| 2011/0264447 A1 | 10/2011 | Visser et al. |
| 2011/0293103 A1 | 12/2011 | Park et al. |
| 2011/0299695 A1 | 12/2011 | Nicholson |
| 2012/0170412 A1 | 7/2012 | Calhoun |
| 2013/0219345 A1 | 8/2013 | Saukko et al. |
| 2014/0023203 A1 | 1/2014 | Rotschild |
| 2014/0089672 A1 | 3/2014 | Luna |
| 2014/0122092 A1 | 5/2014 | Goldstein |
| 2014/0126748 A1 | 5/2014 | Usher et al. |
| 2014/0163976 A1 | 6/2014 | Park |
| 2014/0166122 A1 | 6/2014 | Goldstein et al. |
| 2014/0270200 A1 | 9/2014 | Usher et al. |
| 2015/0170645 A1 | 6/2015 | Di et al. |
| 2015/0195641 A1 | 7/2015 | Di et al. |
| 2015/0215701 A1 | 7/2015 | Usher |
| 2016/0019024 A1 | 1/2016 | Suzuki et al. |
| 2016/0104452 A1 | 4/2016 | Guan et al. |
| 2016/0249128 A1 | 8/2016 | Goldstein |
| 2018/0115818 A1 | 4/2018 | Asada et al. |
| 2018/0160211 A1 | 6/2018 | Kirsch et al. |
| 2019/0038224 A1 | 2/2019 | Zhang |
| 2020/0379717 A1 | 12/2020 | Mazur et al. |
| 2020/0380945 A1 | 12/2020 | Woodruff et al. |

FOREIGN PATENT DOCUMENTS

| | | |
|---|---|---|
| EP | 1385324 A1 | 1/2004 |
| EP | 1401240 | 3/2004 |
| EP | 1519625 A2 | 3/2005 |
| EP | 1640972 | 3/2006 |
| EP | 1640972 A1 | 3/2006 |
| JP | H0877468 | 3/1996 |
| JP | H10162283 | 6/1998 |
| JP | 2002-204500 A | 7/2002 |
| JP | 3353701 | 12/2002 |
| WO | WO9326085 | 12/1993 |
| WO | 01/89083 A1 | 11/2001 |
| WO | 2004114722 | 12/2004 |
| WO | 2006/036262 A2 | 4/2006 |
| WO | 2006037156 A1 | 4/2006 |
| WO | 2006054698 | 5/2006 |
| WO | 2006/097099 A1 | 9/2006 |
| WO | 2007/073818 A1 | 7/2007 |
| WO | 2007092660 | 8/2007 |
| WO | 2008050583 | 5/2008 |
| WO | 2008/067454 A2 | 6/2008 |
| WO | 2009/023633 A1 | 2/2009 |
| WO | 2009023784 | 2/2009 |
| WO | 2012097150 | 7/2012 |

OTHER PUBLICATIONS

Bernard Widrow, John R. Glover Jr., John M. McCool, John Kaunitz, Charles S. Williams, Robert H. Hearn, James R. Zeidler, Eugene Dong Jr, and Robert C. Goodlin, Adaptive Noise Cancelling: Principles and Applications, Proceedings of the IEEE, vol. 63, No. 12, Dec. 1975.

Mauro Dentino, John M. McCool, and Bernard Widrow, Adaptive Filtering in the Frequency Domain, Proceedings of the IEEE, vol. 66, No. 12, Dec. 1978.

*Samsung Electronics Co., Ltd., and Samsung Electronics, America, Inc., v. Staton Techiya, LLC*, IPR2022-00282, Dec. 21, 2021.

*Samsung Electronics Co., Ltd., and Samsung Electronics, America, Inc., v. Staton Techiya, LLC*, IPR2022-00242, Dec. 23, 2021.

*Samsung Electronics Co., Ltd., and Samsung Electronics, America, Inc., v. Staton Techiya, LLC*, IPR2022-00243, Dec. 23, 2021.

*Samsung Electronics Co., Ltd., and Samsung Electronics, America, Inc., v. Staton Techiya, LLC*, IPR2022-00234, Dec. 21, 2021.

*Samsung Electronics Co., Ltd., and Samsung Electronics, America, Inc., v. Staton Techiya, LLC*, IPR2022-00253, Jan. 18, 2022.

*Samsung Electronics Co., Ltd., and Samsung Electronics, America, Inc., v. Staton Techiya, LLC*, IPR2022-00324, Jan. 13, 2022.

*Samsung Electronics Co., Ltd., and Samsung Electronics, America, Inc., v. Staton Techiya, LLC*, IPR2022-00281, Jan. 18, 2022.

*Samsung Electronics Co., Ltd., and Samsung Electronics, America, Inc., v. Staton Techiya, LLC*, IPR2022-00302, Jan. 13, 2022.

*Samsung Electronics Co., Ltd., and Samsung Electronics, America, Inc., v. Staton Techiya, LLC*, IPR2022-00369, Feb. 18, 2022.

*Samsung Electronics Co., Ltd., and Samsung Electronics, America, Inc., v. Staton Techiya, LLC*, IPR2022-00388, Feb. 18, 2022.

*Samsung Electronics Co., Ltd., and Samsung Electronics, America, Inc., v. Staton Techiya, LLC*, IPR2022-00410, Feb. 18, 2022.

*Samsung Electronics Co., Ltd., and Samsung Electronics, America, Inc., v. Staton Techiya, LLC*, IPR2022-01078, Jun. 9, 2022.

*Samsung Electronics Co., Ltd., and Samsung Electronics, America, Inc., v. Staton Techiya, LLC*, IPR2022-01099, Jun. 9, 2022.

*Samsung Electronics Co., Ltd., and Samsung Electronics, America, Inc., v. Staton Techiya, LLC*, IPR2022-01106, Jun. 9, 2022.

*Samsung Electronics Co., Ltd., and Samsung Electronics, America, Inc., v. Staton Techiya, LLC*, IPR2022-01098, Jun. 9, 2022.

'400 Patent Family Tree, Exhibit—1009, Filed on Dec. 10, 2021, challenging U.S. Pat. No. 8,315,400.

Nov. 3, 2022 [16] Notice of Deposition of David Kleinschmidt, Exhibit—16, Filed on Nov. 3, 2022, challenging U.S. Pat. No. 8,315,400.

Aarts, Exhibit—1015, Filed on Jan. 14, 2022, challenging U.S. Pat. No. 10,979,836.

Adaptive Filtering (Dentino), Exhibit—1012, Filed on Dec. 10, 2021, challenging U.S. Pat. No. 8,315,400.

Adaptive Filtering Algorithims (Diniz), Exhibit—1013, Filed on 12/10/2021, challenging U.S. Pat. No. 8,315,400.

Adaptive Noise Cancelling (Widrow), Exhibit—1011, Filed on Dec. 10, 2021, challenging U.S. Pat. No. 8,315,400.

AirPods (1st generation)—Technical Specifications, Exhibit—2009, Filed on Sep. 13, 2022, challenging U.S. Pat. No. 8,111,839.

Amended Complaint, *Techiya v. Samsung, E.D. Tex.*, Exhibit—1014, Filed on Jan. 14, 2022, challenging U.S. Pat. No. 10,979,836.

Amended Complaint, *Techiya v. Samsung, E.D. Tex.*, Exhibit—1014, Filed on Dec. 21, 2021, challenging U.S. Pat. No. 9,609,424.

Amended Complaint, *Techiya v. Samsung, E.D. Tex.*, Exhibit—1017, Filed on Jan. 14, 2022, challenging U.S. Pat. No. 10,966,015.

Amended Complaint, *Techiya v. Samsung, E.D. Tex.*, Exhibit—1017, Filed on Dec. 30, 2021, challenging U.S. Pat. No. 10,405,082.

Amended Docket Control Order, DN 156 from E.D. Tex. 21-cv-00413, Exhibit—1029, Filed on Nov. 15, 2022, challenging U.S. Pat. No. 11,217,237.

Amended Docket Control Order, DN 156 from E.D. Tex., Exhibit—1023, Filed on Nov. 10, 2022, challenging U.S. Pat. No. 11,244,666.

Amended Docket Control Order, DN 156 from E.D. Tex., Exhibit—1026, Filed on Nov. 10, 2022, challenging U.S. Pat. No. 11,057,701.

Amended Docket Control Order, DN 156 from E.D. Tex., Exhibit—1032, Filed on Nov. 10, 2022, challenging U.S. Pat. No. 11,039,259.

Amended Notice of Deposition of Les E. Atlas, Ph.D., Exhibit—15, Filed on Mar. 14, 2023, challenging U.S. Pat. No. 11,039,259.

Amendment in U.S. Appl. No. 11/616,973, dated Apr. 13, 2015, Exhibit—2009, Filed on Oct. 11, 2022, challenging U.S. Pat. No. 11,039,259.

Anderson Declaration ISO MSJ of No Infringement of '259 Patent, Exhibit—2019, Filed on Aug. 14, 2023, challenging U.S. Pat. No. 11,039,259.

(56) References Cited

OTHER PUBLICATIONS

Anderson Non-Infringement Report (excerpt, redacted), Exhibit—2020, Filed on Aug. 14, 2023, challenging U.S. Pat. No. 11,039,259.
Anderson Rebuttal Report (Redacted, Excerpt), Exhibit—2017, Filed on Apr. 10, 2023, challenging U.S. Pat. No. 11,039,259.
Android Central, The History of True Wireless Earbuds, Exhibit—2009, Filed on Oct. 17, 2022, challenging U.S. Pat. No. 8,254,591.
Android Central, The History of True Wireless Earbuds, Exhibit—2011, Filed on Sep. 13, 2022, challenging U.S. Pat. No. 8,111,839.
C.V. of Richard Stern, Ph.D., Exhibit—1003, Filed on Jan. 4, 2022, challenging U.S. Pat. No. 10,966,015.
C.V. of Richard Stern, Ph.D., Exhibit—1003, Filed on Dec. 10, 2021, challenging U.S. Pat. No. 8,315,400.
CDC, What Noises Cause Hearing Loss?, Exhibit—2009, Filed on Sep. 13, 2022, challenging U.S. Pat. No. 8,111,839.
Christopher J. Struck CV, Exhibit—2002, Filed on Apr. 13, 2022, challenging U.S. Pat. No. 9,609,424.
Claim Construction Order, Exhibit—2008, Filed on Feb. 22, 2023, challenging U.S. Pat. No. 9,491,542.
Claim Construction Order, Exhibit—2008, Filed on Apr. 18, 2023, challenging U.S. Pat. No. 9,270,244.
Claim Construction Order, Exhibit—2013, Filed on Apr. 10, 2023, challenging U.S. Pat. No. 11,039,259.
Complaint, DN 1 from E.D. Tex. 21-cv-00413, Exhibit—1022, Filed on Nov. 10, 2022, challenging U.S. Pat. No. 11,244,666.
Complaint, DN 1 from E.D. Tex. 21-cv-00413, Exhibit—1025, Filed on Nov. 10, 2022, challenging U.S. Pat. No. 11,057,701.
Complaint, DN 1 from E.D. Tex. 21-cv-00413, Exhibit—1028, Filed on Nov. 15, 2022, challenging U.S. Pat. No. 11,217,237.
Complaint, DN 1 from E.D. Tex. 21-cv-00413, Exhibit—1031, Filed on Nov. 10, 2022, challenging U.S. Pat. No. 11,039,259.
Complaint, E.D. Tex. 22-53, Exhibit—1020, Filed on Jun. 14, 2022, challenging U.S. Pat. No. 10,405,082.
Complaint, E.D. Tex. 22-53, Exhibit—1020, Filed on Jun. 14, 2022, challenging U.S. Pat. No. 10,966,015.
Complaint, E.D. Tex. 22-53, Exhibit—1021, Filed on Jun. 14, 2022, challenging U.S. Pat. No. 10,979,836.
Complaint, E.D. Tex., 22-cv-53, Exhibit—1024, Filed on May 10, 2022, challenging U.S. Pat. No. 9,609,424.
Complaint, E.D. Tex., 22-cv-53, Exhibit—1032, Filed on May 11, 2022, challenging U.S. Pat. No. 8,254,591.
Complaint, Techiya v. Samsung, E.D. Tex., Exhibit—1008, Filed on Jan. 14, 2022, challenging U.S. Pat. No. 10,979,836.
*Complaint, Techiya v. Samsung, E.D. Tex.*, Exhibit—1008, Filed on Dec. 21, 2021, challenging U.S. Pat. No. 9,609,424.
Consolidation Order, E.D. Tex. 21-413 & 22-53, Exhibit—1021, Filed on Jun. 14, 2022, challenging U.S. Pat. No. 10,405,082.
Consolidation Order, E.D. Tex. 21-413 & 22-53, Exhibit—1021, Filed on Jun. 14, 2022, challenging U.S. Pat. No. 10,966,015.
Consolidation Order, E.D. Tex. 21-413 & 22-53, Exhibit—1022, Filed on Jun. 14, 2022, challenging U.S. Pat. No. 10,979,836.
Consolidation Order, E.D. Tex., Exhibit—1025, Filed on May 10, 2022, challenging U.S. Pat. No. 9,609,424.
Consolidation Order, E.D. Tex., Exhibit—1033, Filed on May 11, 2022, challenging U.S. Pat. No. 8,254,591.
Corrected Declaration of Richard Stern, Ph.D., Exhibit—1002, Filed on Jan. 4, 2022, challenging U.S. Pat. No. 10,966,015.
Corrected Declaration of Richard Stern, Ph.D., Exhibit—1002, Filed on Dec. 10, 2021, challenging U.S. Pat. No. 8,315,400.
Corrected Petition for Inter Partes Review of U.S. Pat. No. 8,111,839, Exhibit—11, Filed on Feb. 3, 2022, challenging U.S. Pat. No. 8,111,839.
Corrected Petition for Inter Partes Review of U.S. Pat. No. 8,111,839, Exhibit—12, Filed on Feb. 3, 2022, challenging U.S. Pat. No. 8,111,839.
Corrected Petition for IPR of U.S. Pat. No. 8,315,400, Exhibit—4, Filed on Dec. 10, 2021, challenging U.S. Pat. No. 8,315,400.
Curriculum Vitae of Christopher J. Struck, Exhibit—2002, Filed on Oct. 7, 2022, challenging U.S. Pat. No. 11,057,701.
Curriculum Vitae of Christopher J. Struck, Exhibit—2002, Filed on Oct. 7, 2022, challenging U.S. Pat. No. 11,217,237.
Curriculum Vitae of David Kleinschmidt, Exhibit—2002, Filed on Oct. 11, 2022, challenging U.S. Pat. No. 11,039,259.
Curriculum Vitae of David Kleinschmidt, Exhibit—2002, Filed on Oct. 7, 2022, challenging U.S. Pat. No. 11,244,666.
CV for Marshall Buck, Ph.D., Exhibit—2002, Filed on May 18, 2022, challenging U.S. Pat. No. 10,405,082.
CV of Chris Kyriakakis, Ph.D., Exhibit—1003, Filed on Dec. 21, 2021, challenging U.S. Pat. No. 9,609,424.
CV of Christopher J. Struck, Exhibit—2002, Filed on May 18, 2022, challenging U.S. Pat. No. 10,979,836.
CV of Daniel P. Anagnos, Exhibit—2002, Filed on Mar. 23, 2022, challenging U.S. Pat. No. 8,111,839.
CV of Daniel P. Anagnos; Exhibit—2002, Filed on Mar. 21, 2022, challenging U.S. Pat. No. 9,124,982.
CV of Dr. Chris Kyriakakis, Exhibit—1003, Filed on Jan. 14, 2022, challenging U.S. Pat. No. 10,979,836.
CV of Les E. Atlas, Ph.D., Exhibit—1003, Filed on Dec. 20, 2021, challenging U.S. Pat. No. 8,254,591.
CV of Les E. Atlas, Ph.D., Exhibit—1004, Filed on Dec. 13, 2021, challenging U.S. Pat. No. 8,111,839.
CV of Marshall Buck, Ph.D., Exhibit—2002, Filed on May 18, 2022, challenging U.S. Pat. No. 10,966,015.
CV of Nathaniel Polish, Ph.D., Exhibit—1003, Filed on Dec. 17, 2021, challenging U.S. Pat. No. 9,491,542.
CV of Nathaniel Polish, Ph.D., Exhibit—1003, Filed on Dec. 21, 2021, challenging U.S. Pat. No. 9,270,244.
CV of of Les E. Atlas, Ph.D.; Exhibit—1003, Filed on Dec. 13, 2021, challenging U.S. Pat. No. 9124982.
CV of Richard Stern, Ph.D., Exhibit—1003, Filed on Dec. 30, 2021, challenging U.S. Pat. No. 10,405,082.
Daniel P. Anagnos CV, Exhibit—2002, Filed on Apr. 13, 2022, challenging U.S. Pat. No. 8,254,591.
David Kleinschmidt CV, Exhibit—2002, Filed on Mar. 21, 2022, challenging U.S. Pat. No. 8,315,400.
David Kleinschmidt CV, Exhibit—2002, Filed on Apr. 18, 2022, challenging U.S. Pat. No. 9,491,542.
David Kleinschmidt CV, Exhibit—2002, Filed on Apr. 18, 2022, challenging U.S. Pat. No. 9,270,244.
Decision Denying Institution of Inter Partes Review 35 U.S.C. § 314, Exhibit—10, Filed on Jan. 3, 2023, challenging U.S. Pat. No. 11,244,666.
Decision Denying Institution of Inter Partes Review 35 U.S.C. § 314, Exhibit—11, Filed on Jan. 3, 2023, challenging U.S. Pat. No. 11,217,237.
Decision Granting Institution of Inter Partes Review 35 U.S.C. sec 314, Exhibit—10, Filed on Dec. 29, 2022, challenging U.S. Pat. No. 11,057,701.
Declaration of Chris Kyriakakis, Ph.D., Exhibit—1002, Filed on Dec. 21, 2021, challenging U.S. Pat. No. 9,609,424.
Declaration of Christopher J. Struck in Support of Patent Owner's Preliminary Response, Exhibit—2001, Filed on Oct. 7, 2022, challenging U.S. Pat. No. 11,057,701.
Declaration of Christopher J. Struck in Support of Patent Owner's Preliminary Response, Exhibit—2001, Filed on Oct. 7, 2022, challenging U.S. Pat. No. 11,217,237.
Declaration of Christopher J. Struck in Support of Patent Owner's Preliminary Response, Exhibit—2001, Filed on Apr. 13, 2022, challenging U.S. Pat. No. 9,609,424.
Declaration of Christopher J. Struck in Support of Patent Owner's Preliminary Response, Exhibit—2001, Filed on May 18, 2022, challenging U.S. Pat. No. 10,979,836.
Declaration of Christopher J. Struck in Support of Patent Owner's Response, Exhibit—2006, Filed on Oct. 17, 2022, challenging U.S. Pat. No. 9,609,424.
Declaration of Christopher Struck in Support of POR, Exhibit—2013, Filed on Mar. 23, 2023, challenging U.S. Pat. No. 11,057,701.
Declaration of Daniel P. Anagnos in Support of Patent Owner Response; Exhibit—2006, Filed on Sep. 9, 2022, challenging U.S. Pat. No. 9,124,982.

(56) References Cited

OTHER PUBLICATIONS

Declaration of Daniel P. Anagnos in Support of Patent Owner's Preliminary Response, Exhibit—2001, Filed on Apr. 13, 2022, challenging U.S. Pat. No. 8,254,591.
Declaration of Daniel P. Anagnos in Support of Patent Owner's Response, Exhibit—2006, Filed on Oct. 17, 2022, challenging U.S. Pat. No. 8,254,591.
Declaration of Daniel P. Anagnos in Support of Patent Owner's Response, Exhibit—2006, Filed on Sep. 13, 2022, challenging U.S. Pat. No. 8,111,839.
Declaration of Daniel P. Anagnos, Exhibit—2001, Filed on Mar. 23, 2022, challenging U.S. Pat. No. 8,111,839.
Declaration of Daniel P. Anagnos; Exhibit—2001, Filed on Mar. 21, 2022, challenging U.S. Pat. No. 9,124,982.
Declaration of David Kleinschmidt in Support of Patent Owner's Preliminary Response, Exhibit—2001, Filed on Oct. 11, 2022, challenging U.S. Pat. No. 11,039,259.
Declaration of David Kleinschmidt in Support of Patent Owner's Preliminary Response, Exhibit—2001, Filed on Oct. 7, 2022, challenging U.S. Pat. No. 11,244,666.
Declaration of David Kleinschmidt in Support of Patent Owner's Preliminary Response, Exhibit—2001, Filed on Mar. 21, 2022, challenging U.S. Pat. No. 8,315,400.
Declaration of David Kleinschmidt in Support of Patent Owner's Preliminary Response, Exhibit—2001, Filed on Apr. 18, 2022, challenging U.S. Pat. No. 9,491,542.
Declaration of David Kleinschmidt in Support of Patent Owner's Preliminary Response, Exhibit—2001, Filed on Apr. 18, 2022, challenging U.S. Pat. No. 9,270,244.
Declaration of David Kleinschmidt in Support of Patent Owner's Response, Exhibit—2006, Filed on Oct. 19, 2022, challenging U.S. Pat. No. 9,491,542.
Declaration of David Kleinschmidt in Support of Patent Owner's Response, Exhibit—2006, Filed on Oct. 19, 2022, challenging U.S. Pat. No. 9,270,244.
Declaration of David Kleinschmidt in Support of Patent Owner's Response, Exhibit—2009, Filed on Sep. 9, 2022, challenging U.S. Pat. No. 8,315,400.
Declaration of Dr. Chris Kyriakakis, Exhibit—1002, Filed on Jan. 14, 2022, challenging U.S. Pat. No. 10,979,836.
Declaration of Dr. David Anderson Regarding Claim Construction dated Oct. 21, 2022, Exhibit—2011, Filed on Nov. 8, 2022, challenging U.S. Pat. No. 10,966,015.
Declaration of Dr. Eric Tarr, Exhibit—2001, Filed on Dec. 6, 2024, challenging U.S. Pat. No. 11,610,587.
Declaration of Les E. Atlas, Ph.D., Exhibit—1002, Filed on Dec. 13, 2021, challenging U.S. Pat. No. 8,111,839.
Declaration of Les E. Atlas, Ph.D., Exhibit—1002, Filed on Dec. 20, 2021, challenging U.S. Pat. No. 8,254,591.
Declaration of Les E. Atlas, Ph.D., Exhibit—1003, Filed on Dec. 13, 2021, challenging U.S. Pat. No. 8,111,839.
Declaration of Les E. Atlas, Ph.D.; Exhibit—1002, Filed on Dec. 13, 2021, challenging U.S. Pat. No. 9,124,982.
Declaration of Marshall Buck in Support of Patent Owner's Preliminary Response, Exhibit—2001, Filed on May 18, 2022, challenging U.S. Pat. No. 10,405,082.
Declaration of Marshall Buck in Support of Patent Owner's Preliminary Response, Exhibit—2001, Filed on May 18, 2022, challenging U.S. Pat. No. 10,966,015.
Declaration of Marshall D. Buck, Ph.D. in Support of Patent Owner Response, Exhibit—2008, Filed on Nov. 8, 2022, challenging U.S. Pat. No. 10,405,082.
Declaration of Marshall D. Buck, Ph.D. in Support of Patent Owner's Response, Exhibit—2008, Filed on Nov. 8, 2022, challenging U.S. Pat. No. 10,966,015.
Declaration of Nathaniel Polish, Ph.D., Exhibit—1002, Filed on Dec. 17, 2021, challenging U.S. Pat. No. 9,491,542.
Declaration of Nathaniel Polish, Ph.D., Exhibit—1002, Filed on Dec. 21, 2021, challenging U.S. Pat. No. 9,270,244.
Declaration of Richard Stern, Ph.D., Exhibit—1002, Filed on Dec. 10, 2021, challenging U.S. Pat. No. 8,315,400.
Declaration of Richard Stern, Ph.D., Exhibit—1002, Filed on Dec. 30, 2021, challenging U.S. Pat. No. 10,405,082.
Declaration of Roy Falik In Support of Motion for the Pro Hac Vice Admission, Exhibit—2001, Filed on Jul. 5, 2024, challenging U.S. Pat. No. 9,191,083.
Declaration of Roy Falik In Support of Motion for the Pro Hac Vice Admission, Exhibit—2001, Filed on Jul. 5, 2024, challenging U.S. Pat. No. 9,614,943.
Declaration of Roy Falik In Support of Motion for the Pro Hac Vice AdmissionExhibit2001,Jul. 5, 2024, challenging U.S. Pat. No. 8,434,966.
Declaration of Roy Falik, Exhibit—2001, Filed on Jul. 18, 2024, challenging U.S. Pat. No. 7,049,850.
Declaration of Roy Falik, Exhibit—2001, Filed on Jul. 18, 2024, challenging U.S. Pat. No. 9,279,263.
Declaration of Scott Delman with attached exhibit, Exhibit—1024, Filed on Dec. 21, 2021, challenging U.S. Pat. No. 9,270,244.
Deposition Transcript of David Kleinschmidt, dated Jun. 9, 2023, Exhibit—1034, Filed on Jun. 30, 2023, challenging U.S. Pat. No. 11,039,259.
Determining All Challenged Claims Unpatentable 35 U.S.C. § 318(a), Exhibit—31, Filed on Aug. 11, 2023, challenging U.S. Pat. No. 10,966,015.
Determining All Challenged Claims Unpatentable 35 U.S.C. § 318(a), Exhibit—32, Filed on Aug. 11, 2023, challenging U.S. Pat. No. 10,405,082.
Determining All Challenged Claims Unpatentable 35 U.S.C. § 318(a), Exhibit—26, Filed on Nov. 13, 2023, challenging U.S. Pat. No. 11,057,701.
Determining Some Challenged Claims Unpatentable 35 U.S.C. § 318(a), Exhibit—37, Filed on Jul. 7, 2023, challenging U.S. Pat. No. 9,609,424.
Docket Control Order, E.D. Tex., Exhibit—1014, Filed on Apr. 20, 2022, challenging U.S. Pat. No. 8,315,400.
Docket Control Order, E.D. Tex., Exhibit—1043, Filed on Apr. 20, 2022, challenging U.S. Pat. No. 8,111,839.
Docket Control Order, E.D. Tex.; Exhibit—1033, Filed on Apr. 20, 2022, challenging U.S. Pat. No. 9,124,982.
Edwards, The Future of Hearing Aid Technology, Exhibit—2008, Filed on Sep. 13, 2022, challenging U.S. Pat. No. 8,111,839.
EX 1032—Protective Order (*Staton Techiya, LLC* v. *Samsung Electronics Co., Ltd*, 21-CV-00413-JRG-RSP), Exhibit—1032, Filed on Apr. 13, 2023, challenging U.S. Pat. No. 9,609,424.
Ex 1045—Nov. 18, 2022, Deposition Transcript of Daniel P Anagnos, Exhibit—1045, Filed on Dec. 6, 2022, challenging U.S. Pat. No. 8,111,839.
Ex 1046—Patent Owner's Response in IPR2022-00243, Paper 21, Exhibit—1046, Filed on Dec. 6, 2022, challenging U.S. Pat. No. 8,111,839.
Ex 1047—Patent Owner Response for IPR2022-00234, Paper 17, Exhibit—1047, Filed on Dec. 6, 2022, challenging U.S. Pat. No. 8,111,839.
Ex 1048—Institution Decision for IPR2022-00234, Paper 12, Exhibit—1048, Filed on Dec. 6, 2022, challenging U.S. Pat. No. 8,111,839.
Ex 1049—File History for 382 Patent, Exhibit—1049, Filed on Dec. 6, 2022, challenging U.S. Pat. No. 8,111,839.
Ex 1053—Excerpts from The Authoritative Dictionary of IEEE Standards Terms, Exhibit—1053, Filed on Dec. 6, 2022, challenging U.S. Pat. No. 8,111,839.
Ex 1054—Supplemental Declaration of Les E Atlas PhD (Atlas-Supp), Exhibit—1054, Filed on Dec. 6, 2022, challenging U.S. Pat. No. 8,111,839.
Ex. 1002—Declaration of Dr. Les Atlas, Ph.D., Exhibit—1002, Filed on Jun. 9, 2022, challenging U.S. Pat. No. 11,039,259.
Ex. 1002—Declaration of Nathaniel Polish, Ph.D., Exhibit—1002, Filed on Jun. 9, 2022, challenging U.S. Pat. No. 11,217,237.
Ex. 1002—Declaration of Nathaniel Polish, Ph.D., Exhibit—1002, Filed on Jun. 9, 2022, challenging U.S. Pat. No. 11,244,666.
Ex. 1002—Kyriakakis DeclarationExhibit1002,Jun. 18, 2024, challenging U.S. Pat. No. 8,434,966.
Ex. 1002 Declaration of Chris Kyriakakis, Exhibit—1002, Filed on Jul. 1, 2024, challenging U.S. Pat. No. 9,279,263.

(56) References Cited

OTHER PUBLICATIONS

Ex. 1002 Declaration of Dr. Richard M. Stern, Exhibit—1002, Filed on Jun. 9, 2022, challenging U.S. Pat. No. 11,057,701.
Ex. 1003—CV of Dr. Les Atlas, Ph.D., Exhibit—1003, Filed on Jun. 9, 2022, challenging U.S. Pat. No. 11,039,259.
Ex. 1003—CV of Nathaniel Polish, Ph.D., Exhibit—1003, Filed on Jun. 9, 2022, challenging U.S. Pat. No. 11,217,237.
Ex. 1003—CV of Nathaniel Polish, Ph.D., Exhibit—1003, Filed on Jun. 9, 2022, challenging U.S. Pat. No. 11,244,666.
Ex. 1003—Kyriakakis CVExhibit1003,Jun. 18, 2024, challenging U.S. Pat. No. 8,434,966.
Ex. 1003 Chris Kyriakakis CV, Exhibit—1003, Filed on Jul. 1, 2024, challenging U.S. Pat. No. 9,279,263.
Ex. 1003 CV of Dr. Richard M. Stern, Exhibit—1003, Filed on Jun. 9, 2022, challenging U.S. Pat. No. 11,057,701.
Ex. 1004—U.S. Appl. No. 16/571,973 File History for 259, Exhibit—1004, Filed on Jun. 9, 2022, challenging U.S. Pat. No. 11,039,259.
Ex. 1004—File History for U.S. Pat. No. 11,750,965 Exhibit1004,Jun. 18, 2024, challenging U.S. Pat. No. 8,434,966.
Ex. 1004—File History of U.S. Pat. No. 11,217,237, Exhibit—1004, Filed on Jun. 9, 2022, challenging U.S. Pat. No. 11,217,237.
Ex. 1004—File History of U.S. Pat. No. 11,244,666, Exhibit—1004, Filed on Jun. 9, 2022, challenging U.S. Pat. No. 11,244,666.
Ex. 1004 File History for U.S. Pat. No. 11,665,493, Exhibit—1004, Filed on Jul. 1, 2024, challenging U.S. Pat. No. 9,279,263.
Ex. 1004 File History of U.S. Pat. No. 11,057,701, Exhibit—1004, Filed on Jun. 9, 2022, challenging U.S. Pat. No. 11,057,701.
Ex. 1005—U.S. Appl. No. 13/917,079 File History part 1 of 2, Exhibit—1005, Filed on Jun. 9, 2022, challenging U.S. Pat. No. 11,039,259.
Ex. 1005—U.S. Appl. No. 13/917,079 File History part 2 of 2, Exhibit—1005, Filed on Jun. 9, 2022, challenging U.S. Pat. No. 11,039,259.
Ex. 1005 U.S. Appl. No. 61/098,250, Exhibit—1005, Filed on Jul. 1, 2024, challenging U.S. Pat. No. 9,279,263.
Ex. 1006—U.S. Appl. No. 12/555,570 File History, Exhibit—1006, Filed on Jun. 9, 2022, challenging U.S. Pat. No. 11,039,259.
Ex. 1006 U.S. Appl. No. 12/115,349 File History, Exhibit—1006, Filed on Jun. 9, 2022, challenging U.S. Pat. No. 11,057,701.
Ex. 1006 U.S. Appl. No. 12/555,864, Exhibit—1006, Filed on Jul. 1, 2024, challenging U.S. Pat. No. 9,279,263.
Ex. 1007—U.S. Appl. No. 61/096,128 File History, Exhibit—1007, Filed on Jun. 9, 2022, challenging U.S. Pat. No. 11,039,259.
Ex. 1007 U.S. Appl. No. 60/916,271 File History, Exhibit—1007, Filed on Jun. 9, 2022, challenging U.S. Pat. No. 11,057,701.
Ex. 1008—JP3353701B2 to Kondo with Translation, Exhibit—1008, Filed on Jun. 9, 2022, challenging U.S. Pat. No. 11,217,237.
Ex. 1009 Translation of JPA 2002-204500 (Hayashi), Exhibit—1009, Filed on Jul. 1, 2024, challenging U.S. Pat. No. 9,279,263.
Ex. 1010—Redline—965 versus parentExhibit1010,Jun. 18, 2024, challenging U.S. Pat. No. 8,434,966.
Ex. 1012—U.S. Appl. No. 60/893,617 Exhibit1012,Jun. 18, 2024, challenging U.S. Pat. No. 8,434,966.
Ex. 1013—150139_14109987 NOA referred to in 965 NOAExhibit1013,Jun. 18, 2024, challenging U.S. Pat. No. 8,434,966.
Ex. 1013 Deterministic Broad-Band Signal (Chu), Exhibit—1013, Filed on Jul. 1, 2024, challenging U.S. Pat. No. 9,279,263.
Ex. 1013 IPR2022-00282 Patent Owner Preliminary Response, Exhibit—1013, Filed on Jun. 9, 2022, challenging U.S. Pat. No. 11,057,701.
Ex. 1014—Mulgrew 2002, Exhibit—1014, Filed on Jun. 9, 2022, challenging U.S. Pat. No. 11,244,666.
Ex. 1014—Redline—682 parent versus ultimate parent 812Exhibit1014,Jun. 18, 2024, challenging U.S. Pat. No. 8,434,966.
Ex. 1014 701 Patent Family Tree, Exhibit—1014, Filed on Jun. 9, 2022, challenging U.S. Pat. No. 11,057,701.
Ex. 1015—666 Family Tree, Exhibit—1015, Filed on Jun. 9, 2022, challenging U.S. Pat. No. 11,244,666.
Ex. 1015—Letter re 965 IPR StipulationExhibit1015,Jun. 18, 2024, challenging U.S. Pat. No. 8,434,966.
Ex. 1015 Complaint, E.D. Tex. 22-53, Exhibit—1015, Filed on Jun. 9, 2022, challenging U.S. Pat. No. 11,057,701.
Ex. 1016—Complaint, E.D. Tex., 22-53, Exhibit—1016, Filed on Jun. 9, 2022, challenging U.S. Pat. No. 11,244,666.
Ex. 1016 GSM 6.31, Exhibit—1016, Filed on Jun. 9, 2022, challenging U.S. Pat. No. 11,057,701.
Ex. 1016 Reply Declaration of Richard Stern, PhD, Exhibit—1016, Filed on Dec. 2, 2022, challenging U.S. Pat. No. 8,315,400.
Ex. 1017—Amended Complaint, E.D. Tex., 21-413, Exhibit—1017, Filed on Jun. 9, 2022, challenging U.S. Pat. No. 11,244,666.
Ex. 1017—Rose 2003, Exhibit—1017, Filed on Jun. 9, 2022, challenging U.S. Pat. No. 11,039,259.
Ex. 1017 David Kleinschmidt Depo Transcript, Exhibit—1017, Filed on Dec. 2, 2022, challenging U.S. Pat. No. 8,315,400.
Ex. 1017 Final Rejection from Reexam U.S. Appl. No. 90/015,146, Exhibit—1017, Filed on Jul. 1, 2024, challenging U.S. Pat. No. 9,279,263.
Ex. 1017 GSM 6.12, Exhibit—1017, Filed on Jun. 9, 2022, challenging U.S. Pat. No. 11,057,701.
Ex. 1018—Confidential Settlement Agreement with Exhibits A-IExhibit1018, Dec. 11, 2024, challenging U.S. Pat. No. 8,434,966. [Document not publicly available at PTAB].
Ex. 1018—Consolidation Order, E.D. Tex., 21-413 & 22-53, Exhibit—1018, Filed on Jun. 9, 2022, challenging U.S. Pat. No. 11,244,666.
Ex. 1018 Consolidation Order, E.D. Tex. 21-413 & 22-53, Exhibit—1018, Filed on Jun. 9, 2022, challenging U.S. Pat. No. 11,057,701.
Ex. 1018 Excerpts from Wiley Electrical & Electronics Engineering Dictionary, Exhibit—1018, Filed on Dec. 2, 2022, challenging U.S. Pat. No. 8,315,400.
Ex. 1019—Docket Control Order, E.D. Tex., 21-413, Exhibit—1019, Filed on Jun. 9, 2022, challenging U.S. Pat. No. 11,244,666.
Ex. 1019—Duffner 2006, Exhibit—1019, Filed on Jun. 9, 2022, challenging U.S. Pat. No. 11,217,237.
Ex. 1019 Docket Control Order, E.D. Tex. 21-413, Exhibit—1019, Filed on Jun. 9, 2022, challenging U.S. Pat. No. 11,057,701.
Ex. 1019 Dual-Channel MLS-Based Test System (Schneider), Exhibit—1019, Filed on Jul. 1, 2024, challenging U.S. Pat. No. 9,279,263.
Ex. 1020—Letter re IPR Stipulation, Exhibit—1020, Filed on Jun. 9, 2022, challenging U.S. Pat. No. 11,244,666.
Ex. 1020 Letter re IPR Stipulation, Exhibit—1020, Filed on Jun. 9, 2022, challenging U.S. Pat. No. 11,057,701.
Ex. 1021—Complaint. E.D. Tex., 22-00053, Exhibit—1021, Filed on Jun. 9, 2022, challenging U. S. Patent No. 11,217,237.
Ex. 1021—Hsu 2005, Exhibit—1021, Filed on Jun. 9, 2022, challenging U.S. Pat. No. 11,039,259.
Ex. 1021—Stipulation Letter, Exhibit—1021, Filed on May 20, 2022, challenging U.S. Pat. No. 9,491,542.
Ex. 1021 Amended Complaint, E.D. Tex. 21-413, Exhibit—1021, Filed on Jun. 9, 2022, challenging U.S. Pat. No. 11,057,701.
Ex. 1021 Claim Construction Order, ED Tex, Exhibit—1021, Filed on Jul. 1, 2024, challenging U.S. Pat. No. 9,279,263.
Ex. 1022—Amended Complaint, E.D.Tex., 21-00413, Exhibit—1022, Filed on Jun. 9, 2022, challenging U.S. Pat. No. 11,217,237.
Ex. 1022—Complaint, E.D. Tex., Exhibit—1022, Filed on May 20, 2022, challenging U.S. Pat. No. 9,491,542.
Ex. 1022 Letter to Techiya re 493 IPR Stipulation, Exhibit—1022, Filed on Jul. 1, 2024, challenging U.S. Pat. No. 9,279,263.
Ex. 1023—Consolidation Order, E.D. Tex., Exhibit—1023, Filed on May 20, 2022, challenging U.S. Pat. No. 9,491,542.
Ex. 1023—Consolidation Order, E.D.Tex., 21-00413 & 22-00053, Exhibit—1023, Filed on Jun. 9, 2022, challenging U.S. Pat. No. 11,217,237.
Ex. 1023 Techiya Appeal Brief from Reexam U.S. Appl. No. 90/015,146, Exhibit—1023, Filed on Jul. 1, 2024, challenging U.S. Pat. No. 9,279,263.
Ex. 1024—259 Family Tree, Exhibit—1024, Filed on Jun. 9, 2022, challenging U.S. Pat. No. 11,039,259.
Ex. 1024—Docket Control Order, E.D. Tex., 21-00413, Exhibit—1024, Filed on Jun. 9, 2022, challenging U.S. Pat. No. 11,217,237.
Ex. 1024 Judicial Caseload Profile, Exhibit—1024, Filed on Jul. 1, 2024, challenging U.S. Pat. No. 9,279,263.
Ex. 1025—Complaint, E.D. Tex. 22-53, Exhibit—1025, Filed on Jun. 9, 2022, challenging U.S. Pat. No. 11,039,259.

(56) References Cited

OTHER PUBLICATIONS

Ex. 1025—Letter re IPR Stipulation, Exhibit—1025, Filed on Jun. 9, 2022, challenging U.S. Pat. No. 11,217,237.
Ex. 1025—Stipulation Letter, Exhibit—1025, Filed on May 27, 2022, challenging U.S. Pat. No. 9,270,244.
Ex. 1026—237 Family Tree, Exhibit—1026, Filed on Jun. 9, 2022, challenging U.S. Pat. No. 11,217,237.
Ex. 1026—Amended Complaint, E.D. Tex. 21-413, Exhibit—1026, Filed on Jun. 9, 2022, challenging U.S. Pat. No. 11,039,259.
Ex. 1026—Complaint, E.D. Tex., Exhibit—1026, Filed on May 27, 2022, challenging U.S. Pat. No. 9,270,244.
Ex. 1026—Confidential Settlement Agreement, Exhibit—1026, Filed on Dec. 9, 2024, challenging U.S. Pat. No. 9,279,263. [Document not publicly available at PTAB].
Ex. 1027—Confidential Settlement Agreement with Exhibits A-I, Exhibit—1027, Filed on Dec. 11, 2024, challenging U.S. Pat. No. 9,279,263. [Document not publicly available at PTAB].
Ex. 1027—Consolidation Order, E.D. Tex., Exhibit—1027, Filed on May 27, 2022, challenging U.S. Pat. No. 9,270,244.
Ex. 1027—Docket Control Order, E.D. Tex. 21-413, Exhibit—1027, Filed on Jun. 9, 2022, challenging U.S. Pat. No. 11,039,259.
Ex. 1027—Transcript of Deposition of Christopher Struck, Exhibit—1027, Filed on Jan. 10, 2023, challenging U.S. Pat. No. 9,609,424.
Ex. 1028—Consolidation Order, E.D. Tex. 21-413 & 22-53, Exhibit—1028, Filed on Jun. 9, 2022, challenging U.S. Pat. No. 11,039,259.
Ex. 1028—Errata Sheet for Deposition of Christopher Struck, Exhibit—1028, Filed on Jan. 10, 2023, challenging U.S. Pat. No. 9,609,424.
Ex. 1029—Letter re IPR Stipulation, Exhibit—1029, Filed on Jun. 9, 2022, challenging U.S. Pat. No. 11,039,259.
Ex. 1029—Patent Owner's Opening Claim Construction Brief, E.D. Tex., Exhibit—1029, Filed on Jan. 10, 2023, challenging U.S. Pat. No. 9,609,424.
Ex. 1029 Petitioners' Oral Hearing Demonstratives, Exhibit—1029, Filed on Sep. 26, 2023, challenging U.S. Pat. No. 11,057,701.
Ex. 1030—Petitioners' Oral Hearing Demonstratives, Exhibit—1030, Filed on Apr. 11, 2023, challenging U.S. Pat. No. 9,609,424.
Ex. 1033—Confidential Deposition of Christopher Struck, E.D. Tex., Exhibit—1033, Filed on May 15, 2023, challenging U.S. Pat. No. 9,609,424. [Document not publicly available at PTAB].
Ex. 1034—Redacted Deposition of Christopher Struck, E.D. Tex., Exhibit—1034, Filed on May 15, 2023, challenging U.S. Pat. No. 9,609,424.
Ex. 1037—Petitioners' Oral Hearing Demonstratives, Exhibit—1037, Filed on Oct. 11, 2023, challenging U.S. Pat. No. 11,039,259.
Ex. 3001, Exhibit—3001, Filed on Nov. 8, 2024, challenging U.S. Pat. No. 9,191,083.
Ex. 3001, Exhibit—3001, Filed on Nov. 8, 2024, challenging U.S. Pat. No. 9,614,943.
Ex. 3001, Exhibit—3001, Filed on Nov. 8, 2024, challenging U.S. Pat. No. 7,049,850.
Ex. 3001, Exhibit—3001, Filed on Nov. 8, 2024, challenging U.S. Pat. No. 8,434,966.
Ex. 3001, Exhibit—3001, Filed on Nov. 8, 2024, challenging U.S. Pat. No. 9,279,263.
Ex. 3001, Exhibit—3001, Filed on Apr. 6, 2023, challenging U.S. Pat. No. 10,966,015.
EX1002—Declaration of Christopher Schmandt, Exhibit—1002, Filed on Feb. 9, 2024, challenging U.S. Pat. No. 11,610,587.
EX1002—Declaration of Nathaniel Polish, Exhibit—1002, Filed on Jun. 25, 2024, challenging U.S. Pat. No. 7,049,850.
EX1002—Kyriakakis Declaration, Exhibit—1002, Filed on Jun. 12, 2024, challenging U.S. Pat. No. 9,191,083.
EX1002—Kyriakakis Declaration, Exhibit—1002, Filed on Jun. 12, 2024, challenging U.S. Pat. No. 9,614,943.
EX1003—Nathaniel Polish CV, Exhibit—1003, Filed on Jun. 25, 2024, challenging U.S. Pat. No. 7,049,850.
EX1003—Kyriakakis CV, Exhibit—1003, Filed on Jun. 12, 2024, challenging U.S. Pat. No. 9,191,083.
EX1003—Kyriakakis CV, Exhibit—1003, Filed on Jun. 12, 2024, challenging U.S. Pat. No. 9,614,943.
EX1003—Schmandt CV, Exhibit—1003, Filed on Feb. 9, 2024, challenging U.S. Pat. No. 11,610,587.
EX1004—File History for U.S. Appl. No. 11/659,315—Part 1 of 2, Exhibit—1004, Filed on Jun. 25, 2024, challenging U.S. Pat. No. 7,049,850.
EX1004—File History for U.S. Appl. No. 11,659,315—Part 2 of 2, Exhibit—1004, Filed on Jun. 25, 2024, challenging U.S. Pat. No. 7,049,850.
EX1004—File History for U.S. Appl. No. 11,710,473_Part 1 of 3, Exhibit - 1004, Filed on Jun. 12, 2024, challenging U.S. Pat. No. 9,191,083.
EX1004—File History for U.S. Appl. No. 11,710,473_Part 1 of 3, Exhibit—1004, Filed on Jun. 12, 2024, challenging U.S. Pat. No. 9,614,943.
EX1004—File History for U.S. Appl. No. 11,710,473_Part 2 of 3, Exhibit—1004, Filed on Jun. 12, 2024, challenging U.S. Pat. No. 9,191,083.
EX1004—File History for U.S. Appl. No. 11,710,473_Part 2 of 3, Exhibit—1004, Filed on Jun. 12, 2024, challenging U.S. Pat. No. 9,614,943.
EX1004—File History for U.S. Appl. No. 11,710,473_Part 3 of 3, Exhibit—1004, Filed on Jun. 12, 2024, challenging U.S. Pat. No. 9,191,083.
EX1004—File History for U.S. Appl. No. 11,710,473_Part 3 of 3, Exhibit—1004, Filed on Jun. 12, 2024, challenging U.S. Pat. No. 9,614,943.
EX1004—USFH11610587 Part 1 of 2, Exhibit—1004, Filed on Feb. 9, 2024, challenging U.S. Pat. No. 11,610,587.
EX1004—USFH11610587 Part 2 of 2, Exhibit—1004, Filed on Feb. 9, 2024, challenging U.S. Pat. No. 11,610,587.
EX1005—U.S. Appl. No. 60/885,917, Exhibit—1005, Filed on Jun. 12, 2024, challenging U.S. Pat. No. 9,191,083.
EX1005—U.S. Appl. No. 60/885,917, Exhibit—1005, Filed on Jun. 12, 2024, challenging U.S. Pat. No. 9,614,943.
EX1005—U.S. Appl. No. 61/737,932 Provisional, Exhibit—1005, Filed on Jun. 12, 2024, challenging U.S. Pat. No. 7,049,850.
EX1005—U.S. Appl. No. 61/098,914 (Provisional Application), Exhibit—1005, Filed on Feb. 9, 2024, challenging U.S. Pat. No. 11,610,587.
EX1006—U.S. Appl. No. 16/266,829 (829 App), Exhibit—1006, Filed on Jun. 25, 2024, challenging U.S. Pat. No. 7,049,850.
EX1006—U.S. Appl. 17/321,892, Exhibit—1006, Filed on Jun. 12, 2024, challenging U.S. Pat. No. 9,191,083.
EX1006—U.S. Appl. No. 17/321,892, Exhibit—1006, Filed on Jun. 12, 2024, challenging U.S. Pat. No. 9,614,943.
EX1006—U.S. Appl. No. 17/203,731, Exhibit—1006, Filed on Feb. 9, 2024, challenging U.S. Pat. No. 11,610,587.
EX1007—315 Patent Family Tree, Exhibit—1007, Filed on Jun. 25, 2024, challenging U.S. Pat. No. 7,049,850.
EX1008—Docket Control Order, Exhibit—1008, Filed on Jun. 25, 2024, challenging U.S. Pat. No. 7,049,850.
EX1008—File History for U.S. Pat. No. 11/244,666, Exhibit—1008, Filed on Jun. 12, 2024, challenging U.S. Pat. No. 9,191,083.
EX1008—File History for U.S. Pat. No. 11/244,666, Exhibit—1008, Filed on Jun. 12, 2024, challenging U.S. Pat. No. 9,614,943.
EX1009—Letter from Nikhil Krishnan to Thomas J. Friel, Jr., Exhibit—1009, Filed on Jun. 25, 2024, challenging U.S. Pat. No. 7,049,850.
EX1009—U.S. Appl. No. 90/019,169 RE of U.S. Appl. No. 11/244,666_Part 1 of 5, Exhibit—1009, Filed on Jun. 12, 2024, challenging U.S. Pat. No. 9,191,083.
EX1009—U.S. Appl. No. 90/019,169 RE of U.S. Appl. No. 11/244,666_Part 1 of 5, Exhibit—1009, Filed on Jun. 12, 2024, challenging U.S. Pat. No. 9,614,943.
EX1009—U.S. Appl. No. 90/019,169 RE of U.S. Appl. No. 11/244,666_Part 2 of 5, Exhibit—1009, Filed on Jun. 12, 2024, challenging U.S. Pat. No. 9,191,083.
EX1009—U.S. Appl. No. 90/019,169 RE of U.S. Appl. No. 11/244,666_Part 2 of 5, Exhibit—1009, Filed on Jun. 12, 2024, challenging U.S. Pat. No. 9,614,943.

(56) References Cited

OTHER PUBLICATIONS

EX1009—U.S. Appl. No. 90/019,169 RE of U.S. Appl. No. 11/244,666_Part 3 of 5, Exhibit—1009, Filed on Jun. 12, 2024, challenging U.S. Pat. No. 9,191,083.
EX1009—U.S. Appl. No. 90/019,169 RE of U.S. Appl. No. 11/244,666_Part 3 of 5, Exhibit—1009, Filed on Jun. 12, 2024, challenging U.S. Pat. No. 9,614,943.
EX1009—U.S. Appl. No. 90/019,169 RE of U.S. Appl. No. 11/244,666_Part 4 of 5, Exhibit—1009, Filed on Jun. 12, 2024, challenging U.S. Pat. No. 9,191,083.
EX1009—U.S. Appl. No. 90/019,169 RE of U.S. Appl. No. 11/244,666_Part 4 of 5, Exhibit—1009, Filed on Jun. 12, 2024, challenging U.S. Pat. No. 9,614,943.
EX1009—U.S. Appl. No. 90/019,169 RE of U.S. Appl. No. 11/244,666_Part 5 of 5, Exhibit—1009, Filed on Jun. 12, 2024, challenging U.S. Pat. No. 9,191,083.
EX1009—U.S. Appl. No. 90/019,169 RE of U.S. Appl. No. 11/244,666_Part 5 of 5, Exhibit—1009, Filed on Jun. 12, 2024, challenging U.S. Pat. No. 9,614,943.
EX1010—473 Patent Family Tree, Exhibit—1010, Filed on Jun. 12, 2024, challenging U.S. Pat. No. 9,191,083.
EX1010—473 Patent Family Tree, Exhibit—1010, Filed on Jun. 12, 2024, challenging U.S. Pat. No. 9,614,943.
EX1011—Claim Construction Order, ED Tex, Exhibit—1011, Filed on Jun. 12, 2024, challenging U.S. Pat. No. 9,191,083.
EX1011—Claim Construction Order, ED Tex, Exhibit—1011, Filed on Jun. 12, 2024, challenging U.S. Pat. No. 9,614,943.
EX1012—Docket Control Order, ED Tex, Exhibit—1012, Filed on Jun. 12, 2024, challenging U.S. Pat. No. 9,191,083.
EX1012—Docket Control Order, ED Tex, Exhibit—1012, Filed on Jun. 12, 2024, challenging U.S. Pat. No. 9,614,943.
EX1013—Letter from Nikhil Krishnan to Thomas J Friel, Jr, Exhibit—1013, Filed on Jun. 12, 2024, challenging U.S. Pat. No. 9,191,083.
EX1013—Letter from Nikhil Krishnan to Thomas J Friel, Jr, Exhibit—1013, Filed on Jun. 12, 2024, challenging U.S. Pat. No. 9,614,943.
EX1016—Stay Order from E.D. Tex.Exhibit1016, Nov. 20, 2024, challenging U.S. Pat. No. 8,434,966.
EX1019—U.S. Appl. No. 60/841,990 (Rosenberg Provisional) (annotated), Exhibit—1019, Filed on Jun. 12, 2024, challenging U.S. Pat. No. 9,191,083.
EX1023—Preliminary Constructions, E.D. Tex., Exhibit—1023, Filed on Jan. 31, 2023, challenging U.S. Pat. No. 10,405,082.
EX1023—Preliminary Constructions, E.D. Tex., Exhibit—1023, Filed on Jan. 31, 2023, challenging U.S. Pat. No. 10,966,015.
EX1024—Cohen, Exhibit—1024, Filed on Feb. 9, 2024, challenging U.S. Pat. No. 11,610,587.
EX1024—Transcript of Deposition of Marshall Buck, Exhibit—1024, Filed on Jan. 31, 2023, challenging U.S. Pat. No. 10,405,082.
EX1024—Transcript of Deposition of Marshall Buck, Exhibit—1024, Filed on Jan. 31, 2023, challenging U.S. Pat. No. 10,966,015.
EX1025—Blattner et al, Earcons and Icons, Exhibit—1025, Filed on Jun. 25, 2024, challenging U.S. Pat. No. 7,049,850.
Ex1025—Deposition Transcript of David Kleinschmidt, Exhibit—1025, Filed on Jan. 11, 2023, challenging U.S. Pat. No. 9,491,542.
EX1025—Stay Order from E.D. Tex., Exhibit—1025, Filed on Nov. 20, 2024, challenging U.S. Pat. No. 9,279,263.
EX1025—Tanenbaum, Exhibit—1025, Filed on Feb. 9, 2024, challenging U.S. Pat. No. 11,610,587.
EX1025 Petitioners' Oral Hearing Demonstratives, Exhibit—1025, Filed on May 9, 2023, challenging U.S. Pat. No. 10,405,082.
EX1025 Petitioners' Oral Hearing Demonstratives, Exhibit—1025, Filed on May 9, 2023, challenging U.S. Pat. No. 10,966,015.
Ex1026—Cessation from Merriam-Webster's Collegiate Dictionary, 10th Ed, Exhibit—1026, Filed on Jan. 11, 2023, challenging U.S. Pat. No. 9,491,542.
EX1026—Computer Dictionary 2nd Ed, Exhibit—1026, Filed on Feb. 9, 2024, challenging U.S. Pat. No. 11,610,587.

Ex1027—Cessation from New World Dictionary, 2d College Ed, Exhibit—1027, Filed on Jan. 11, 2023, challenging U.S. Pat. No. 9,491,542.
EX1028—Basu, Exhibit—1028, Filed on Jun. 12, 2024, challenging U.S. Pat. No. 9,191,083.
EX1028—Basu, Smart Headphones, Exhibit—1028, Filed on Jun. 12, 2024, challenging U.S. Pat. No. 9,614,943.
Ex1028—Supplemental Declaration of Nathanial Polish, Ph.D., Exhibit—1028, Filed on Jan. 11, 2023, challenging U.S. Pat. No. 9,491,542.
EX1029—Declaration of Nathanial Polish, Exhibit—1029, Filed on Jan. 11, 2023, challenging U.S. Pat. No. 9,270,244.
EX1029—Mueller, Transparent Hearing, Exhibit—1029, Filed on Jun. 12, 2024, challenging U.S. Pat. No. 9,191,083.
EX1029—Mueller, Transparent Hearing, Exhibit—1029, Filed on Jun. 12, 2024, challenging U.S. Pat. No. 9,614,943.
EX1030—Deposition Transcript of David Kleinschmidt, Exhibit—1030, Filed on Jan. 11, 2023, challenging U.S. Pat. No. 9,270,244.
EX1031—587 Patent Family Tree, Exhibit—1031, Filed on Feb. 9, 2024, challenging U.S. Pat. No. 11,610,587.
EX1031—Basu, et al, Smart Headphones, Exhibit—1031, Filed on Jun. 25, 2024, challenging U.S. Pat. No. 7,049,850.
EX1031—Cessation from Merriam-Webster's Collegiate Dictionary, 10th Ed, Exhibit—1031, Filed on Jan. 11, 2023, challenging U.S. Pat. No. 9,270,244.
EX1031—Patent Rule 4-3 Joint Claim Construction and Prehearing Statement, E.D. Tx, Exhibit—1031, Filed on Mar. 7, 2023, challenging U.S. Pat. No. 9,491,542.
EX1032—Cessation from New World Dictionary, 2d College Ed, Exhibit—1032, Filed on Jan. 11, 2023, challenging U.S. Pat. No. 9,270,244.
EX1032—Ex. A-01_U.S. Appl. No. 11/610,587 Samsung Infringement Claim Chart, Exhibit—1032, Filed on Feb. 9, 2024, challenging U.S. Pat. No. 11,610,587.
EX1032—Excerpts from Microsoft Computer Dictionary, 4th ed, Exhibit—1032, Filed on Jun. 25, 2024, challenging U.S. Pat. No. 7,049,850.
Ex1032—Petitioners' Oral Hearing Demonstratives, Exhibit—1032, Filed on Apr. 12, 2023, challenging U.S. Pat. No. 9,491,542.
EX1033—Order Granting Proposed Docket Control Order, Exhibit—1033, Filed on Feb. 9, 2024, challenging U.S. Pat. No. 11,610,587.
EX1033—Pending from Merriam-Webster's Collegiate Dictionary, 10th Ed, Exhibit—1033, Filed on Jan. 11, 2023, challenging U.S. Pat. No. 9,270,244.
EX1034—Computer Dictionary 2nd Ed, Exhibit—1034, Filed on Jun. 12, 2024, challenging U.S. Pat. No. 9,191,083.
EX1034—D Del Statistics, Exhibit—1034, Filed on Feb. 9, 2024, challenging U.S. Pat. No. 11,610,587.
EX1034—Pause from Merriam-Webster's Collegiate Dictionary, 10th Ed, Exhibit—1034, Filed on Jan. 11, 2023, challenging U.S. Pat. No. 9,270,244.
EX1035—Deposition Transcript for Daniel P. Anagnos, Exhibit—1035, Filed on Jan. 10, 2023, challenging U.S. Pat. No. 8,254,591.
EX1035—File History of U.S. Appl. No. 10/635,382; Exhibit—1035, Filed on Dec. 2, 2022, challenging U.S. Pat. No. 9,124,982.
EX1035—Letter to Techiya re 587 IPR Stipulation, Exhibit—1035, Filed on Feb. 9, 2024, challenging U.S. Pat. No. 11,610,587.
EX1035—National Judicial Caseload Profile, Exhibit—1035, Filed on Jun. 25, 2024, challenging U.S. Pat. No. 7,049,850.
EX1035—Patent Rule 4-3 Joint Claim Construction and Prehearing Statement, E.D. Tx, Exhibit—1035, Filed on Mar. 7, 2023, challenging U.S. Pat. No. 9,270,244.
EX1035—Tanenbaum Excerpt, Exhibit—1035, Filed on Jun. 12, 2024, challenging U.S. Pat. No. 9,191,083.
EX1036—Linkedin Profile for Harish Jonnalagadda, Exhibit—1036, Filed on Jan. 10, 2023, challenging U.S. Pat. No. 8,254,591.
EX1036—Oshana excerpt, Exhibit—1036, Filed on Jun. 12, 2024, challenging U.S. Pat. No. 9,191,083.
EX1036—Oshana excerpt, Exhibit—1036, Filed on Jun. 12, 2024, challenging U.S. Pat. No. 9,614,943.
EX1036—Petitioners' Oral Hearing Demonstratives, Exhibit—1036, Filed on Apr. 13, 2023, challenging U.S. Pat. No. 9,270,244.

(56) References Cited

OTHER PUBLICATIONS

EX1036—Stay Order from E.D. Tex., Exhibit—1036, Filed on Nov. 20, 2024, challenging U.S. Pat. No. 7,049,850.
EX1037—Confidential Settlement Agrement with Exhibits A-I, Exhibit—1037, Filed on Dec. 11, 2024, challenging U.S. Pat. No. 11,610,587. [Document not publicly available at PTAB].
EX1038—Confidential Settlement Agreement with Exhibits A-I, Exhibit—1038, Filed on Dec. 11, 2024, challenging U.S. Pat. No. 7,049,850. [Document not publicly available at PTAB].
EX1038—Handbook for Sound Engineers_Part 1 of 2, Exhibit—1038, Filed on Jun. 12, 2024, challenging U.S. Pat. No. 9,191,083.
EX1038—Handbook for Sound Engineers_Part 2 of 2, Exhibit—1038, Filed on Jun. 12, 2024, challenging U.S. Pat. No. 9,191,083.
EX1040—IPR2022-00234, Ex 2001, Declaration of Daniel P Anagnos; Exhibit—1040, Filed on Dec. 2, 2022, challenging U.S. Pat. No. 9,124,982.
EX1041—Nov. 18, 2022, Deposition Transcript of Daniel P Anagnos; Exhibit—1041, Filed on Dec. 2, 2022, challenging U.S. Pat. No. 9,124,982.
EX1041—Supplemental Declaration of Les E. Atlas, Ph.D., Exhibit—1041, Filed on Jan. 10, 2023, challenging U.S. Pat. No. 8,254,591.
EX1042—Excerpts from the Authoritative Dictionary of IEEE Standards Terms; Exhibit—1042, Filed on Dec. 2, 2022, challenging U.S. Pat. No. 9,124,982.
Ex1042—Petitioners' Oral Hearing Demonstratives, Exhibit—1042, Filed on Apr. 4, 2023, challenging U.S. Pat. No. 8,254,591.
EX1043—Institution Decision, IPR2022-00234, Paper 16; Exhibit—1043, Filed on Dec. 2, 2022, challenging U.S. Pat. No. 9,124,982.
EX1044—Patent Owner Response, IPR2022-00234, Paper 22; Exhibit—1044, Filed on Dec. 2, 2022, challenging U.S. Pat. No. 9,124,982.
EX1045—Excerpt of Prosecution History of U.S. Appl. No. 17/483,190, Exhibit—1045, Filed on Jun. 12, 2024, challenging U.S. Pat. No. 9,191,083.
EX1056—U.S. Appl. No. 11/710,473 Samsung Infringement Claim Chart, Ex. A-06, Exhibit—1056, Filed on Jun. 12, 2024, challenging U.S. Pat. No. 9,191,083.
EX1056—U.S. Appl. No. 11/710,473 Samsung Infringement Claim Chart, Ex. A-06, Exhibit—1056, Filed on Jun. 12, 2024, challenging U.S. Pat. No. 9,614,943.
EX1058—Kuo, Active Noise Control, Exhibit—1058, Filed on Jun. 12, 2024, challenging U.S. Pat. No. 9,614,943.
Ex1058—Petitioners' Oral Hearing Demonstratives, Exhibit—1058, Filed on Mar. 16, 2023, challenging U.S. Pat. No. 8,111,839.
EX1059—Stay Order from E.D. Tex., Exhibit—1059, Filed on Nov. 20, 2024, challenging U.S. Pat. No. 9,191,083.
EX1059—Stay Order from E.D. Tex., Exhibit—1059, Filed on Nov. 20, 2024, challenging U.S. Pat. No. 9,614,943.
EX1061—Confidential Settlement Agreement with Exhibits A-I, Exhibit—1061, Filed on Dec. 11, 2024, challenging U.S. Pat. No. 9,614,943. [Document not publicly available at PTAB].
EX1061—Confidential Settlement Agrement with Exhibits A-I, Exhibit—1061, Filed on Dec. 11, 2024, challenging U.S. Pat. No. 9,191,083. [Document not publicly available at PTAB].
Excerpt from Computer Dictionary, 2d ed., Exhibit—1027, Filed on Dec. 13, 2021, challenging U.S. Pat. No. 8,111,839.
Excerpt from Computer Dictionary, 2d ed.; Exhibit—1029, Filed on Dec. 13, 2021, challenging U.S. Pat. No. 9,124,982.
Excerpt from Dictionary of Scientific and Technical Terms, 5th ed., Exhibit—1026, Filed on Dec. 20, 2021, challenging U.S. Pat. No. 8,254,591.
Excerpt from McGraw Hill Dictionary of Scientific and Technical Terms, 5th ed., Exhibit—1025, Filed on Dec. 13, 2021, challenging U.S. Pat. No. 8,111,839.
Excerpt from Oshana; Exhibit—1030, Filed on Dec. 13, 2021, challenging U.S. Pat. No. 9,124,982.
Excerpt of File History of U.S. Appl. No. 12/100,281; Exhibit—1006, Filed on Dec. 13, 2021, challenging U.S. Pat. No. 9,124,982.
Excerpt of File History of U.S. Appl. No. 13/352,694; Exhibit—1007, Filed on Dec. 13, 2021, challenging U.S. Pat. No. 9,124,982.
Excerpts from Federal Court Management Statistics, Exhibit—1022, Filed on Jul. 1, 2022, challenging U.S. Pat. No. 10,405,082.
Excerpts from Federal Court Management Statistics, Exhibit—1022, Filed on Jul. 1, 2022, challenging U.S. Pat. No. 10,966,015.
Excerpts from Federal Court Management Statistics, Exhibit—1023, Filed on Jul. 1, 2022, challenging U.S. Pat. No. 10,979,836.
Excerpts from Federal Court Management Statistics, Exhibit—1024, Filed on Jul. 1, 2022, challenging U.S. Pat. No. 9,491,542.
Excerpts from Federal Court Management Statistics, Exhibit—1026, Filed on Jul. 1, 2022, challenging U.S. Pat. No. 9,609,424.
Excerpts from Federal Court Management Statistics, Exhibit—1028, Filed on Jul. 1, 2022, challenging U.S. Pat. No. 9,270,244.
Excerpts from Federal Court Management Statistics, Exhibit—1034, Filed on Jul. 1, 2022, challenging U.S. Pat. No. 8,254,591.
Excerpts from McGraw-Hill Dictionary of Scientific and Technical Terms, 5th ed.; Exhibit—1021, Filed on Dec. 13, 2021, challenging U.S. Pat. No. 9124982.
Excerpts from Openheim, Exhibit - 1016, Filed on Jan. 4, 2022, challenging U.S. Pat. No. 10,966,015.
Excerpts from Oppenheim & Schafer, 3rd ed., Exhibit—1016, Filed on Dec. 30, 2021, challenging U.S. Pat. No. 10,405,082.
Excerpts from Oshana, Exhibit—1027, Filed on Dec. 20, 2021, challenging U.S. Pat. No. 8,254,591.
Excerpts from Oshana, Exhibit—1028, Filed on Dec. 13, 2021, challenging U.S. Pat. No. 8,111,839.
Exhibit 3001, Exhibit—3001, Filed on Jan. 5, 2023, challenging U.S. Pat. No. 8,315,400.
Exhibit 3001, Exhibit—3001, Filed on Nov. 3, 2022, challenging U.S. Pat. No. 11,057,701.
Exhibit 3001, Exhibit—3001, Filed on Nov. 3, 2022, challenging U.S. Pat. No. 11,039,259.
Exhibit 3001, Exhibit—3001, Filed on Apr. 6, 2023, challenging U.S. Pat. No. 10,405,082.
Expunged, Exhibit—1002, Filed on Jan. 4, 2022, challenging U.S. Pat. No. 10,966,015. [Document expunged from PTAB record].
Expunged, Exhibit—1006, Filed on Dec. 13, 2021, challenging U.S. Pat. No. 8,111,839.
Expunged, Exhibit—1031, Filed on Apr. 13, 2023, challenging U.S. Pat. No. 9,609,424.
Expunged, Exhibit—1036, Filed on Dec. 9, 2024, challenging U.S. Pat. No. 11,610,587. [Document expunged from PTAB record].
Expunged, Exhibit—1037, Filed on Dec. 9, 2024, challenging U.S. Pat. No. 7,049,850. [Document expunged from PTAB record].
Expunged, Exhibit—1060, Filed on Dec. 9, 2024, challenging U.S. Pat. No. 9,191,083. [Document expunged from PTAB record].
Expunged, Exhibit—1060, Filed on Dec. 9, 2024, challenging U.S. Pat. No. 9,614,943. [Document expunged from PTAB record].
Expunged, Exhibit—11, Filed on Jan. 18, 2023, challenging U.S. Pat. No. 11,244,666. [Document expunged from PTAB record].
Expunged, Exhibit—12, Filed on Jan. 18, 2023, challenging U.S. Pat. No. 11,217,237. [Document expunged from PTAB record].
Expunged, Exhibit—2008, Filed on Feb. 22, 2023, challenging U.S. Pat. No. 9,270,244.
Expunged, Exhibit—3, Filed on Dec. 10, 2021, challenging U.S. Pat. No. 8,315,400. [Document expunged from PTAB record].
Expunged, Exhibit—3, Filed on Jun. 9, 2022, challenging U.S. Pat. No. 11,217,237. [Document expunged from PTAB record].
Expunged, Exhibit—3002, Filed on Apr. 6, 2023, challenging U.S. Pat. No. 10,966,015. [Document expunged from PTAB record].
Expunged, Exhibit—37, Filed on Aug. 15, 2023, challenging U.S. Pat. No. 8,111,839.
Expungedexhibit1017, Dec. 9, 2024, challenging U.S. Pat. No. 8,434,966. [Document expunged from PTAB record].
Extract from Federal Court Management Statistics, Exhibit—1021, Filed on Nov. 10, 2022, challenging U.S. Pat. No. 11,244,666.
Extract from Federal Court Management Statistics, Exhibit—1024, Filed on Nov. 10, 2022, challenging U.S. Pat. No. 11,057,701.
Extract from Federal Court Management Statistics, Exhibit—1027, Filed on Nov. 15, 2022, challenging U.S. Pat. No. 11,217,237.
Extract from Federal Court Management Statistics, Exhibit—1030, Filed on Nov. 10, 2022, challenging U.S. Pat. No. 11,039,259.
Federal Court Management Statistics (excerpt), Exhibit—2004, Filed on Jul. 1, 2022, challenging U.S. Pat. No. 9,491,542.

(56) References Cited

OTHER PUBLICATIONS

Federal Court Management Statistics (excerpt), Exhibit—2004, Filed on Jul. 1, 2022, challenging U.S. Pat. No. 9,270,244.
Federal Court Management Statistics (excerpt), Exhibit—2004, Filed on Jul. 1, 2022, challenging U.S. Pat. No. 9,609,424.
Federal Court Management Statistics (excerpt), Exhibit—2004, Filed on Jul. 1, 2022, challenging U.S. Pat. No. 8,254,591.
Federal Court Management Statistics (excerpt), Exhibit—2005, Filed on Jul. 1, 2022, challenging U.S. Pat. No. 10,405,082.
Federal Court Management Statistics (excerpt), Exhibit—2005, Filed on Jul. 1, 2022, challenging U.S. Pat. No. 10,979,836.
Federal Court Management Statistics (excerpt), Exhibit—2006, Filed on Jul. 1, 2022, challenging U.S. Pat. No. 10,966,015.
File History for U.S. Pat. No. 9,491,542, Exhibit—1004, Filed on Dec. 17, 2021, challenging U.S. Pat. No. 9,491,542.
File History of U.S. Appl. No. 16/168,752, Exhibit—2005, Filed on May 15, 2022, challenging U.S. Pat. No. 10,966,015.
File History of U.S. Appl. No. 12/555,864, Exhibit—1012, Filed on Jan. 14, 2022, challenging U.S. Pat. No. 10,979,836.
File History of U.S. Appl. No. 14/054,015, Exhibit—1011, Filed on Jan. 14, 2022, challenging U.S. Pat. No. 10,979,836.
File History of U.S. Appl. No. 14/827,332, Exhibit—1010, Filed on Jan. 14, 2022, challenging U.S. Pat. No. 10,979,836.
File History of U.S. Appl. No. 15/700,511, Exhibit—1009, Filed on Jan. 14, 2022, challenging U.S. Pat. No. 10,979,836.
File History of U.S. Appl. No. 16/414,136, Exhibit—1013, Filed on Jan. 14, 2022, challenging U.S. Pat. No. 10,979,836.
File History of U.S. Pat. No. 8,111,839, Exhibit—1005, Filed on Dec. 13, 2021, challenging U.S. Pat. No. 8,111,839.
File History of U.S. Pat. No. 8,254,591, Exhibit—1004, Filed on Dec. 20, 2021, challenging U.S. Pat. No. 8,254,591.
File History of U.S. Pat. No. 9,124,982; Exhibit—1004, Filed on Dec. 13, 2021, challenging U.S. Pat. No. 9,124,982.
File History of U.S. Pat. No. 10,405,082, Exhibit—1004, Filed on Dec. 30, 2021, challenging U.S. Pat. No. 10,405,082.
File History of U.S. Pat. No. 10,966,015, Exhibit—1005, Filed on Jan. 4, 2022, challenging U.S. Pat. No. 10,966,015.
File History of U.S. Pat. No. 10,979,836,, U.S. Appl. No. 16/838,277, Exhibit—1004, Filed on Jan. 14, 2022, challenging U.S. Pat. No. 10,979,836.
File History of U.S. Pat. No. 8,315,400, Exhibit—1004, Filed on Dec. 10, 2021, challenging U.S. Pat. No. 8,315,400.
File History of U.S. Pat. No. 8,774,433, Exhibit—1009, Filed on Dec. 21, 2021, challenging U.S. Pat. No. 9,609,424.
File History of U.S. Pat. No. 9,270,244, Exhibit—1004, Filed on Dec. 21, 2021, challenging U.S. Pat. No. 9,270,244.
File History of U.S. Pat. No. 9,332,364, Exhibit—1005, Filed on Dec. 21, 2021, challenging U.S. Pat. No. 9,609,424.
File History of U.S. Pat. No. 9,609,424, Exhibit—1004, Filed on Dec. 21, 2021, challenging U.S. Pat. No. 9,609,424.
File History of U.S. Appl. No. 60/910,808; Exhibit—1005, Filed on Dec. 13, 2021, challenging U.S. Pat. No. 9,124,982.
File History of U.S. Appl. No. 61/098,250, Exhibit—1005, Filed on Jan. 14, 2022, challenging U.S. Pat. No. 10,979,836.
File History of U.S. Appl. No. 60/619,517 (Allen Provisional), Exhibit—1020, Filed on Dec. 21, 2021, challenging U.S. Pat. No. 9,609,424.
File History of U.S. Appl. No. 60/866,420, Exhibit—1010, Filed on Dec. 21, 2021, challenging U.S. Pat. No. 9,609,424.
Final Written Decision, IPR2022-00282 (Paper No. 28, Jun. 14, 2023), Exhibit—1035, Filed on Jun. 30, 2023, challenging U.S. Pat. No. 11,039,259.
Final Written Decision: Final Written Decision Determining All Challenged Claims Unpatentable 35 U.S.C. sec. 318a, Exhibit—32, Filed on Jan. 5, 2024, challenging U.S. Pat. No. 11,039,259.
Final Written Decision: original, Exhibit—28, Filed on Jun. 14, 2023, challenging U.S. Pat. No. 8,315,400.
Final Written Decision: original, Exhibit—31, Filed on Jul. 13, 2023, challenging U.S. Pat. No. 9,270,244.
Final Written Decision: original, Exhibit—33, Filed on Jul. 10, 2023, challenging U.S. Pat. No. 8,254,591.
Final Written Decision: original, Exhibit—33, Filed on Jul. 14, 2023, challenging U.S. Pat. No. 9,491,542.
Final Written Decision: original, Exhibit—36, Filed on Jun. 16, 2023, challenging U.S. Pat. No. 8,111,839.
Final Written Decision: original; Exhibit—29, Filed on Jun. 14, 2023, challenging U.S. Pat. No. 9124982.
Final Written Decision: Judgment Final Written Decision Determining All Challenged Claims Unpatentable 35 U.S.C. § 318(a), Exhibit—35, Filed on Jun. 20, 2023, challenging U.S. Pat. No. 8,111,839.
First Amended Complaint, *Staton Techiya v. Samsung, E.D. Tex.*, Exhibit—1008, Filed on Dec. 10, 2021, challenging U.S. Pat. No. 8,315,400.
First Amended Complaint, *Techiya v. Samsung, E.D. Tex.*, Exhibit—1018, Filed on Dec. 21, 2021, challenging U.S. Pat. No. 9,270,244.
First Amended Complaint, *Techiya v. Samsung, E.D. Tex.*, Exhibit—1020, Filed on Dec. 17, 2021, challenging U.S. Pat. No. 9,491,542.
First Amended Complaint, *Techiya v. Samsung, E.D. Tex.*, Exhibit—1029, Filed on Dec. 20, 2021, challenging U.S. Pat. No. 8,254,591.
First Amended Complaint, *Techiya v. Samsung, E.D. Tex.*, Exhibit—1040, Filed on Dec. 13, 2021, challenging U.S. Pat. No. 8,111,839.
First Amended Complaint, *Techiya v. Samsung, E.D. Tex.*; Exhibit—1031, Filed on Dec. 13, 2021, challenging U.S. Pat. No. 9,124,982.
Granting Institution of Inter Partes Review 35 U.S.C. § 314, Exhibit—13, Filed on Jul. 15, 2022, challenging U.S. Pat. No. 9,491,542.
Granting Institution of Inter Partes Review 35 U.S.C. § 314, Exhibit—13, Filed on Jul. 15, 2022, challenging U.S. Pat. No. 9,270,244.
Granting Institution of Inter Partes Review 35 U.S.C. § 314, Exhibit—13, Filed on Aug. 16, 2022, challenging U.S. Pat. No. 10,966,015.
Granting Institution of Inter Partes Review 35 U.S.C. § 314, Exhibit—14, Filed on Aug. 16, 2022, challenging U.S. Pat. No. 10,405,082.
Harman Q&As about Microphone Windscreens, Exhibit—2013, Filed on Sep. 13, 2022, challenging U.S. Pat. No. 8,111,839.
Harman, Q&As about Microphone Screens; Exhibit—2012, Filed on Sep. 9, 2022, challenging U.S. Pat. No. 9,124,982.
IEEE Dictionary of Standards Terms (excerpts), Exhibit—2006, Filed on Mar. 21, 2022, challenging U.S. Pat. No. 8,315,400.
Institution Decision: Deny, Exhibit—12, Filed on Aug. 12, 2022, challenging U.S. Pat. No. 10,979,836.
Institution Decision: Grant, Exhibit—10, Filed on Jan. 9, 2023, challenging U.S. Pat. No. 11,039,259.
Institution Decision: Grant, Exhibit—12, Filed on Jun. 17, 2022, challenging U.S. Pat. No. 8,315,400.
Institution Decision: Grant, Exhibit—13, Filed on Jul. 11, 2022, challenging U.S. Pat. No. 9,609,424.
Institution Decision: Grant, Exhibit—13, Filed on Jul. 11, 2022, challenging U.S. Pat. No. 8,254,591.
Institution Decision: Grant, Exhibit—15, Filed on Jun. 21, 2022, challenging U.S. Pat. No. 8,111,839.
Institution Decision: Grant, Exhibit—16, Filed on Jun. 21, 2022, challenging U.S. Pat. No. 8,111,839.
Institution Decision: Grant, Exhibit—8, Filed on Aug. 16, 2024, challenging U.S. Pat. No. 11,610,587.
Institution Decision: Grant; Exhibit—12, Filed on Jun. 17, 2022, challenging U.S. Pat. No. 9,124,982.
Joint Motion to Consolidate; Exhibit—2005, Filed on Apr. 29, 2022, challenging U.S. Pat. No. 9,124,982.
Joint Motion to Terminate Proceeding, Exhibit—17, Filed on Dec. 9, 2024, challenging U.S. Pat. No. 11,610,587.
Joint Request to Treat Settlement Agreement as Business Confidential Information, Exhibit—14, Filed on Dec. 9, 2024, challenging U.S. Pat. No. 9,191,083.
Joint Request to Treat Settlement Agreement as Business Confidential Information, Exhibit—14, Filed on Dec. 9, 2024, challenging U.S. Pat. No. 9,614,943.

(56) References Cited

OTHER PUBLICATIONS

Joint Request to Treat Settlement Agreement as Business Confidential Information, Exhibit—14, Filed on Dec. 9, 2024, challenging U.S. Pat. No. 7,049,850.
Joint Request to Treat Settlement Agreement as Business Confidential Information, Exhibit—15, Filed on Dec. 9, 2024, challenging U.S. Pat. No. 9,279,263.
Joint Request to Treat Settlement Agreement as Business Confidential Information, Exhibit—18, Filed on Dec. 9, 2024, challenging U.S. Pat. No. 11,610,587.
Joint Request to Treat Settlement Agreement as Business Confidential InformationPaper13, Dec. 9, 2024, challenging U.S. Pat. No. 8,434,966.
Joint Statement Regarding Oral Argument, Exhibit—15, Filed on Jul. 29, 2022, challenging U.S. Pat. No. 9,491,542.
Joint Statement Regarding Oral Argument, Exhibit—15, Filed on Jul. 29, 2022, challenging U.S. Pat. No. 9,270,244.
Joint Statement Regarding Oral Argument, Exhibit—15, Filed on Jul. 29, 2022, challenging U.S. Pat. No. 9,609,424.
Joint Statement Regarding Oral Argument, Exhibit—15, Filed on Aug. 24, 2022, challenging U.S. Pat. No. 10,966,015.
Joint Statement Regarding Oral Argument, Exhibit—16, Filed on Jul. 29, 2022, challenging U.S. Pat. No. 8,254,591.
Joint Statement Regarding Oral Argument, Exhibit—16, Filed on Aug. 24, 2022, challenging U.S. Pat. No. 10,405,082.
Joint Statement Regarding Oral Argument, Exhibit—18, Filed on Jul. 29, 2022, challenging U.S. Pat. No. 8,111,839.
Joint Statement Regarding Oral Argument, Exhibit—19, Filed on Jul. 29, 2022, challenging U.S. Pat. No. 8,111,839.
Joint Stipulation To Modify Due Dates 1-3, Exhibit—10, Filed on Oct. 25, 2024, challenging U.S. Pat. No. 11,610,587.
Joint Stipulation To Modify Due Dates 1-3, Exhibit—12, Filed on Nov. 22, 2024, challenging U.S. Pat. No. 11,610,587.
Joint Stipulation to Modify Scheduling Order, Exhibit—14, Filed on Mar. 14, 2023, challenging U.S. Pat. No. 11,039,259.
Joint Stipulation to Modify the Scheduling Order, Exhibit—16, Filed on Aug. 16, 2022, challenging U.S. Pat. No. 9,491,542.
Joint Stipulation to Modify the Scheduling Order, Exhibit—16, Filed on Aug. 16, 2022, challenging U.S. Pat. No. 9,270,244.
Joint Stipulation to Modify the Scheduling Order, Exhibit—16, Filed on Aug. 16, 2022, challenging U.S. Pat. No. 9,609,424.
Joint Stipulation to Modify the Scheduling Order, Exhibit—19, Filed on Aug. 16, 2022, challenging U.S. Pat. No. 8,254,591.
Kleinschmidt Declaration in Support of Patent Owner Response, Exhibit—2018, Filed on Apr. 10, 2023, challenging U.S. Pat. No. 11,039,259.
LEAP Practitioner Request and Verification Form (Patent Owner), Exhibit—29, Filed on Feb. 28, 2023, challenging U.S. Pat. No. 8,111,839.
LEAP Practitioner Request and Verification Form (Patent Owner), Exhibit—30, Filed on Feb. 28, 2023, challenging U.S. Pat. No. 8,111,839.
LEAP Practitioner Request and Verification Form (Petitioner), Exhibit—30, Filed on Mar. 13, 2023, challenging U.S. Pat. No. 8,111,839.
LEAP Practitioner Request and Verification Form (Petitioner), Exhibit—31, Filed on Mar. 13, 2023, challenging U.S. Pat. No. 8,111,839.
Letter from Petitioners' Counsel to PO's Counsel Apr. 20, 2022, Exhibit—2004, Filed on May 18, 2022, challenging U.S. Pat. No. 10,405,082.
Letter from Petitioners' Counsel to PO's Counsel Apr. 20, 2022, Exhibit—2004, Filed on May 18, 2022, challenging U.S. Pat. No. 10,966,015.
Letter from Petitioners' Counsel to PO's Counsel Apr. 20, 2022, Exhibit—2004, Filed on May 18, 2022, challenging U.S. Pat. No. 10,979,836.
Markman Hearing Transcript (excerpts), Exhibit—2022, Filed on Oct. 19, 2023, challenging U.S. Pat. No. 11,039,259.
Mauer, Embedded Indexing, Exhibit—2008, Filed on Sep. 13, 2022, challenging U.S. Pat. No. 8,111,839.
Mauer, Embedded Indexing: Pros and Cons for the Indexer; Exhibit—2008, Filed on Sep. 9, 2022, challenging U.S. Pat. No. 9,124,982.
McGraw-Hill Dictionary of Scientific and Technical Terms, Exhibit—2010, Filed on Sep. 13, 2022, challenging U.S. Pat. No. 8,111,839.
McGraw-Hill Dictionary of Scientific and Technical Terms; Exhibit—2009, Filed on Sep. 9, 2022, challenging U.S. Pat. No. 9,124,982.
Merriam-Webster's Collegiate Dictionary (excerpt), Exhibit—2010, Filed on Oct. 11, 2022, challenging U.S. Pat. No. 11,039,259.
Montgomery Declaration with Exhibit A, Exhibit—1018, Filed on Jan. 14, 2022, challenging U.S. Pat. No. 10,979,836.
Motion for Leave to File Corrected Petition, Exhibit—10, Filed on Jan. 31, 2022, challenging U.S. Pat. No. 8,111,839.
Motion: Motion to dismiss due to settlement (pre-DI), Exhibit—13, Filed on Dec. 9, 2024, challenging U.S. Pat. No. 9,191,083.
Motion: Motion to dismiss due to settlement (pre-DI), Exhibit—13, Filed on Dec. 9, 2024, challenging U.S. Pat. No. 9,614,943.
Motion: Motion to dismiss due to settlement (pre-DI), Exhibit—13, Filed on Dec. 9, 2024, challenging U.S. Pat. No. 7,049,850.
Motion: Motion to dismiss due to settlement (pre-DI), Exhibit—14, Filed on Dec. 9, 2024, challenging U.S. Pat. No. 9,279,263.
Motion: Motion to dismiss due to settlement (pre-DI)Paper12, Dec. 9, 2024, challenging U.S. Pat. No. 8,434,966.
Notice : Mandatory Notice, Exhibit—5, Filed on Jul. 16, 2024, challenging U.S. Pat. No. 7,049,850.
Notice : Mandatory Notice, Exhibit—6, Filed on Jul. 16, 2024, challenging U.S. Pat. No. 9,279,263.
Notice : Mandatory Notice, Exhibit—7, Filed on Mar. 1, 2024, challenging U.S. Pat. No. 11,610,587.
Notice : Other—Notice of Ranking, Exhibit—4, Filed on Jul. 1, 2024, challenging U.S. Pat. No. 9,279,263.
Notice : Power of Attorney for Harman International Industries, Exhibit—3, Filed on Feb. 9, 2024, challenging U.S. Pat. No. 11,610,587.
Notice : Power of Attorney for Harman International Industries, Inc., Exhibit—3, Filed on Jun. 25, 2024, challenging U.S. Pat. No. 7,049,850.
Notice : Power of Attorney for Harman International Industries, Inc., Exhibit—3, Filed on Jul. 1, 2024, challenging U.S. Pat. No. 9,279,263.
Notice : Power of Attorney for Samsung Electronics America, Exhibit—2, Filed on Feb. 9, 2024, challenging U.S. Pat. No. 11,610,587.
Notice : Power of Attorney for Samsung Electronics America, Inc., Exhibit—2, Filed on Jun. 12, 2024, challenging U.S. Pat. No. 9,191,083.
Notice : Power of Attorney for Samsung Electronics America, Inc., Exhibit—2, Filed on Jun. 12, 2024, challenging U.S. Pat. No. 9,614,943.
Notice : Power of Attorney for Samsung Electronics America, Inc., Exhibit—2, Filed on Jun. 25, 2024, challenging U.S. Pat. No. 7,049,850.
Notice : Power of Attorney for Samsung Electronics America, Inc., Exhibit—2, Filed on Jul. 1, 2024, challenging U.S. Pat. No. 9,279,263.
Notice : Power of Attorney for Samsung Electronics America, Inc. Paper2,Jun. 18, 2024, challenging U.S. Pat. No. 8,434,966.
Notice : Power of Attorney for Samsung Electronics Co., Ltd., Exhibit—1, Filed on Feb. 9, 2024, challenging U.S. Pat. No. 11,610,587.
Notice : Power of Attorney for Samsung Electronics Co., Ltd., Exhibit—1, Filed on Jun. 12, 2024, challenging U.S. Pat. No. 9,191,083.
Notice : Power of Attorney for Samsung Electronics Co., Ltd., Exhibit—1, Filed on Jun. 12, 2024, challenging U.S. Pat. No. 9,614,943.
Notice : Power of Attorney for Samsung Electronics Co., Ltd., Exhibit—1, Filed on Jul. 1, 2024, challenging U.S. Pat. No. 9,279,263.
Notice : Power of Attorney for Samsung Electronics Co., Ltd. Paper1,Jun. 18, 2024, challenging U.S. Pat. No. 8,434,966.
Notice : Power of Attorney for Samsung Electronics Corp., Exhibit—1, Filed on Jun. 25, 2024, challenging U.S. Pat. No. 7,049,850.

(56) References Cited

OTHER PUBLICATIONS

Notice : Power of Attorney, Exhibit—6, Filed on Mar. 1, 2024, challenging U.S. Pat. No. 11,610,587.
Notice : Power of Attorney, Exhibit—6, Filed on Jul. 16, 2024, challenging U.S. Pat. No. 7,049,850.
Notice : Power of Attorney, Exhibit—7, Filed on Jul. 16, 2024, challenging U.S. Pat. No. 9,279,263.
Notice of Deposition of Chris Kyriakakis, Ph.D., Exhibit—17, Filed on Sep. 13, 2022, challenging U.S. Pat. No. 9,609,424.
Notice of Deposition of Daniel P Anagnos, Exhibit—21, Filed on Dec. 14, 2022, challenging U.S. Pat. No. 8,254,591.
Notice of Deposition of David Kleinschmidt, Exhibit—20, Filed on Dec. 2, 2022, challenging U.S. Pat. No. 9,491,542.
Notice of Deposition of David Kleinschmidt, Exhibit—20, Filed on Dec. 2, 2022, challenging U.S. Pat. No. 9,270,244.
Notice of Deposition of Les E. Atlas, Ph.D., Exhibit—13, Filed on Mar. 9, 2023, challenging U.S. Pat. No. 11,039,259.
Notice of Deposition of Les E. Atlas, Ph.D., Exhibit—17, Filed on Aug. 8, 2022, challenging U.S. Pat. No. 8,254,591.
Notice of Deposition of Les E. Atlas, Ph.D., Exhibit—19, Filed on Aug. 4, 2022, challenging U.S. Pat. No. 8,111,839.
Notice of Deposition of Les E. Atlas, Ph.D., Exhibit—20, Filed on Aug. 4, 2022, challenging U.S. Pat. No. 8,111,839.
Notice of Deposition of Les E. Atlas, Ph.D.; Exhibit—15, Filed on Aug. 4, 2022, challenging U.S. Pat. No. 9,124,982.
Notice of Deposition of Marshall Buck, Exhibit—19, Filed on Dec. 16, 2022, challenging U.S. Pat. No. 10,966,015.
Notice of Deposition of Marshall Buck, Exhibit—20, Filed on Dec. 16, 2022, challenging U.S. Pat. No. 10,405,082.
Notice of Deposition of Nathaniel Polish, Ph.D., Exhibit—18, Filed on Sep. 13, 2022, challenging U.S. Pat. No. 9,491,542.
Notice of Deposition of Nathaniel Polish, Ph.D., Exhibit—18, Filed on Sep. 13, 2022, challenging U.S. Pat. No. 9,270,244.
Notice of Deposition of Richard M. Stern, Ph.D., Exhibit—13, Filed on Feb. 28, 2023, challenging U.S. Pat. No. 11,057,701.
Notice of Deposition of Richard M. Stern, Ph.D., Exhibit—14, Filed on Aug. 5, 2022, challenging U.S. Pat. No. 8,315,400.
Notice of Deposition of Richard M. Stern, Ph.D., Exhibit—17, Filed on Oct. 14, 2022, challenging U.S. Pat. No. 10,966,015.
Notice of Deposition of Richard M. Stern, Ph.D., Exhibit—18, Filed on Oct. 14, 2022, challenging U.S. Pat. No. 10,405,082.
Notice of Filing Date Accorded To Petition, Exhibit—5, Filed on Dec. 23, 2021, challenging U.S. Pat. No. 8,111,839.
Notice of Ranking, Exhibit—4, Filed on Dec. 13, 2021, challenging U.S. Pat. No. 8,111,839.
Notice of Ranking, Exhibit—4, Filed on Jun. 12, 2024, challenging U.S. Pat. No. 9,191,083.
Notice of Ranking, Exhibit—4, Filed on Jun. 12, 2024, challenging U.S. Pat. No. 9,614,943.
Notice Regarding Transcript of Markman Hearing, Exhibit—29, Filed on Oct. 19, 2023, challenging U.S. Pat. No. 11,039,259.
Notice: Notice filing date accorded, Exhibit—5, Filed on Dec, 21, 2021, challenging U.S. Pat. No. 8,315,400.
Notice: Notice filing date accorded, Exhibit—5, Filed on Feb. 27, 2024, challenging U.S. Pat. No. 11,610,587.
Notice: Notice filing date accorded, Exhibit—5, Filed on Jun. 17, 2024, challenging U.S. Pat. No. 9,191,083.
Notice: Notice filing date accorded, Exhibit—5, Filed on Jun. 18, 2024, challenging U.S. Pat. No. 9,614,943.
Notice: Notice filing date accorded, Exhibit—6, Filed on Jan. 13, 2022, challenging U.S. Pat. No. 9,609,424.
Notice: Notice filing date accorded, Exhibit—6, Filed on Jan. 13, 2022, challenging U.S. Pat. No. 8,254,591.
Notice: Notice filing date accorded, Exhibit—6, Filed on Jan. 18, 2022, challenging U.S. Pat. No. 9,491,542.
Notice: Notice filing date accorded, Exhibit—6, Filed on Jan. 18, 2022, challenging U.S. Pat. No. 9,270,244.
Notice: Notice filing date accorded, Exhibit—6, Filed on Feb. 18, 2022, challenging U.S. Pat. No. 10,979,836.
Notice: Notice filing date accorded, Exhibit—6, Filed on Jul. 7, 2022, challenging U.S. Pat. No. 11,057,701.
Notice: Notice filing date accorded, Exhibit—6, Filed on Jul. 7, 2022, challenging U.S. Pat. No. 11,244,666.
Notice: Notice filing date accorded, Exhibit—6, Filed on Jul. 8, 2022, challenging U.S. Pat. No. 11,039,259.
Notice: Notice filing date accorded, Exhibit—7, Filed on Feb. 18, 2022, challenging U.S. Pat. No. 10,966,015.
Notice: Notice filing date accorded, Exhibit—7, Filed on Jul. 7, 2022, challenging U.S. Pat. No. 11,217,237.
Notice: Notice filing date accorded, Exhibit—8, Filed on Feb. 18, 2022, challenging U.S. Pat. No. 10,405,082.
Notice: Notice filing date accorded, Exhibit—8, Filed on Jul. 24, 2024, challenging U.S. Pat. No. 7,049,850.
Notice: Notice filing date accorded, Exhibit—9, Filed on Aug. 16, 2024, challenging U.S. Pat. No. 9,279,263.
Notice: Notice filing date accorded; Exhibit—4, Filed on Dec. 21, 2021, challenging U.S. Pat. No. 9,124,982.
Notice: Notice filing date accordedPaper4,Jun. 20, 2024, challenging U.S. Pat. No. 8,434,966.
Notice: refund approved, Exhibit—13, Filed on Mar. 7, 2023, challenging U.S. Pat. No. 11,244,666.
Notice: refund approved, Exhibit—14, Filed on Jan. 20, 2023, challenging U.S. Pat. No. 10,979,836.
Notice: refund approved, Exhibit—14, Filed on Mar. 7, 2023, challenging U.S. Pat. No. 11,217,237.
Notice: refund approved, Exhibit—18, Filed on Dec. 17, 2024, challenging U.S. Pat. No. 9,191,083.
Notice: refund approved, Exhibit—18, Filed on Dec. 17, 2024, challenging U.S. Pat. No. 9,614,943.
Notice: refund approved, Exhibit—18, Filed on Dec. 17, 2024, challenging U.S. Pat. No. 7,049,850.
Notice: refund approved, Exhibit—19, Filed on Dec. 17, 2024, challenging U.S. Pat. No. 9,279,263.
Notice: refund approvedPaper17, Dec. 17, 2024, challenging U.S. Pat. No. 8,434,966.
Olwal 2005, Exhibit—1023, Filed on Dec. 21, 2021, challenging U.S. Pat. No. 9,270,244.
Order Adopting Claim Construction Order, Exhibit—2015, Filed on Apr. 10, 2023, challenging U. S. Pat. No. 11,039,259.
Order Clarifying Claim Construction Order, Exhibit—2014, Filed on Apr. 10, 2023, challenging U.S. Pat. No. 11,039,259.
Order Conditionally Granting Patent Owner's Motion to Withdraw and Substitute Counsel 37 C.F.R. § 42.10, Exhibit—12, Filed on Dec. 9, 2024, challenging U.S. Pat. No. 9,191,083.
Order Conditionally Granting Patent Owner's Motion to Withdraw and Substitute Counsel 37 C.F.R. § 42.10, Exhibit—12, Filed on Dec. 9, 2024, challenging U.S. Pat. No. 9,614,943.
Order Conditionally Granting Patent Owner's Motion to Withdraw and Substitute Counsel 37 C.F.R. § 42.10, Exhibit—12, Filed on Dec. 9, 2024, challenging U.S. Pat. No. 7,049,850.
Order Conditionally Granting Patent Owner's Motion to Withdraw and Substitute Counsel 37 C.F.R. § 42.10, Exhibit—13, Filed on Dec. 9, 2024, challenging U.S. Pat. No. 9,279,263.
Order Conditionally Granting Patent Owner's Motion to Withdraw and Substitute Counsel 37 C.F.R. § 42. 10Paper11, Dec. 9, 2024, challenging U.S. Pat. No. 8,434,966.
Order Conditionally Granting Patent Owner's Motion to Withdraw and Substitute Counsel, Exhibit—13, Filed on Dec. 5, 2024, challenging U.S. Pat. No. 11,610,587.
Order Granting Patent Owner's Motions for Pro Hac Vice Admission of Roy Falik 37 C.F.R. § 42.10(c), Exhibit—9, Filed on Sep. 23, 2024, challenging U.S. Pat. No. 7,049,850.
Order Trial Hearing 37 C.F.R. 42.70, Exhibit—23, Filed on Feb. 6, 2023, challenging U.S. Pat. No. 8,315,400.
Order Trial Hearing 37 C.F.R. 42.70; Exhibit—24, Filed on Feb. 6, 2023, challenging U.S. Pat. No. 9,124,982.
Order Trial Hearing 37 C.F.R. § 42.70, Exhibit—24, Filed on Mar. 1, 2023, challenging U.S. Pat. No. 9,609,424.
Order Trial Hearing 37 C.F.R. § 42.70, Exhibit—26, Filed on Oct. 10, 2023, challenging U.S. Pat. No. 11,039,259.
Order Trial Hearing 37 C.F.R. § 42.70, Exhibit—26, Filed on Mar. 1, 2023, challenging U.S. Pat. No. 8,254,591.

(56) References Cited

OTHER PUBLICATIONS

Order Trial Hearing 37 C.F.R. sec 42.70, Exhibit—28, Filed on Feb. 8, 2023, challenging U.S. Pat. No. 8,111,839.
Order Trial Hearing 37 C.F.R. sec 42.70, Exhibit—29, Filed on Feb. 8, 2023, challenging U.S. Pat. No. 8,111,839.
Order Trial Hearing, Exhibit—25, Filed on Mar. 1, 2023, challenging U.S. Pat. No. 9,270,244.
Order Vacating Standing Orders, Exhibit—2005, Filed on Jul. 1, 2022, challenging U.S. Pat. No. 9,491,542.
Order Vacating Standing Orders, Exhibit—2005, Filed on Jul. 1, 2022, challenging U.S. Pat. No. 9,270,244.
Order Vacating Standing Orders, Exhibit—2005, Filed on Jul. 1, 2022, challenging U.S. Pat. No. 9,609,424.
Order Vacating Standing Orders, Exhibit—2005, Filed on Jul. 1, 2022, challenging U.S. Pat. No. 8,254,591.
Order Vacating Standing Orders, Exhibit—2006, Filed on Jul. 1, 2022, challenging U.S. Pat. No. 10,405,082.
Order Vacating Standing Orders, Exhibit—2006, Filed on Jul. 1, 2022, challenging U.S. Pat. No. 10,979,836.
Order Vacating Standing Orders, Exhibit—2007, Filed on Jul. 1, 2022, challenging U.S. Pat. No. 10,966,015.
Order: Conduct of the Proceeding 37 C.F.R. sec. 42.5, Exhibit—18, Filed on Jan. 5, 2023, challenging U.S. Pat. No. 8,315,400.
Order: Granting Patent Owner's Motion for Pro Hac Vice Admission of Roy Falik 37 C.F.R. § 42.10, Exhibit—10, Filed on Oct. 4, 2024, challenging U.S. Pat. No. 9,279,263.
Order: Granting Patent Owner's Motions for Admission Pro Hac Vice of Roy Falik 37 C.F.R. § 42.10, Exhibit—9, Filed on Oct. 4, 2024, challenging U.S. Pat. No. 9,614,943.
Order: Granting Patent Owner's Motions for Admission Pro Hac Vice of Roy Falik 37 C.F.R. § 42. 10Paper8, Oct. 4, 2024, challenging U.S. Pat. No. 8,434,966.
Order: on Motion, Exhibit—9, Filed on Oct. 4, 2024, challenging U.S. Pat. No. 9,191,083.
Order: Order Setting Oral Argument 37 C.F.R. § 42.70, Exhibit—22, Filed on Aug. 21, 2023, challenging U.S. Pat. No. 11,057,701.
Order: Other, Exhibit—12, Filed on Feb. 22, 2023, challenging U.S. Pat. No. 11,057,701.
Order: Panel Change Order, Exhibit—22, Filed on Feb. 10, 2023, challenging U.S. Pat. No. 9,491,542.
Order: Scheduling Order, Exhibit—13, Filed on Jun. 17, 2022, challenging U.S. Pat. No. 8,315,400.
Order: Scheduling Order; Exhibit—13, Filed on Jun. 17, 2022, challenging U.S. Pat. No. 9,124,982.
Order: Trial Hearing (Revised), Exhibit—27, Filed on Mar. 3, 2023, challenging U.S. Pat. No. 8,254,591.
Order: Trial Hearing—37 CFR 42.70, Exhibit—26, Filed on Mar. 2, 2023, challenging U.S. Pat. No. 9,491,542.
Order: Hearing Order, Exhibit—26, Filed on Apr. 7, 2023, challenging U.S. Pat. No. 10,966,015.
Order: Hearing Order, Exhibit—27, Filed on Apr. 7, 2023, challenging U.S. Pat. No. 10,405,082.
Order: Trial Hearing (Revised), Exhibit—25, Filed on Mar. 3, 2023, challenging U.S. Pat. No. 9,609,424.
Osha, Appx A to 1910.95—Noise Exposure Computation, Exhibit—2014, Filed on Sep. 13, 2022, challenging U.S. Pat. No. 8, 111,839.
Osha, Appx A to 1910.95—Noise Exposure Computation; Exhibit—2013, Filed on Sep. 9, 2022, challenging U.S. Pat. No. 9,124,982.
Oshana, Chapters 3-4, Exhibit—1017, Filed on Jan. 14, 2022, challenging U.S. Pat. No. 10,979,836.
Other: Hearing transcript, Exhibit—25, Filed on Oct. 16, 2023, challenging U.S. Pat. No. 11,057,701.
Other: Hearing transcript, Exhibit—27, Filed on Apr. 18, 2023, challenging U.S. Pat. No. 8,315,400.
Other: Hearing transcript, Exhibit—30, Filed on Jul. 25, 2023, challenging U.S. Pat. No. 10,966,015.
Other: Hearing transcript, Exhibit—31, Filed on Dec. 13, 2023, challenging U.S. Pat. No. 11,039,259.
Other: Hearing transcript, Exhibit—31, Filed on Jul. 25, 2023, challenging U.S. Pat. No. 10,405,082.
Other: Hearing transcript, Exhibit—32, Filed on Jul. 3, 2023, challenging U.S. Pat. No. 8,254,591.
Other: Hearing transcript, Exhibit—32, Filed on Jul. 31, 2023, challenging U.S. Pat. No. 9,270,244.
Other: Hearing transcript, Exhibit—32, Filed on Jul. 6, 2023, challenging U.S. Pat. No. 9,491,542.
Other: Hearing transcript, Exhibit—34, Filed on Jun. 1, 2023, challenging U.S. Pat. No. 8,111,839.
Other: Hearing transcript, Exhibit—34, Filed on Jun. 22, 2023, challenging U.S. Pat. No. 9,609,424.
Other: Hearing transcript, Exhibit—35, Filed on Jun. 1, 2023, challenging U.S. Pat. No. 8,111,839.
Other: Hearing transcript, Exhibit—36, Filed on Jul. 6, 2023, challenging U.S. Pat. No. 9,609,424.
Other: Hearing transcript; Exhibit—28, Filed on Apr. 18, 2023, challenging U.S. Pat. No. 9,124,982.
Other: Order Granting Motion for Leave to File Corrected Petition , Exhibit—10, Filed on Feb. 2, 2022, challenging U.S. Pat. No. 8,111,839.
Other: Order Granting Motion for Leave to File Corrected Petition , Exhibit—11, Filed on Feb. 2, 2022, challenging U.S. Pat. No. 8,111,839.
Other: Fed Circuit mandate, Exhibit—34, Filed on Jun. 27, 2024, challenging U.S. Pat. No. 11,039,259.
Other: Fed Circuit mandate, Exhibit—36, Filed on Jun. 27, 2024, challenging U.S. Pat. No. 8,254,591.
Oxford Dictionary of Elecs and Electrical Eng (excerpts), Exhibit—2005, Filed on Mar. 21, 2022, challenging U.S. Pat. No. 8,315,400.
P.R. 4-5(d) Joint Claim Construction Chart, Exhibit—2009, Filed on Feb. 22, 2023, challenging U.S. Pat. No. 9,491,542.
P.R. 4-5(d) Joint Claim Construction Chart, Exhibit—2009, Filed on Feb. 22, 2023, challenging U.S. Pat. No. 9,270,244.
Panel Change Order, Exhibit—12, Filed on Feb. 3, 2023, challenging U.S. Pat. No. 11,039,259.
Patent Owner Brief Regarding Interim Procedure for Discretionary Denials, Exhibit—12, Filed on Jul. 1, 2022, challenging U.S. Pat. No. 9,491,542.
Patent Owner Response; Exhibit—17, Filed on Sep. 9, 2022, challenging U.S. Pat. No. 9,124,982.
Patent Owner Stanton Techiya LLC's Mandatory NoticePaper6,Jul. 3, 2024, challenging U.S. Pat. No. 8,434,966.
Patent Owner Staton Techiya, LLC's Mandatory Notice, Exhibit—7, Filed on Jul. 3, 2024, challenging U.S. Pat. No. 9,614,943.
Patent Owner Staton Techiya, LLC's Mandatory Notices, Exhibit—7, Filed on Jul. 3, 2024, challenging U.S. Pat. No. 9,191,083.
Patent Owner Staton Techiya, LLC's Motion for the Pro Hac Vice Admission of Roy Falik, Exhibit 8, Filed on Jul. 5, 2024, challenging U.S. Pat. No. 9,191,083.
Patent Owner Staton Techiya, LLC's Motion for the Pro Hac Vice Admission of Roy Falik, Exhibit—8, Filed on Jul. 5, 2024, challenging U.S. Pat. No. 9,614,943.
Patent Owner Staton Techiya, LLC's Motion for the Pro Hac Vice Admission of Roy FalikPaper7,Jul. 5, 2024, challenging U.S. Pat. No. 8,434,966.
Patent Owner Staton Techiya, LLC's Power of Attorney, Exhibit—6, Filed on Jul. 3, 2024, challenging U.S. Pat. No. 9,191,083.
Patent Owner Staton Techiya, LLC's Power of Attorney, Exhibit—6, Filed on Jul. 3, 2024, challenging U.S. Pat. No. 9,614,943.
Patent Owner Staton Techiya, LLC's Power of AttorneyPaper5,Jul. 3, 2024, challenging U.S. Pat. No. 8,434,966.
Patent Owner's Brief Regarding Interim Procedure for Discretionary Denials, Exhibit—11, Filed on Jul. 1, 2022, challenging U.S. Pat. No. 10,979,836.
Patent Owner's Brief Regarding Interim Procedure for Discretionary Denials, Exhibit—12, Filed on Jul. 1, 2022, challenging U.S. Pat. No. 9,270,244.
Patent Owner's Brief Regarding Interim Procedure for Discretionary Denials, Exhibit—12, Filed on Jul. 1, 2022, challenging U.S. Pat. No. 9,609,424.
Patent Owner's Brief Regarding Interim Procedure for Discretionary Denials, Exhibit—12, Filed on Jul. 1, 2022, challenging U.S. Pat. No. 8,254,591.

(56) References Cited

OTHER PUBLICATIONS

Patent Owner's Brief Regarding Interim Procedure for Discretionary Denials, Exhibit—12, Filed on Jul. 1, 2022, challenging U.S. Pat. No. 10,966,015.
Patent Owner's Brief Regarding Interim Procedure for Discretionary Denials, Exhibit—13, Filed on Jul. 1, 2022, challenging U.S. Pat. No. 10,405,082.
Patent Owner's Corrected Notice of Appeal, Exhibit—38, Filed on Aug. 15, 2023, challenging U. S. Pat. No. 8,111,839.
Patent Owner's Demonstratives, Exhibit—2008, Filed on Apr. 11, 2023, challenging U.S. Pat. No. 9,609,424.
Patent Owner's Demonstratives, Exhibit—2010, Filed on Apr. 12, 2023, challenging U.S. Pat. No. 9,491,542.
Patent Owner's Demonstratives, Exhibit—2010, Filed on Apr. 13, 2023, challenging U.S. Pat. No. 9,270,244.
Patent Owner's Demonstratives, Exhibit—2010, Filed on Apr. 4, 2023, challenging U.S. Pat. No. 8,254,591.
Patent Owner's Demonstratives, Exhibit—2012, Filed on May 9, 2023, challenging U.S. Pat. No. 10,405,082.
Patent Owner's Demonstratives, Exhibit—2012, Filed on May 9, 2023, challenging U.S. Pat. No. 10,966,015.
Patent Owner's Demonstratives, Exhibit—2014, Filed on Mar. 14, 2023, challenging U.S. Pat. No. 8,315,400.
Patent Owner's Demonstratives, Exhibit—2014, Filed on Sep. 25, 2023, challenging U.S. Pat. No. 11,057,701.
Patent Owner's Demonstratives, Exhibit—2015, Filed on Mar. 16, 2023, challenging U.S. Pat. No. 8,111,839.
Patent Owner's Demonstratives, Exhibit—2021, Filed on Oct. 11, 2023, challenging U.S. Pat. No. 11,039,259.
Patent Owner's Demonstratives; Exhibit—2014, Filed on Mar. 14, 2023, challenging U.S. Pat. No. 9,124,982.
Patent Owner's Mandatory Notice under 37 C.F.R. 42.8, Exhibit—5, Filed on Jan. 19, 2022, challenging U.S. Pat. No. 10,966,015.
Patent Owner's Mandatory Notice under 37 C.F.R. 42.8, Exhibit—5, Filed on Jan. 19, 2022, challenging U.S. Pat. No. 10,979,836.
Patent Owner's Mandatory Notice under 37 C.F.R. 42.8, Exhibit—5, Filed on Dec. 28, 2021, challenging U.S. Pat. No. 9,491,542.
Patent Owner's Mandatory Notice under 37 C.F.R. 42.8, Exhibit—5, Filed on Dec. 28, 2021, challenging U.S. Pat. No. 9,270,244.
Patent Owner's Mandatory Notice under 37 C.F.R. 42.8, Exhibit—5, Filed on Dec. 28, 2021, challenging U.S. Pat. No. 9,609,424.
Patent Owner's Mandatory Notice under 37 C.F.R. 42.8, Exhibit—5, Filed on Dec. 28, 2021, challenging U.S. Pat. No. 8,254,591.
Patent Owner's Mandatory Notice under 37 C.F.R. 42.8, Exhibit—5, Filed on Jun. 22, 2022, challenging U.S. Pat. No. 11,057,701.
Patent Owner's Mandatory Notice under 37 C.F.R. 42.8, Exhibit—5, Filed on Jun. 22, 2022, challenging U.S. Pat. No. 11,244,666.
Patent Owner's Mandatory Notice under 37 C.F.R. 42.8, Exhibit—5, Filed on Jun. 22, 2022, challenging U.S. Pat. No. 11,039,259.
Patent Owner's Mandatory Notice under 37 C.F.R. 42.8, Exhibit—6, Filed on Jun. 22, 2022, challenging U.S. Pat. No. 11,217,237.
Patent Owner's Mandatory Notice under 37 C.F.R. 42.8, Exhibit—7, Filed on Dec. 28, 2021, challenging U.S. Pat. No. 8,111,839.
Patent Owner's Mandatory Notice under 37 C.F.R. 42.8, Exhibit—7, Filed on Dec. 28, 2021, challenging U.S. Pat. No. 8,315,400.
Patent Owner's Mandatory Notice under 37 C.F.R. 42.8; Exhibit—6, Filed on Dec. 28, 2021, challenging U.S. Pat. No. 9,124,982.
Patent Owner's Mandatory Notice under 37 CFR 42.8, Exhibit—6, Filed on Jan. 19, 2022, challenging U.S. Pat. No. 10,405,082.
Patent Owner's Notice of Appeal, Exhibit—30, Filed on Aug. 11, 2023, challenging U.S. Pat. No. 8,315,400.
Patent Owner's Notice of Appeal, Exhibit—33, Filed on Mar. 5, 2024, challenging U.S. Pat. No. 11,039,259.
Patent Owner's Notice of Appeal, Exhibit—33, Filed on Sep. 8, 2023, challenging U.S. Pat. No. 9,270,244.
Patent Owner's Notice of Appeal, Exhibit—34, Filed on Sep. 8, 2023, challenging U.S. Pat. No. 9,491,542.
Patent Owner's Notice of Appeal, Exhibit—34, Filed on Sep. 8, 2023, challenging U.S. Pat. No. 8,254,591.
Patent Owner's Notice of Appeal, Exhibit—38, Filed on Aug. 15, 2023, challenging U.S. Pat. No. 8,111,839.
Patent Owner's Notice of Appeal; Exhibit—31, Filed on Aug. 11, 2023, challenging U.S. Pat. No. 9,124,982.
Patent Owner's Notice of Cross-Appeal, Exhibit—39, Filed on Aug. 23, 2023, challenging U.S. Pat. No. 9,609,424.
Patent Owner's Power of Attorney, Exhibit—4, Filed on Jan. 19, 2022, challenging U.S. Pat. No. 10,966,015.
Patent Owner's Power of Attorney, Exhibit—4, Filed on Jan. 19, 2022, challenging U.S. Pat. No. 10,979,836.
Patent Owner's Power of Attorney, Exhibit—4, Filed on Dec. 28, 2021, challenging U.S. Pat. No. 9,491,542.
Patent Owner's Power of Attorney, Exhibit—4, Filed on Dec. 28, 2021, challenging U.S. Pat. No. 9,270,244.
Patent Owner's Power of Attorney, Exhibit—4, Filed on Dec, 28, 2021, challenging U.S. Pat. No. 9,609,424.
Patent Owner's Power of Attorney, Exhibit—4, Filed on Dec. 28, 2021, challenging U.S. Pat. No. 8,254,591.
Patent Owner's Power of Attorney, Exhibit—4, Filed on Jun. 22, 2022, challenging U.S. Pat. No. 11,057,701.
Patent Owner's Power of Attorney, Exhibit—4, Filed on Jun. 22, 2022, challenging U.S. Pat. No. 11,244,666.
Patent Owner's Power of Attorney, Exhibit—4, Filed on Jun. 22, 2022, challenging U.S. Pat. No. 11,039,259.
Patent Owner's Power of Attorney, Exhibit—5, Filed on Jan. 19, 2022, challenging U.S. Pat. No. 10,405,082.
Patent Owner's Power of Attorney, Exhibit—5, Filed on Jun. 22, 2022, challenging U.S. Pat. No. 11,217,237.
Patent Owner's Power of Attorney, Exhibit—6, Filed on Dec. 28, 2021, challenging U.S. Pat. No. 8,111,839.
Patent Owner's Power of Attorney, Exhibit—6, Filed on Dec. 28, 2021, challenging U.S. Pat. No. 8,315,400.
Patent Owner's Power of Attorney; Exhibit—5, Filed on Dec. 28, 2021, challenging U.S. Pat. No. 9,124,982.
Patent Owner's Preliminary Response, Exhibit—12, Filed on Mar. 23, 2022, challenging U.S. Pat. No. 8,111,839.
Patent Owner's Preliminary Response, Exhibit—13, Filed on Mar. 23, 2022, challenging U.S. Pat. No. 8,111,839.
Patent Owner's Preliminary Response, Exhibit—7, Filed on Oct. 11, 2022, challenging U.S. Pat. No. 11,039,259.
Patent Owner's Preliminary Response, Exhibit—7, Filed on Oct. 7, 2022, challenging U.S. Pat. No. 11,057,701.
Patent Owner's Preliminary Response, Exhibit—7, Filed on Oct. 7, 2022, challenging U.S. Pat. No. 11,244,666.
Patent Owner's Preliminary Response, Exhibit—7, Filed on May 18, 2022, challenging U.S. Pat. No. 10,979,836.
Patent Owner's Preliminary Response, Exhibit—8, Filed on Oct. 7, 2022, challenging U.S. Pat. No. 11,217,237.
Patent Owner's Preliminary Response, Exhibit—8, Filed on Apr. 13, 2022, challenging U.S. Pat. No. 9,609,424.
Patent Owner's Preliminary Response, Exhibit—8, Filed on Apr. 13, 2022, challenging U.S. Pat. No. 8,254,591.
Patent Owner's Preliminary Response, Exhibit—8, Filed on Apr. 18, 2022, challenging U.S. Pat. No. 9,491,542.
Patent Owner's Preliminary Response, Exhibit—8, Filed on Apr. 18, 2022, challenging U.S. Pat. No. 9,270,244.
Patent Owner's Preliminary Response, Exhibit—8, Filed on May 18, 2022, challenging U.S. Pat. No. 10,966,015.
Patent Owner's Preliminary Response, Exhibit—9, Filed on Mar. 21, 2022, challenging U.S. Pat. No. 8,315,400.
Patent Owner's Preliminary Response, Exhibit—9, Filed on May 18, 2022, challenging U.S. Pat. No. 10,405,082.
Patent Owner's Preliminary Response; Exhibit—9, Filed on Mar. 21, 2022, challenging U.S. Pat. No. 9,124,982.
Patent Owner's Preliminary Sur-Reply, Exhibit—10, Filed on Nov. 22, 2022, challenging U.S. Pat. No. 11,217,237.
Patent Owner's Preliminary Sur-Reply, Exhibit—10, Filed on May 19, 2022, challenging U.S. Pat. No. 9,609,424.
Patent Owner's Preliminary Sur-Reply, Exhibit—10, Filed on May 20, 2022, challenging U.S. Pat. No. 8,254,591.
Patent Owner's Preliminary Sur-Reply, Exhibit—10, Filed on May 31, 2022, challenging U.S. Pat. No. 9,491,542.

(56) References Cited

OTHER PUBLICATIONS

Patent Owner's Preliminary Sur-Reply, Exhibit—10, Filed on Jun. 23, 2022, challenging U.S. Pat. No. 10,966,015.
Patent Owner's Preliminary Sur-Reply, Exhibit—10, Filed on Jun. 7, 2022, challenging U.S. Pat. No. 9,270,244.
Patent Owner's Preliminary Sur-Reply, Exhibit—11, Filed on Apr. 29, 2022, challenging U.S. Pat. No. 8,315,400.
Patent Owner's Preliminary Sur-Reply, Exhibit—11, Filed on Jun. 23, 2022, challenging U.S. Pat. No. 10,405,082.
Patent Owner's Preliminary Sur-Reply, Exhibit—14, Filed on Apr. 29, 2022, challenging U.S. Pat. No. 8,111,839.
Patent Owner's Preliminary Sur-Reply, Exhibit—15, Filed on Apr. 29, 2022, challenging U.S. Pat. No. 8,111,839.
Patent Owner's Preliminary Sur-Reply, Exhibit—9, Filed on Nov. 17, 2022, challenging U.S. Pat. No. 11,244,666.
Patent Owner's Preliminary Sur-Reply, Exhibit—9, Filed on Nov. 18, 2022, challenging U.S. Pat. No. 11,057,701.
Patent Owner's Preliminary Sur-Reply, Exhibit—9, Filed on Nov. 18, 2022, challenging U.S. Pat. No. 11,039,259.
Patent Owner's Preliminary Sur-Reply, Exhibit—9, Filed on Jun. 23, 2022, challenging U.S. Pat. No. 10,979,836.
Patent Owner's Preliminary Sur-Reply; Exhibit—11, Filed on Apr. 29, 2022, challenging U.S. Pat. No. 9,124,982.
Patent Owner's Request for Oral Argument, Exhibit—21, Filed on Feb. 3, 2023, challenging U.S. Pat. No. 8,315,400.
Patent Owner's Request for Oral Argument, Exhibit—21, Filed on Aug. 17, 2023, challenging U.S. Pat. No. 11,057,701.
Patent Owner's Request for Oral Argument, Exhibit—22, Filed on Feb. 28, 2023, challenging U.S. Pat. No. 9,609,424.
Patent Owner's Request for Oral Argument, Exhibit—23, Filed on Mar. 1, 2023, challenging U.S. Pat. No. 9,270,244.
Patent Owner's Request for Oral Argument, Exhibit—24, Filed on Feb. 28, 2023, challenging U.S. Pat. No. 8,254,591.
Patent Owner's Request for Oral Argument, Exhibit—24, Filed on Mar. 1, 2023, challenging U.S. Pat. No. 9,491,542.
Patent Owner's Request for Oral Argument, Exhibit—24, Filed on Apr. 4, 2023, challenging U.S. Pat. No. 10,966,015.
Patent Owner's Request for Oral Argument, Exhibit—25, Filed on Apr. 4, 2023, challenging U.S. Pat. No. 10,405,082.
Patent Owner's Request for Oral Argument, Exhibit—25, Filed on Aug. 28, 2023, challenging U.S. Pat. No. 11,039,259.
Patent Owner's Request for Oral Argument, Exhibit—26, Filed on Feb. 7, 2023, challenging U.S. Pat. No. 8,111,839.
Patent Owner's Request for Oral Argument, Exhibit—27, Filed on Feb. 7, 2023, challenging U.S. Pat. No. 8,111,839.
Patent Owner's Request for Oral Argument; Exhibit—22, Filed on Feb. 3, 2023, challenging U.S. Pat. No. 9,124,982.
Patent Owner's Response, Exhibit—14, Filed on Mar. 23, 2023, challenging U.S. Pat. No. 11,057,701.
Patent Owner's Response, Exhibit—15, Filed on Sep. 9, 2022, challenging U.S. Pat. No. 8,315,400.
Patent Owner's Response, Exhibit—16, Filed on Dec. 6, 2024, challenging U.S. Pat. No. 11,610,587.
Patent Owner's Response, Exhibit—17, Filed on Apr. 10, 2023, challenging U.S. Pat. No. 11,039,259.
Patent Owner's Response, Exhibit—18, Filed on Oct. 17, 2022, challenging U.S. Pat. No. 9,609,424.
Patent Owner's Response, Exhibit—18, Filed on Nov. 8, 2022, challenging U.S. Pat. No. 10,966,015.
Patent Owner's Response, Exhibit—19, Filed on Oct. 19, 2022, challenging U.S. Pat. No. 9,491,542.
Patent Owner's Response, Exhibit—19, Filed on Oct. 19, 2022, challenging U.S. Pat. No. 9,270,244.
Patent Owner's Response, Exhibit—19, Filed on Nov. 8, 2022, challenging U.S. Pat. No. 10,405,082.
Patent Owner's Response, Exhibit—20, Filed on Oct. 17, 2022, challenging U.S. Pat. No. 8,254,591.
Patent Owner's Response, Exhibit—21, Filed on Sep. 13, 2022, challenging U.S. Pat. No. 8,111,839.
Patent Owner's Response, Exhibit—22, Filed on Sep. 13, 2022, challenging U.S. Pat. No. 8,111,839.
Patent Owner's Sur-Reply, Exhibit—19, Filed on Jan. 12, 2023, challenging U.S. Pat. No. 8,315,400.
Patent Owner's Sur-Reply, Exhibit—19, Filed on Jul. 26, 2023, challenging U.S. Pat. No. 11,057,701.
Patent Owner's Sur-Reply, Exhibit—21, Filed on Feb. 21, 2023, challenging U.S. Pat. No. 9,609,424.
Patent Owner's Sur-Reply, Exhibit—22, Filed on Feb. 22, 2023, challenging U.S. Pat. No. 9,270,244.
Patent Owner's Sur-Reply, Exhibit—22, Filed on Mar. 13, 2023, challenging U.S. Pat. No. 10,966,015.
Patent Owner's Sur-Reply, Exhibit—23, Filed on Feb. 20, 2023, challenging U.S. Pat. No. 8,254,591.
Patent Owner's Sur-Reply, Exhibit—23, Filed on Feb. 22, 2023, challenging U.S. Pat. No. 9,491,542.
Patent Owner's Sur-Reply, Exhibit—23, Filed on Mar. 13, 2023, challenging U.S. Pat. No. 10,405,082.
Patent Owner's Sur-Reply, Exhibit—23, Filed on Aug. 14, 2023, challenging U.S. Pat. No. 11,039,259.
Patent Owner's Sur-Reply, Exhibit—25, Filed on Jan. 17, 2023, challenging U.S. Pat. No. 8,111,839.
Patent Owner's Sur-Reply, Exhibit—26, Filed on Jan. 12, 2023, challenging U.S. Pat. No. 8,111,839.
Patent Owner's Sur-Reply; Exhibit—21, Filed on Jan. 13, 2023, challenging U.S. Pat. No. 9,124,982.
Patent Owner's Unopposed Motion To Withdraw and Substitute Counsel Under 37 CFR 11.116, Exhibit—11, Filed on Nov. 13, 2024, challenging U.S. Pat. No. 11,610,587.
Patent Owner's Unopposed Motion to Withdraw and Substitute Counsel Under 37 CFR 11.116, Exhibit - 11, Filed on Nov. 21, 2024, challenging U.S. Pat. No. 9,191,083.
Patent Owner's Unopposed Motion To Withdraw and Substitute Counsel Under 37 CFR 11.116, Exhibit—11, Filed on Nov. 21, 2024, challenging U.S. Pat. No. 9,614,943.
Patent Owner's Unopposed Motion To Withdraw and Substitute Counsel Under 37 CFR 11.116, Exhibit—11, Filed on Nov. 21, 2024, challenging U.S. Pat. No. 7,049,850.
Patent Owner's Unopposed Motion To Withdraw and Substitute Counsel Under 37 CFR 11.116, Exhibit—12, Filed on Nov. 21, 2024, challenging U.S. Pat. No. 9,279,263.
Patent Owner's Unopposed Motion To Withdraw and Substitute Counsel Under 37 CFR 11.116Paper10, Nov. 21, 2024, challenging U.S. Pat. No. 8,434,966.
Patent Owner's Updated Exhibit List, Exhibit—23, Filed on Sep. 25, 2023, challenging U.S. Pat. No. 11,057,701.
Patent Owner's Updated Mandatory Notice under 37 C.F.R. 42.8, Exhibit—15, Filed on Jul. 27, 2022, challenging U.S. Pat. No. 8,254,591.
Patent Owner's Updated Mandatory Notice under 37 C.F.R. 42.8, Exhibit—17, Filed on Jul. 27, 2022, challenging U.S. Pat. No. 8,111,839.
Patent Owner's Updated Mandatory Notice under 37 C.F.R. 42.8, Exhibit—18, Filed on Jul. 27, 2022, challenging U.S. Pat. No. 8,111,839.
Patent Owner's Updated Mandatory Notice under 37 C.F.R. 42.8, Exhibit—8, Filed on Dec. 28, 2021, challenging U.S. Pat. No. 8,111,839.
Patent Owner's Updated Mandatory Notice under 37 C.F.R. 42.8; Exhibit—14, Filed on Jul. 27, 2022, challenging U.S. Pat. No. 9,124,982.
Patent Owner's Updated Mandatory Notice under 37 C.F.R. 42.8; Exhibit—7, Filed on Dec. 28, 2021, challenging U.S. Pat. No. 9,124,982.
Patent Owner's Updated Mandatory Notice, Exhibit—17, Filed on Sep. 13, 2022, challenging U.S. Pat. No. 9,491,542.
Patent Owner's Updated Mandatory Notice, Exhibit—17, Filed on Sep. 13, 2022, challenging U.S. Pat. No. 9,270,244.
Patent Owner's Updated Mandatory Notice, Exhibit—18, Filed on Jun. 28, 2023, challenging U.S. Pat No. 11,057,701.
Patent Owner's Updated Mandatory Notice, Exhibit—20, Filed on Jun. 28, 2023, challenging U.S. Pat. No. 11,039,259.

(56) References Cited

OTHER PUBLICATIONS

Patent Owner's Updated Mandatory Notice, Exhibit—29, Filed on Jun. 28, 2023, challenging U.S. Pat. No. 8,315,400.
Patent Owner's Updated Mandatory Notice, Exhibit—29, Filed on Jun. 28, 2023, challenging U.S. Pat. No. 10,966,015.
Patent Owner's Updated Mandatory Notice, Exhibit—30, Filed on Jun. 28, 2023, challenging U.S. Pat. No. 9,270,244.
Patent Owner's Updated Mandatory Notice, Exhibit—30, Filed on Jun. 28, 2023, challenging U.S. Pat. No. 10,405,082.
Patent Owner's Updated Mandatory Notice, Exhibit—31, Filed on Jun. 28, 2023, challenging U.S. Pat. No. 9,491,542.
Patent Owner's Updated Mandatory Notice, Exhibit—31, Filed on Jun. 28, 2023, challenging U.S. Pat. No. 8,254,591.
Patent Owner's Updated Mandatory Notice, Exhibit—35, Filed on Jun. 28, 2023, challenging U.S. Pat. No. 9,609,424.
Patent Owner's Updated Mandatory Notice, Exhibit—36, Filed on Jun. 28, 2023, challenging U.S. Pat. No. 8,111,839.
Patent Owner's Updated Mandatory Notice, Exhibit—37, Filed on Jun. 28, 2023, challenging U.S. Pat. No. 8,111,839.
Patent Owner's Updated Mandatory Notice; Exhibit—30, Filed on Jun. 28, 2023, challenging U.S. Pat. No. 9,124,982.
Patent Owner's Updated Mandatory Notices, Exhibit—15, Filed on Dec. 6, 2024, challenging U.S. Pat. No. 11,610,587.
Patent Owner's Updated Power of Attorney Pursuant to 37 CFR 41.10(b), Exhibit—14, Filed on Dec. 6, 2024, challenging U.S. Pat. No. 11,610,587.
Petition : as filed for Inter Partes Review of U.S. Pat. No. 11,610,587, Exhibit—4, Filed on Feb. 9, 2024, challenging U.S. Pat. No. 11,610,587.
Petition : as filed, Exhibit—3, Filed on Jun. 12, 2024, challenging U.S. Pat. No. 9,191,083.
Petition : as filed, Exhibit—3, Filed on Jun. 12, 2024, challenging U.S. Pat. No. 9,614,943.
Petition : as filed, Exhibit—4, Filed on Jun. 25, 2024, challenging U.S. Pat. No. 7,049,850.
Petition : as filed, Exhibit—5, Filed on Jul. 1, 2024, challenging U.S. Pat. No. 9,279,263.
Petition : as filedPaper3,Jun. 18, 2024, challenging U.S. Pat. No. 8,434, 966.
Petition for Inter Partes Review of U.S. Pat. No. 11,217,237, Exhibit—4, Filed on Jun. 9, 2022, challenging U.S. Pat. No. 11,217,237.
Petition for Inter Partes Review of U.S. Pat. No. 11,244,666, Exhibit—3, Filed on Jun. 9, 2022, challenging U.S. Pat. No. 11,244,666.
Petition for Inter Partes Review of U.S. Pat. No. 8,254,591, Exhibit—3, Filed on Dec. 20, 2021, challenging U.S. Pat. No. 8,254,591.
Petition for Inter Partes Review of U.S. Pat. No. 10,405,082, Exhibit—3, Filed on Dec. 20, 2021, challenging U.S. Pat. No. 10,405,082.
Petition for Inter Partes Review of U.S. Pat. No. 10,966,015, Exhibit—3, Filed on Jan. 4, 2022, challenging U.S. Pat. No. 10,966,015.
Petition for Inter Partes Review of U.S. Pat. No. 10,979,836, Exhibit—3, Filed on Jan. 14, 2022, challenging U.S. Pat. No. 10,979,836.
Petition for Inter Partes Review of U.S. Pat. No. 11,039,259, Exhibit—3, Filed on Jan. 9, 2022, challenging U.S. Pat. No. 11,039,259.
Petition for Inter Partes Review of U.S. Pat. No. 8,111,839, Exhibit—3, Filed on Dec. 13, 2021, challenging U.S. Pat. No. 8,111,839.
Petition for Inter Partes Review of U.S. Pat. No. 9,124,982; Exhibit—3, Filed on Dec. 13, 2021, challenging U.S. Pat. No. 9,124,982.
Petition for Inter Partes Review of U.S. Pat. No. 9,270,244, Exhibit—3, Filed on Dec. 21, 2021, challenging U.S. Pat. No. 9,270,244.
Petition for Inter Partes Review of U.S. Pat. No. 9,491,542, Exhibit—3, Filed on Dec. 17, 2021, challenging U.S. Pat. No. 9,491,542.
Petition for Inter Partes Review of U.S. Pat. No. 9,609,424, Exhibit—3, Filed on Dec. 21, 2021, challenging U.S. Pat. No. 9,609,424.
Petition of Inter Partes Review of U.S. Pat. No. 11,057,701, Exhibit—3, Filed on Jun. 9, 2022, challenging U.S. Pat. No. 11,057,701.
Petition with Proposed Corrections in Redline, Exhibit—1042, Filed on Jan. 31, 2022, challenging U.S. Pat. No. 8,111,839.
Petitioner's Power of Attorney from Samsung Electronics Co., Ltd.; Exhibit—1, Filed on Dec. 13, 2021, challenging U.S. Pat. No. 9,124,982.
Petitioner's Power of Attorney from Samsung Electronics, America, Inc.; Exhibit—2, Filed on Dec. 13, 2021, challenging U.S. Pat. No. 9,124,982.
Petitioner's Updated Mandatory Notices, Exhibit—16, Filed on Oct. 10, 2022, challenging U.S. Pat. No. 10,966,015.
Petitioner's Updated Mandatory Notices, Exhibit—17, Filed on Oct. 10, 2022, challenging U.S. Pat. No. 10,405,082.
Petitioner's Updated Mandatory Notices; Exhibit—27, Filed on Apr. 3, 2023, challenging U.S. Pat. No. 9,124,982.
Petitioners Supplemental Brief on Interim Fintiv Guidance, Exhibit—10, Filed on Jul. 1, 2022, challenging U.S. Pat. No. 10,979,836.
Petitioners Supplemental Brief on Interim Fintiv Guidance, Exhibit—11, Filed on Jul. 1, 2022, challenging U.S. Pat. No. 9,491,542.
Petitioners Supplemental Brief on Interim Fintiv Guidance, Exhibit—11, Filed on Jul. 1, 2022, challenging U.S. Pat. No. 9,270,244.
Petitioners Supplemental Brief on Interim Fintiv Guidance, Exhibit—11, Filed on Jul. 1, 2022, challenging U.S. Pat. No. 9,609,424.
Petitioners Supplemental Brief on Interim Fintiv Guidance, Exhibit—11, Filed on Jul. 1, 2022, challenging U.S. Pat. No. 8,254,591.
Petitioners Supplemental Brief on Interim Fintiv Guidance, Exhibit—11, Filed on Jul. 1, 2022, challenging U.S. Pat. No. 10,966,015.
Petitioners Supplemental Brief on Interim Fintiv Guidance, Exhibit—12, Filed on Jul. 1, 2022, challenging U.S. Pat. No. 10,405,082.
Petitioners' Demonstrative Exhibits for Oral Argument, Exhibit—1019, Filed on Mar. 14, 2023, challenging U.S. Pat. No. 8,315,400.
Petitioners' Demonstrative Exhibits for Oral Argument; Exhibit—1045, Filed on Mar. 14, 2023, challenging U.S. Pat. No. 9,124,982.
Petitioners' Motion for Leave to File Corrected Petition, Exhibit—9, Filed on Jan. 31, 2022, challenging U.S. Pat. No. 8,111,839.
Petitioners' Motion to Submit Supplemental Information Pursuant to 37 C.F.R. §42.123(b), Exhibit—29, Filed on Apr. 13, 2023, challenging U.S. Pat. No. 9,609,424.
Petitioners' Notice of Appeal, Exhibit—31, Filed on Aug. 11, 2023, challenging U.S. Pat. No. 8,315,400.
Petitioners' Notice of Appeal, Exhibit—38, Filed on Aug. 11, 2023, challenging U.S. Pat. No. 9,609,424.
Petitioners' Notice of Cross-Appeal, Exhibit—34, Filed on Sep. 20, 2023, challenging U.S. Pat. No. 9,270,244.
Petitioners' Notice of Cross-Appeal, Exhibit—35, Filed on Sep. 20, 2023, challenging U.S. Pat. No. 9,491,542.
Petitioners' Notice of Cross-Appeal, Exhibit—35, Filed on Sep. 20, 2023, challenging U.S. Pat. No. 8,254,591.
Petitioners' Notice of Cross-Appeal, Exhibit—39, Filed on Aug. 24, 2023, challenging U.S. Pat. No. 8,111,839.
Petitioners' Notice of Cross-Appeal; Exhibit—32, Filed on Aug. 24, 2023, challenging U.S. Pat. No. 9,124,982.
Petitioners' Notice of Depo of Chrisotpher Struck, Exhibit—16, Filed on May 15, 2023, challenging U.S. Pat. No. 11,057,701.
Petitioners' Notice of Deposition of Christopher Struck, Exhibit—19, Filed on Nov. 15, 2022, challenging U.S. Pat. No. 9,609,424.
Petitioners' Notice of Deposition of Daniel P. Anagnos, Exhibit—23, Filed on Nov. 9, 2022, challenging U.S. Pat. No. 8,111,839.
Petitioners' Notice of Deposition of Daniel P. Anagnos, Exhibit—24, Filed on Nov. 9, 2022, challenging U.S. Pat. No. 8,111,839.
Petitioners' Notice of Deposition of Daniel P. Anagnos; Exhibit—19, Filed on Nov. 9, 2022, challenging U.S. Pat. No. 9,124,982.
Petitioners' Notice of Deposition of David Kleinschmidt, Exhibit—19, Filed on May 24, 2023, challenging U.S. Pat. No. 11,039,259.
Petitioners' Notice of Objections to Evidence, Exhibit—18, Filed on Apr. 19, 2023, challenging U.S. Pat. No. 11,039,259.
Petitioners' Notice of Objections to Evidence, Exhibit—22, Filed on Sep. 20, 2022, challenging U.S. Pat. No. 8,111,839.
Petitioners' Notice of Objections to Evidence, Exhibit—23, Filed on Sep. 20, 2022, challenging U.S. Pat. No. 8,111,839.

(56) References Cited

OTHER PUBLICATIONS

Petitioners' Notice of Objections to Evidence; Exhibit—18, Filed on Sep. 16, 2022, challenging U.S. Pat. No. 9,124,982.
Petitioners' Preliminary Reply, Exhibit—10, Filed on Apr. 20, 2022, challenging U.S. Pat. No. 8,315,400.
Petitioners' Preliminary Reply, Exhibit—10, Filed on Jun. 14, 2022, challenging U.S. Pat. No. 10,405,082.
Petitioners' Preliminary Reply, Exhibit—13, Filed on Apr. 20, 2022, challenging U.S. Pat. No. 8,111,839.
Petitioners' Preliminary Reply, Exhibit—14, Filed on Apr. 20, 2022, challenging U.S. Pat. No. 8,111,839.
Petitioners' Preliminary Reply, Exhibit—8, Filed on Nov. 10, 2022, challenging U.S. Pat. No. 11,057,701.
Petitioners' Preliminary Reply, Exhibit—8, Filed on Nov. 10, 2022, challenging U.S. Pat. No. 11,244,666.
Petitioners' Preliminary Reply, Exhibit—8, Filed on Nov. 10, 2022, challenging U.S. Pat. No. 11,039,259.
Petitioners' Preliminary Reply, Exhibit—8, Filed on Jun. 14, 2022, challenging U.S. Pat. No. 10,979,836.
Petitioners' Preliminary Reply, Exhibit—9, Filed on Nov. 15, 2022, challenging U.S. Pat. No. 11,217,237.
Petitioners' Preliminary Reply, Exhibit—9, Filed on May 10, 2022, challenging U.S. Pat. No. 9,609,424.
Petitioners' Preliminary Reply, Exhibit—9, Filed on May 11, 2022, challenging U.S. Pat. No. 8,254,591.
Petitioners' Preliminary Reply, Exhibit—9, Filed on May 20, 2022, challenging U.S. Pat. No. 9,491,542.
Petitioners' Preliminary Reply, Exhibit—9, Filed on May 27, 2022, challenging U.S. Pat. No. 9,270,244.
Petitioners' Preliminary Reply, Exhibit—9, Filed on Jun. 14, 2022, challenging U.S. Pat. No. 10,966,015.
Petitioners' Preliminary Reply; Exhibit—10, Filed on Apr. 20, 2022, challenging U.S. Pat. No. 9,124,982.
Petitioners' Reply to Patent Owner's Response, Exhibit—17, Filed on Dec. 2, 2022, challenging U.S. Pat. No. 8,315,400.
Petitioners' Reply to Patent Owner's Response, Exhibit—17, Filed on Jun. 15, 2023, challenging U.S. Pat. No. 11,057,701.
Petitioners' Reply to Patent Owner's Response, Exhibit—20, Filed on Jan. 10, 2023, challenging U.S. Pat. No. 9,609,424.
Petitioners' Reply to Patent Owner's Response, Exhibit—20, Filed on Jan. 31, 2023, challenging U.S. Pat. No. 10,966,015.
Petitioners' Reply to Patent Owner's Response, Exhibit—21, Filed on Jan. 11, 2023, challenging U.S. Pat. No. 9,270,244.
Petitioners' Reply to Patent Owner's Response, Exhibit—21, Filed on Jan. 31, 2023, challenging U.S. Pat. No. 10,405,082.
Petitioners' Reply to Patent Owner's Response, Exhibit—21, Filed on Jun. 30, 2023, challenging U.S. Pat. No. 11,039,259.
Petitioners' Reply to Patent Owner's Response, Exhibit—22, Filed on Jan. 10, 2023, challenging U.S. Pat. No. 8,254,591.
Petitioners' Reply to Patent Owner's Response, Exhibit—24, Filed on Dec. 6, 2022, challenging U.S. Pat. No. 8,111,839.
Petitioners' Reply to Patent Owner's Response, Exhibit—25, Filed on Dec. 6, 2022, challenging U.S. Pat. No. 8,111,839.
Petitioners' Reply to Patent Owner's Response, Exhibit—20, Filed on Dec. 2, 2022, challenging U.S. Pat. No. 9,124,982.
Petitioners' Reply to Patent Owners Response, Exhibit—21, Filed on Jan. 11, 2023, challenging U.S. Pat. No. 9,491,542.
Petitioners' Request for Oral Argument, Exhibit—20, Filed on Aug. 17, 2023, challenging U.S. Pat. No. 11,057,701.
Petitioners' Request for Oral Argument, Exhibit—22, Filed on Feb. 3, 2023, challenging U.S. Pat. No. 8,315,400.
Petitioners' Request for Oral Argument, Exhibit—23, Filed on Feb. 28, 2023, challenging U.S. Pat. No. 9,609,424.
Petitioners' Request for Oral Argument, Exhibit—24, Filed on Mar. 1, 2023, challenging U.S. Pat. No. 9,270,244.
Petitioners' Request for Oral Argument, Exhibit—24, Filed on Aug. 8, 2023, challenging U.S. Pat. No. 11,039,259.
Petitioners' Request for Oral Argument, Exhibit—25, Filed on Feb. 28, 2023, challenging U.S. Pat. No. 8,254,591.
Petitioners' Request for Oral Argument, Exhibit—25, Filed on Mar. 1, 2023, challenging U.S. Pat. No. 9,491,542.
Petitioners' Request for Oral Argument, Exhibit—25, Filed on Apr. 4, 2023, challenging U.S. Pat. No. 10,966,015.
Petitioners' Request for Oral Argument, Exhibit—26, Filed on Apr. 4, 2023, challenging U.S. Pat. No. 10,405,082.
Petitioners' Request for Oral Argument, Exhibit—27, Filed on Feb. 7, 2023, challenging U.S. Pat. No. 8,111,839.
Petitioners' Request for Oral Argument, Exhibit—28, Filed on Feb. 7, 2023, challenging U.S. Pat. No. 8,111,839.
Petitioners' Request for Oral Argument; Exhibit—23, Filed on Feb. 3, 2023, challenging U.S. Pat. No. 9,124,982.
Petitioners' Request for Refund of Post-Institution Fee, Exhibit—12, Filed on Mar. 2, 2023, challenging U.S. Pat. No. 11,244,666.
Petitioners' Request for Refund of Post-Institution Fee, Exhibit—13, Filed on Jan. 18, 2023, challenging U.S. Pat. No. 10,979,836.
Petitioners' Request for Refund of Post-Institution Fee, Exhibit—13, Filed on Mar. 2, 2023, challenging U.S. Pat. No. 11,217,237.
Petitioners' Request for Refund of Post-Institution Fees, Exhibit—17, Filed on Dec. 16, 2024, challenging U.S. Pat. No. 9,191,083.
Petitioners' Request for Refund of Post-Institution Fees, Exhibit—17, Filed on Dec. 16, 2024, challenging U.S. Pat. No. 9,614,943.
Petitioners' Request for Refund of Post-Institution Fees, Exhibit—17, Filed on Dec. 16, 2024, challenging U.S. Pat. No. 7,049,850.
Petitioners' Request for Refund of Post-Institution Fees, Exhibit—18, Filed on Dec. 16, 2024, challenging U.S. Pat. No. 9,279,263.
Petitioners' Request for Refund of Post-Institution FeesPaper16, Dec. 16, 2024, challenging U.S. Pat. No. 8,434,966.
Petitioners' Submission of Supplemental Information, Exhibit—33, Filed on May 15, 2023, challenging U.S. Pat. No. 9,609,424.
Petitioners' Sur-Sur-Reply to Patent Owner's Sur-Reply, Exhibit—20, Filed on Jan. 27, 2023, challenging U.S. Pat. No. 8,315,400.
Petitioners' Sur-Sur-Reply to Patent Owner's Sur-Reply, Exhibit—26, Filed on Mar. 7, 2023, challenging U.S. Pat. No. 9,270,244.
Petitioners' Sur-Sur-Reply to Patent Owner's Sur-Reply, Exhibit—27, Filed on Mar. 7, 2023, challenging U.S. Pat. No. 9,491,542.
Petitioners' Updated Exhibit List, Exhibit—10, Filed on Nov. 20, 2024, challenging U.S. Pat. No. 9,191,083.
Petitioners' Updated Exhibit List, Exhibit—10, Filed on Nov. 20, 2024, challenging U.S. Pat. No. 9,614,943.
Petitioners' Updated Exhibit List, Exhibit—10, Filed on Nov. 20, 2024, challenging U.S. Pat. No. 7,049,850.
Petitioners' Updated Exhibit List, Exhibit—11, Filed on Nov. 20, 2024, challenging U.S. Pat. No. 9,279,263.
Petitioners' Updated Exhibit List, Exhibit—15, Filed on Dec. 11, 2024, challenging U.S. Pat. No. 9,191,083.
Petitioners' Updated Exhibit List, Exhibit—15, Filed on Dec. 11, 2024, challenging U.S. Pat. No. 9,614,943.
Petitioners' Updated Exhibit List, Exhibit—15, Filed on Dec. 11, 2024, challenging U.S. Pat. No. 7,049,850.
Petitioners' Updated Exhibit List, Exhibit—16, Filed on Dec. 11, 2024, challenging U.S. Pat. No. 9,279,263.
Petitioners' Updated Exhibit List, Exhibit—19, Filed on Dec. 11, 2024, challenging U.S. Pat. No. 11,610,587.
Petitioners' Updated Exhibit List, Exhibit—24, Filed on Dec. 11, 2023, challenging U.S. Pat. No. 8,315,400.
Petitioners' Updated Exhibit List, Exhibit—24, Filed on Sep. 26, 2023, challenging U.S. Pat. No. 11,057,701.
Petitioners' Updated Exhibit List, Exhibit—27, Filed on May 9, 2023, challenging U.S. Pat. No. 10,966,015.
Petitioners' Updated Exhibit List, Exhibit—28, Filed on Oct. 11, 2023, challenging U.S. Pat. No. 11,039,259.
Petitioners' Updated Exhibit List, Exhibit—28, Filed on Apr. 11, 2023, challenging U.S. Pat. No. 9,609,424.
Petitioners' Updated Exhibit List, Exhibit—28, Filed on Apr. 13, 2023, challenging U.S. Pat. No. 9,270,244.
Petitioners' Updated Exhibit List, Exhibit—28, Filed on May 9, 2023, challenging U.S. Pat. No. 10,405,082.
Petitioners' Updated Exhibit List, Exhibit—30, Filed on Apr. 12, 2023, challenging U.S. Pat. No. 9,491,542.
Petitioners' Updated Exhibit List, Exhibit—30, Filed on Apr. 13, 2023, challenging U.S. Pat. No. 9,609,424.

(56) References Cited

OTHER PUBLICATIONS

Petitioners' Updated Exhibit List, Exhibit—30, Filed on Apr. 4, 2023, challenging U.S. Pat. No. 8,254,591.
Petitioners' Updated Exhibit List, Exhibit—31, Filed on Mar. 16, 2023, challenging U.S. Pat. No. 8,111,839.
Petitioners' Updated Exhibit List, Exhibit—31, Filed on Apr. 13, 2023, challenging U.S. Pat. No. 9,609,424.
Petitioners' Updated Exhibit List, Exhibit—32, Filed on Mar. 16, 2023, challenging U.S. Pat. No. 8,111,839.
Petitioners' Updated Exhibit List; Exhibit—25, Filed on Mar. 14, 2023, challenging U.S. Pat. No. 9,124,982.
Petitioners' Updated Exhibit ListPaper14, Dec. 11, 2024, challenging U.S. Pat. No. 8,434,966.
Petitioners' Updated Exhibit ListPaper9, Nov. 20, 2024, challenging U.S. Pat. No. 8,434,966.
Petitioners' Updated Mandatory Notices, Exhibit—15, Filed on Apr. 3, 2023, challenging U.S. Pat. No. 11,057,701.
Petitioners' Updated Mandatory Notices, Exhibit—16, Filed on Mar. 28, 2023, challenging U.S. Pat. No. 11,039,259.
Petitioners' Updated Mandatory Notices, Exhibit—18, Filed on Aug. 10, 2022, challenging U.S. Pat. No. 8,254,591.
Petitioners' Updated Mandatory Notices, Exhibit—20, Filed on Aug. 10, 2022, challenging U.S. Pat. No. 8,111,839.
Petitioners' Updated Mandatory Notices, Exhibit—21, Filed on Feb. 8, 2023, challenging U.S. Pat. No. 10,966,015.
Petitioners' Updated Mandatory Notices, Exhibit—21, Filed on Aug. 10, 2022, challenging U.S. Pat. No. 8,111,839.
Petitioners' Updated Mandatory Notices, Exhibit—22, Filed on Feb. 8, 2023, challenging U.S. Pat. No. 10,405,082.
Petitioners' Updated Mandatory Notices, Exhibit—23, Filed on Apr. 3, 2023, challenging U.S. Pat. No. 10,966,015.
Petitioners' Updated Mandatory Notices, Exhibit—24, Filed on Apr. 3, 2023, challenging U.S. Pat. No. 10,405,082.
Petitioners' Updated Mandatory Notices, Exhibit—26, Filed on Apr. 3, 2023, challenging U.S. Pat. No. 8,315,400.
Petitioners' Updated Mandatory Notices, Exhibit—26, Filed on Apr. 3, 2023, challenging U.S. Pat. No. 9,609,424.
Petitioners' Updated Mandatory Notices, Exhibit—27, Filed on Apr. 3, 2023, challenging U.S. Pat. No. 9,270,244.
Petitioners' Updated Mandatory Notices, Exhibit—28, Filed on Apr. 3, 2023, challenging U.S. Pat. No. 9,491,542.
Petitioners' Updated Mandatory Notices, Exhibit—28, Filed on Apr. 3, 2023, challenging U.S. Pat. No. 8,254,591.
Petitioners' Updated Mandatory Notices, Exhibit—33, Filed on Apr. 3, 2023, challenging U.S. Pat. No. 8,111,839.
Petitioners' Updated Mandatory Notices, Exhibit—34, Filed on Apr. 3, 2023, challenging U.S. Pat. No. 8,111,839.
Petitioners' Updated Mandatory Notices, Exhibit—4, Filed on Jan. 6, 2022, challenging U.S. Pat. No. 10,405,082.
Petitioners' Updated Mandatory Notices, Exhibit—6, Filed on Jan. 20, 2022, challenging U.S. Pat. No. 10,966,015.
Petitioners' Updated Mandatory Notices, Exhibit—7, Filed on Jan. 20, 2022, challenging U.S. Pat. No. 9,491,542.
Petitioners' Updated Mandatory Notices, Exhibit—7, Filed on Jan. 20, 2022, challenging U.S. Pat. No. 9,270,244.
Petitioners' Updated Mandatory Notices, Exhibit—7, Filed on Jan. 20, 2022, challenging U.S. Pat. No. 9,609,424.
Petitioners' Updated Mandatory Notices, Exhibit—7, Filed on Jan. 20, 2022, challenging U.S. Pat. No. 8,254,591.
Petitioners' Updated Mandatory Notices, Exhibit—7, Filed on Jan. 20, 2022, challenging U.S. Pat. No. 10,405,082.
Petitioners' Updated Mandatory Notices, Exhibit—8, Filed on Jan. 20, 2022, challenging U.S. Pat. No. 8,111,839.
Petitioners' Updated Mandatory Notices, Exhibit—8, Filed on Jan. 20, 2022, challenging U.S. Pat. No. 8,315,400.
Petitioners' Updated Mandatory Notices, Exhibit—9, Filed on Jan. 20, 2022, challenging U.S. Pat. No. 8,111,839.
Petitioners' Updated Mandatory Notices; Exhibit—16, Filed on Aug. 10, 2022, challenging U.S. Pat. No. 9,124,982.
Petitioners' Updated Mandatory Notices; Exhibit—8, Filed on Jan. 20, 2022, challenging U.S. Pat. No. 9,124,982.
PO's Opposition to Motion to File Supplemental Information, Exhibit—32, Filed on Aug. 17, 2023, challenging U.S. Pat. No. 9,609,424.
PO's Updated Exhibit List, Exhibit—25, Filed on Mar. 14, 2023, challenging U.S. Pat. No. 8,315,400.
PO's Updated Exhibit List, Exhibit—27, Filed on Oct. 11, 2023, challenging U.S. Pat. No. 11,039,259.
PO's Updated Exhibit List, Exhibit—27, Filed on Apr. 11, 2023, challenging U.S. Pat. No. 9,609,424.
PO's Updated Exhibit List, Exhibit—28, Filed on May 9, 2023, challenging U.S. Pat. No. 10,966,015.
PO's Updated Exhibit List, Exhibit—29, Filed on Apr. 12, 2023, challenging U.S. Pat. No. 9,491,542.
PO's Updated Exhibit List, Exhibit—29, Filed on Apr. 13, 2023, challenging U.S. Pat. No. 9,270,244.
PO's Updated Exhibit List, Exhibit—29, Filed on Apr. 4, 2023, challenging U.S. Pat. No. 8,254,591.
PO's Updated Exhibit List, Exhibit—29, Filed on May 9, 2023, challenging U.S. Pat. No. 10,405,082.
PO's Updated Exhibit List, Exhibit—30, Filed on Oct. 19, 2023, challenging U.S. Pat. No. 11,039,259.
PO's Updated Exhibit List, Exhibit—32, Filed on Mar. 16, 2023, challenging U.S. Pat. No. 8,111,839.
PO's Updated Exhibit List, Exhibit—33, Filed on Mar. 16, 2023, challenging U.S. Pat. No. 8,111,839.
PO's Updated Exhibit List; Exhibit—26, Filed on Mar. 14, 2023, challenging U.S. Pat. No. 9,124,982.
Power of Attorney for Samsung Electronics America, Inc., Exhibit—2, Filed on Dec. 30, 2021, challenging U.S. Pat. No. 10,405,082.
Power of Attorney for Samsung Electronics America, Inc., Exhibit—2, Filed on Jun. 9, 2022, challenging U.S. Pat. No. 11,057,701.
Power of Attorney for Samsung Electronics America, Inc., Exhibit—2, Filed on Jun. 9, 2022, challenging U.S. Pat. No. 11,217,237.
Power of Attorney for Samsung Electronics America, Inc., Exhibit—2, Filed on Jun. 9, 2022, challenging U.S. Pat. No. 11,244,666.
Power of Attorney for Samsung Electronics America, Inc., Exhibit—2, Filed on Jun. 9, 2022, challenging U.S. Pat. No. 11,039,259.
Power of Attorney for Samsung Electronics Co. Ltd., Exhibit—1, Filed on Jun. 9, 2022, challenging U.S. Pat. No. 11,057,701.
Power of Attorney for Samsung Electronics Co., Ltd., Exhibit—1, Filed on Dec. 10, 2021, challenging U.S. Pat. No. 8,315,400.
Power of Attorney for Samsung Electronics Co., Ltd., Exhibit—1, Filed on Dec. 30, 2021, challenging U.S. Pat. No. 10,405,082.
Power of Attorney for Samsung Electronics Co., Ltd., Exhibit—1, Filed on Jun. 9, 2022, challenging U.S. Pat. No. 11,217,237.
Power of Attorney for Samsung Electronics Co., Ltd., Exhibit—1, Filed on Jun. 9, 2022, challenging U.S. Pat. No. 11,244,666.
Power of Attorney for Samsung Electronics Co., Ltd., Exhibit—1, Filed on Jun. 9, 2022, challenging U.S. Pat. No. 11,039,259.
Power of Attorney for Samsung Electronics, America, Inc., Exhibit—2, Filed on Dec. 10, 2021, challenging U.S. Pat. No. 8,315,400.
Power of Attorney from Samsung Electronics America, Inc., Exhibit—2, Filed on Jan. 14, 2022, challenging U.S. Pat. No. 10,979,836.
Power of Attorney from Samsung Electronics America, Inc., Exhibit—2, Filed on Jan. 4, 2022, challenging U.S. Pat. No. 10,966,015.
Power of Attorney from Samsung Electronics America, Inc., Exhibit—2, Filed on Dec. 13, 2021, challenging U.S. Pat. No. 8,111,839.
Power of Attorney from Samsung Electronics America, Inc., Exhibit—2, Filed on Dec. 17, 2021, challenging U.S. Pat. No. 9,491,542.
Power of Attorney from Samsung Electronics America, Inc., Exhibit—2, Filed on Dec. 20, 2021, challenging U.S. Pat. No. 8,254,591.
Power of Attorney from Samsung Electronics America, Inc., Exhibit—2, Filed on Dec. 21, 2021, challenging U.S. Pat. No. 9,270,244.
Power of Attorney from Samsung Electronics America, Inc., Exhibit—2, Filed on Dec. 21, 2021, challenging U.S. Pat. No. 9,609,424.
Power of Attorney from Samsung Electronics Co., Ltd., Exhibit—1, Filed on Jan. 14, 2022, challenging U.S. Pat. No. 10,979,836.
Power of Attorney from Samsung Electronics Co., Ltd., Exhibit—1, Filed on Jan. 4, 2022, challenging U.S. Pat. No. 10,966,015.
Power of Attorney from Samsung Electronics Co., Ltd., Exhibit—1, Filed on Dec. 13, 2021, challenging U.S. Pat. No. 8,111,839.

(56) References Cited

OTHER PUBLICATIONS

Power of Attorney from Samsung Electronics Co., Ltd., Exhibit—1, Filed on Dec. 17, 2021, challenging U.S. Pat. No. 9,491,542.
Power of Attorney from Samsung Electronics Co., Ltd., Exhibit—1, Filed on Dec. 20, 2021, challenging U.S. Pat. No. 8,254,591.
Power of Attorney from Samsung Electronics Co., Ltd., Exhibit—1, Filed on Dec. 21, 2021, challenging U.S. Pat. No. 9,270,244.
Power of Attorney from Samsung Electronics Co., Ltd., Exhibit—1, Filed on Dec. 21, 2021, challenging U.S. Pat. No. 9,609,424.
PR 4-3 JCC Statement, Exhibit—2013, Filed on Jan. 12, 2023, challenging U.S. Pat. No. 8,315,400.
PR 4-5(d) JCC Chart, Exhibit—2011, Filed on Jan. 12, 2023, challenging U.S. Pat. No. 8,315,400.
Revised Scheduling Order, Exhibit—22, Filed on Jul. 12, 2023, challenging U.S. Pat. No. 11,039,259.
Roy Falik, Exhibit—7, Filed on Jul. 18, 2024, challenging U.S. Pat. No. 7,049,850.
Roy Falik, Exhibit—8, Filed on Jul. 18, 2024, challenging U.S. Pat. No. 9,279,263.
Sage Journal, The Future of Hearing Aid Technology, Exhibit—2008, Filed on Oct. 17, 2022, challenging U.S. Pat. No. 8,254,591.
*Samsung Elecs. Co., Ltd., et al.* v. *Staton Techiya, LLC*, IPR2022-00302, Paper 11, Exhibit—2006, Filed on Oct. 11, 2022, challenging U.S. Pat. No. 11,039,259.
*Samsung Elecs. Co., Ltd., et al.* v. *Staton Techiya, LLC*, IPR2022-00302, Paper 11, Exhibit—2006, Filed on Oct. 7, 2022, challenging U.S. Pat. No. 11,057,701.
*Samsung Elecs. Co., Ltd., et al.* v. *Staton Techiya, LLC*, IPR2022-00302, Paper 11, Exhibit—2006, Filed on Oct. 7, 2022, challenging U.S. Pat. No. 11,217,237.
*Samsung Elecs. Co., Ltd., et al.* v. *Staton Techiya, LLC*, IPR2022-00302, Paper 11, Exhibit—2006, Filed on Oct. 7, 2022, challenging U.S. Pat. No. 11,244,666.
Samsung's Claim Construction Brief, Exhibit—2012, Filed on Jan. 12, 2023, challenging U.S. Pat. No. 8,315,400.
Samsung's Responsive Claim Construction Brief, Exhibit—2012, Filed on Apr. 10, 2023, challenging U.S. Pat. No. 11,039,259.
Scheduling Order, Exhibit—11, Filed on Jan. 9, 2023, challenging U.S. Pat. No. 11,039,259.
Scheduling Order, Exhibit—11, Filed on Dec. 30, 2022, challenging U.S. Pat. No. 11,057,701.
Scheduling Order, Exhibit—14, Filed on Jul. 12, 2022, challenging U.S. Pat. No. 9,609,424.
Scheduling Order, Exhibit—14, Filed on Jul. 12, 2022, challenging U.S. Pat. No. 8,254,591.
Scheduling Order, Exhibit—14, Filed on Jul. 15, 2022, challenging U.S. Pat. No. 9,491,542.
Scheduling Order, Exhibit—14, Filed on Jul. 15, 2022, challenging U.S. Pat. No. 9,270,244.
Scheduling Order, Exhibit—14, Filed on Aug. 16, 2022, challenging U.S. Pat. No. 10,966,015.
Scheduling Order, Exhibit—15, Filed on Aug. 16, 2022, challenging U.S. Pat. No. 10,405,082.
Scheduling Order, Exhibit—16, Filed on Jun. 21, 2022, challenging U.S. Pat. No. 8,111,839.
Scheduling Order, Exhibit—17, Filed on Jun. 21, 2022, challenging U.S. Pat. No. 8,111,839.
Scheduling Order, Exhibit—9, Filed on Aug. 22, 2024, challenging U.S. Pat. No. 11,610,587.
*Staton Techiya* v *Samsung*—Docket Control Order, Exhibit—2003, Filed on Apr. 18, 2022, challenging U.S. Pat. No. 9,491,542.
*Staton Techiya* v *Samsung*—Docket Control Order, Exhibit—2003, Filed on Apr. 18, 2022, challenging U.S. Pat. No. 9,270,244.
*Staton Techiya* v *Samsung*—Docket Control Order, Exhibit—2003, Filed on Mar. 21, 2022, challenging U.S. Pat. No. 8,315,400.
*Staton Techiya* v *Samsung*—Docket Control Order, Exhibit—2003, Filed on Apr. 13, 2022, challenging U.S. Pat. No. 9,609,424.
*Staton Techiya* v *Samsung*—Docket Control Order, Exhibit—2003, Filed on Apr. 13, 2022, challenging U.S. Pat. No. 8,254,591.
*Staton Techiya* v. *Samsung*, Claim Construction Order, Exhibit—2012, Filed on Mar. 23, 2023, challenging U.S. Pat. No. 11,057,701.
*Staton Techiya* v *Samsung*—Docket Control Order, Exhibit—2003, Filed on Mar. 23, 2022, challenging U.S. Pat. No. 8,111,839.
*Staton Techiya* v *Samsung*—Docket Control Order, Exhibit—2003, Filed on May 18, 2022, challenging U.S. Pat. No. 10,405,082.
*Staton Techiya* v *Samsung*—Docket Control Order, Exhibit—2003, Filed on May 18, 2022, challenging U.S. Pat. No. 10,966,015.
*Staton Techiya* v *Samsung*—Docket Control Order, Exhibit—2003, Filed on May 18, 2022, challenging U.S. Pat. No. 10,979,836.
*Staton Techiya* v *Samsung*—Docket Control Order, Exhibit—2003, Filed on Mar. 21, 2022, challenging U.S. Pat. No. 9,124,982.
*Staton Techiya* v *Samsung*, Joint Motion to Consolidate, Exhibit—2005, Filed on Apr. 29, 2022, challenging U.S. Pat. No. 8,111,839.
*Staton Techiya* v *Samsung*, Joint Mtn to Consolidate, Exhibit—2005, Filed on Apr. 29, 2022, challenging U.S. Pat. No. 8,111,839.
*Staton Techiya* v *Samsung*, Joint Mtn to Consolidate, Exhibit—2008, Filed on Apr. 29, 2022, challenging U.S. Pat. No. 8,315,400.
*Staton Techiya* v *Samsung*, P.R. 4-5(d) Joint Claim Construction Chart, Exhibit—2011, Filed on Mar. 23, 2023, challenging U.S. Pat. No. 11,057,701.
*Staton Techiya, LLC* v. *Samsung Elecs. Co., Ltd.*, Appendix B to P.R. 4-3 Statement, Exhibit—2007, Filed on Nov. 8, 2022, challenging U.S. Pat. No. 10,405,082.
*Staton Techiya, LLC* v. *Samsung Elecs. Co., Ltd.*, Appendix B to P.R. 4-3 Statement, Exhibit—2009, Filed on Nov. 18, 2022, challenging U.S. Pat. No. 11,057,701.
*Staton Techiya, LLC* v. *Samsung Elecs. Co., Ltd.*, Appendix B to P.R. 4-3 Statement, Exhibit—2010, Filed on Nov. 8, 2022, challenging U.S. Pat. No. 10,966,015.
*Staton Techiya, LLC* v. *Samsung Elecs., Co., Ltd.*, Appendix B to P.R. 4-3 Statement, Exhibit—2011, Filed on Nov. 18, 2022, challenging U.S. Pat. No. 11,039,259.
*Staton Techiya, LLC, et al.* v. *Samsung Elecs. Co., Ltd., et al.*, Defendants' P.R. 4-2 Disclosures, Exhibit—2004, Filed on Oct. 11, 2022, challenging U.S. Pat. No. 11,039,259.
*Staton Techiya, LLC, et al.* v. *Samsung Elecs. Co., Ltd., et al.*, Defendants' P.R. 4-2 Disclosures, Exhibit—2004, Filed on Oct. 7, 2022, challenging U.S. Pat. No. 11,057,701.
*Staton Techiya, LLC, et al.* v. *Samsung Elecs. Co., Ltd., et al.*, Defendants' P.R. 4-2 Disclosures, Exhibit—2004, Filed on Oct. 7, 2022, challenging U.S. Pat. No. 11,217,237.
*Staton Techiya, LLC, et al.* v. *Samsung Elecs. Co., Ltd., et al.*, Defendants' P.R. 4-2 Disclosures, Exhibit—2004, Filed on Oct. 7, 2022, challenging U.S. Pat. No. 11,244,666.
*Staton Techiya, LLC, et al.* v. *Samsung Elecs. Co., Ltd., et al.*, Docket Control Order (Dkt. No. 43), Exhibit—2005, Filed on Oct. 7, 2022, challenging U.S. Pat. No. 11,057,701.
*Staton Techiya, LLC, et al.* v. *Samsung Elecs. Co., Ltd., et al.*, Docket Control Order (Dkt. No. 43), Exhibit—2005, Filed on Oct. 7, 2022, challenging U.S. Pat. No. 11,217,237.
*Staton Techiya, LLC, et al.* v. *Samsung Elecs. Co., Ltd., et al.*, Docket Control Order (Dkt. No. 43), Exhibit—2005, Filed on Oct. 7, 2022, challenging U.S. Pat. No. 11,244,666.
*Staton Techiya, LLC, et al.* v. *Samsung Elecs. Co., Ltd., et al.*, Docket Control Order, Exhibit—2005, Filed on Oct. 11, 2022, challenging U.S. Pat. No. 11,039,259.
*Staton Techiya, LLC, et al.* v. *Samsung Elecs. Co., Ltd., et al.*, Joint Motion to Consolidate (Dkt. No. 39), Exhibit—2007, Filed on Oct. 7, 2022, challenging U.S. Pat. No. 11,057,701.
*Staton Techiya, LLC, et al.* v. *Samsung Elecs. Co., Ltd., et al.*, Joint Motion to Consolidate (Dkt. No. 39), Exhibit—2007, Filed on Oct. 7, 2022, challenging U.S. Pat. No. 11,217,237.
*Staton Techiya, LLC, et al.* v. *Samsung Elecs. Co., Ltd., et al.*, Joint Motion to Consolidate (Dkt. No. 39), Exhibit—2007, Filed on Oct. 7, 2022, challenging U.S. Pat. No. 11,244,666.
*Staton Techiya, LLC, et al.* v. *Samsung Elecs. Co., Ltd., et al.*, Joint Motion to Consolidate (Dkt. No. 39), Exhibit—2007, Filed on Oct. 7, 2022, challenging U.S. Pat. No. 11,039,259.
*Staton Techiya, LLC, et al.* v. *Samsung Elecs. Co., Ltd., et al.*, Plaintiff's Infringement Contentions, dated Apr. 6, 2022, Exhibit—2008, Filed on Oct. 7, 2022, challenging U.S. Pat. No. 11,057,701.

(56) References Cited

OTHER PUBLICATIONS

*Staton Techiya, LLC, et al.* v. *Samsung Elecs. Co., Ltd., et al.*, Plaintiff's P.R. 4-2 Disclosures, Exhibit—2003, Filed on Oct. 7, 2022, challenging U.S. Pat. No. 11,244,666.
*Staton Techiya, LLC, et al.* v. *Samsung Elecs. Co., Ltd., et al.*, Plaintiffs' infringement Contentions, dated Apr. 6, 2022, Exhibit—2008, Filed on Oct. 11, 2022, challenging U.S. Pat. No. 11,039,259.
*Staton Techiya, LLC, et al.* v. *Samsung Elecs. Co., Ltd., et al.*, Plaintiffs' Infringement Contentions, dated Apr. 6, 2022, Exhibit—2008, Filed on Oct. 7, 2022, challenging U.S. Pat. No. 11,217,237.
*Staton Techiya, LLC, et al.* v. *Samsung Elecs. Co., Ltd., et al.*, Plaintiffs' Infringement Contentions, dated Apr. 6, 2022, Exhibit—2008, Filed on Oct. 7, 2022, challenging U.S. Pat. No. 11,244,666.
*Staton Techiya, LLC, et al.* v. *Samsung Elecs. Co., Ltd., et al.*, Plaintiffs' P.R. 4-2 Disclosures, Exhibit—2003, Filed on Oct. 11, 2022, challenging U.S. Pat. No. 11,039,259.
*Staton Techiya, LLC, et al.* v. *Samsung Elecs. Co., Ltd., et al.*, Plaintiffs' P.R. 4-2 Disclosures, Exhibit—2003, Filed on Oct. 7, 2022, challenging U.S. Pat. No. 11,057,701.
*Staton Techiya, LLC, et al.* v. *Samsung Elecs. Co., Ltd., et al.*, Plaintiffs' P.R. 4-2 Disclosures, Exhibit—2003, Filed on Oct. 7, 2022, challenging U.S. Pat. No. 11,217,237.
Stipulation Letter dated Apr. 20, 2022, Exhibit—1031, Filed on May 11, 2022, challenging U.S. Pat. No. 8,254,591.
Stipulation Letter from D. Rokach to J. Snodgrass, Exhibit—1025, Filed on Nov. 10, 2022, challenging U.S. Pat. No. 11,244,666.
Stipulation Letter from D. Rokach to J. Snodgrass, Exhibit—1027, Filed on Nov. 10, 2022, challenging U.S. Pat. No. 11,057,701.
Stipulation Letter from D. Rokach to J. Snodgrass, Exhibit—1030, Filed on Nov. 15, 2022, challenging U.S. Pat. No. 11,217,237.
Stipulation Letter from D. Rokach to J. Snodgrass, Exhibit—1033, Filed on Nov. 20, 2022, challenging U.S. Pat. No. 11,039,259.
Stipulation Letter, Exhibit—1015, Filed on Apr. 20, 2022, challenging U.S. Pat. No. 8,315,400.
Stipulation Letter, Exhibit—1019, Filed on Jun. 14, 2022, challenging U.S. Pat. No. 10,405,082.
Stipulation Letter, Exhibit—1019, Filed on Jun. 14, 2022, challenging U.S. Pat. No. 10,966,015.
Stipulation Letter, Exhibit—1020, Filed on Jun. 14, 2022, challenging U.S. Pat. No. 10,979,836.
Stipulation Letter, Exhibit—1023, Filed on May 10, 2022, challenging U.S. Pat. No. 9,609,424.
Stipulation Letter, Exhibit—1044, Filed on Apr. 20, 2022, challenging U.S. Pat. No. 8,111,839.
Stipulation Letter, Exhibit—1034, Filed on Apr. 20, 2022, challenging U.S. Pat. No. 9124982.
Summary of all applications in the '082 patent family, Exhibit—1018, Filed on Dec. 12, 2021, challenging U.S. Pat. No. 10,405,082.
Summary of all applications in the '836 patent's family, Exhibit—1019, Filed on Jan. 14, 2022, challenging U.S. Pat. No. 10,979,836.
Summary of Application in '839 Patent Priority Chain, Exhibit—1041, Filed on Dec. 13, 2021, challenging U.S. Pat. No. 8,111,839.
Summary of applications in '015 patent family, Exhibit—1018, Filed on Jan. 4, 2022, challenging U.S. Pat. No. 10,966,015.
Summary of applications in '591 priority chain, Exhibit—1030, Filed on Dec. 20, 2021, challenging U.S. Pat. No. 8,254,591.
Summary of Applications in '839 Priority Chain, Exhibit—1041, Filed on Dec. 13, 2021, challenging U.S. Pat. No. 8,111,839.
Summary of Applications in '982 Priority Chain; Exhibit—1032, Filed on Dec. 13, 2021, challenging U.S. Pat. No. 9,124,982.
Techopedia, Faceplate, Exhibit—2011, Filed on Sep. 13, 2022, challenging U.S. Pat. No. 8,111,839.
Techopedia, Faceplate; Exhibit—2010, Filed on Sep. 9, 2022, challenging U.S. Pat. No. 9,124,982.
Termination Decision: Post-DI Settlement, Exhibit—20, Filed on Dec. 12, 2024, challenging U.S. Pat. No. 11,610,587.
Termination Decision: Pre-DI settlement, Exhibit—16, Filed on Dec. 12, 2024, challenging U.S. Pat. No. 9,191,083.
Termination Decision: Pre-DI settlement, Exhibit—16, Filed on Dec. 12, 2024, challenging U.S. Pat. No. 9,614,943.
Termination Decision: Pre-DI settlement, Exhibit—16, Filed on Dec. 12, 2024, challenging U.S. Pat. No. 7,049,850.
Termination Decision: Pre-DI settlement, Exhibit—17, Filed on Dec. 12, 2024, challenging U.S. Pat. No. 9,279,263.
Termination Decision: Pre-DI settlementPaper15, Dec. 12, 2024, challenging U.S. Pat. No. 8,434,966.
Transcript of Deposition of Chris Kyriakakis, Ph.D. taken Oct. 7, 2022, Exhibit—2007, Filed on Oct. 17, 2022, challenging U.S. Pat. No. 9,609,424.
Transcript of Deposition of Christopher Struck, Exhibit—1028, Filed on Jun. 15, 2023, challenging U.S. Pat. No. 11,057,701.
Transcript of Deposition of Dr. Les Atlas, Exhibit—2007, Filed on Oct. 17, 2022, challenging U.S. Pat. No. 8,254,591.
Transcript of Deposition of Dr. Les Atlas; Exhibit—2007, Filed on Sep. 9, 2022, challenging U.S. Pat. No. 9,124,982.
Transcript of Deposition of Les Atlas, Ph.D., Aug. 18, 2022, Exhibit—2007, Filed on Sep. 13, 2022, challenging U.S. Pat. No. 8,111,839.
Transcript of Deposition of Les Atlas, Ph.D., Exhibit—2016, Filed on Apr. 10, 2023, challenging U.S. Pat. No. 11,039,259.
Transcript of Deposition of Nathaniel Polish, Ph.D., taken Sep. 29, 2022, Exhibit—2007, Filed on Oct. 19, 2022, challenging U.S. Pat. No. 9,491,542.
Transcript of Deposition of Nathaniel Polish, Ph.D., taken Sep. 29, 2022, Exhibit—2007, Filed on Oct. 19, 2022, challenging U.S. Pat. No. 9,270,244.
Transcript of Deposition of Richard M. Stern, Exhibit—2010, Filed on Mar. 23, 2023, challenging U.S. Pat. No. 11,057,701.
Transcript of Deposition of Richard M. Stern, Ph.D., taken Oct. 27, 2022, Exhibit—2009, Filed on Nov. 8, 2022, challenging U.S. Pat. No. 10,405,082.
Transcript of Deposition of Richard M. Stern, Ph.D., taken Oct. 27, 2022, Exhibit—2009, Filed on Nov. 8, 2022, challenging U.S. Pat. No. 10,966,015.
Transcript of Deposition of Richard Stern, Ph.D., Exhibit—2010, Filed on Sep. 9, 2022, challenging U.S. Pat. No. 8,315,400.
U.S. Appl. No. 09/653,869, Exhibit—1007, Filed on Dec. 20, 2021, challenging U.S. Pat. No. 8,254,591.
U.S. Pat. No. 10,405,082, Exhibit—1001, Filed on Dec. 30, 2021, challenging U.S. Pat. No. 10,405,082.
U.S. Appl. No. 61/778,737, Exhibit—1008, Filed on Dec. 21, 2021, challenging U.S. Pat. No. 9,270,244.
U.S. Appl. No. 62/575,713, Exhibit—1006, Filed on Dec. 30, 2021, challenging U.S. Pat. No. 10,405,082.
U.S. Appl. No. 62/575,713, Exhibit—1006, Filed on Jan. 4, 2022, challenging U.S. Pat. No. 10,966,015.
Wikipedia, Apple headphones, Exhibit—2010, Filed on Sep. 13, 2022, challenging U.S. Pat. No. 8,111,839.
Wikipedia, Microphone, Exhibit—2012, Filed on Sep. 13, 2022, challenging U.S. Pat. No. 8,111,839.
Wikipedia, Microphone; Exhibit—2011, Filed on Sep. 9, 2022, challenging U.S. Pat. No. 9,124,982.
Wiley Elec and Elecs Eng Dictionary (excerpts), Exhibit—2004, Filed on Mar. 21, 2022, challenging U.S. Pat. No. 8,315,400.
Wiley Electrical and Electronics Engineering Dictionary (excerpt), Exhibit—2009, Filed on Oct. 7, 2022, challenging U.S. Pat. No. 11,217,237.

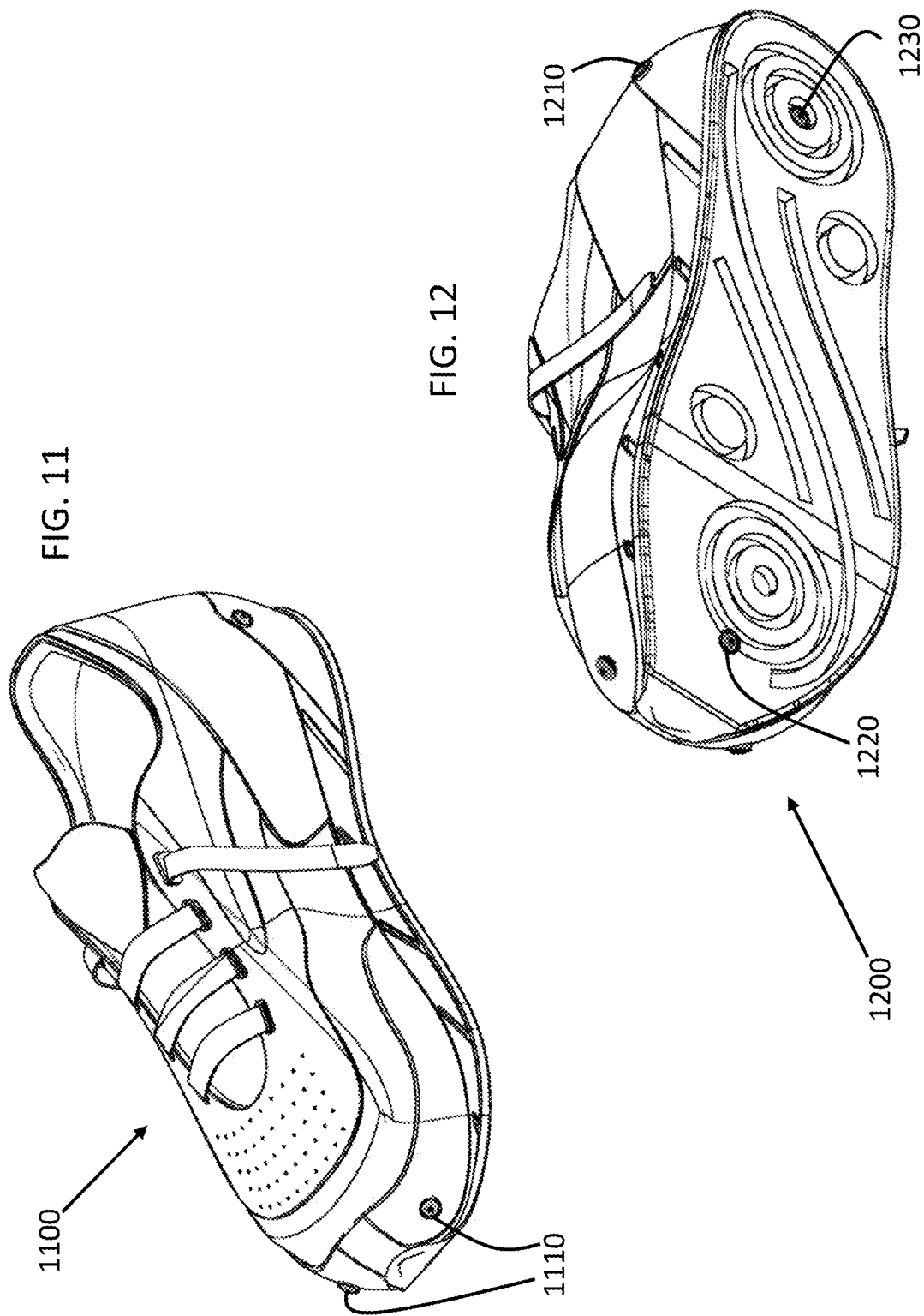

INFORMATION PROCESSING USING A POPULATION OF DATA ACQUISITION DEVICES

CROSS-REFERENCE TO RELATED APPLICATION(S)

This application is a continuation in part of U.S. patent application Ser. No. 17/235,130, filed 20 Apr. 2021, which is a continuation of and claims priority to allowed U.S. patent application Ser. No. 16/736,820, filed 8 Jan. 2020, which is a continuation of and claims priority to allowed U.S. patent application Ser. No. 16/055,488, filed Aug. 6, 2018, which is a continuation of and claims priority to U.S. patent application Ser. No. 13/976,636, filed on Oct. 1, 2013, which is a National Stage Entry of PCT/US11/68103 filed on Dec. 30, 2011, which claims priority to and the benefit of U.S. Provisional Patent Application Ser. No. 61/431,507 filed Jan. 11, 2011, and which also claims priority to and the benefit of U.S. Provisional Patent Application Ser. No. 61/428,369 filed Dec. 30, 2010, all of which are herein incorporated by reference in their entireties.

FIELD OF THE INVENTION ne present invention relates to processing of information from a population of data acquisition devices, and in some examples, relates to processing of audio or multimedia data acquired from an adaptively selectable population of personal wireless devices.

BACKGROUND

Devices that are capable of acquiring, and in some cases locally processing, audio or multimedia information from their local environment have become ubiquitous over the past several years, and there is little reason to expect that such a trend will not continue. For example, "smart" cellular telephones (e.g., Apple iPhone®, Android™-operating system based phones) have significant local processing capabilities as well as audio and video acquisition devices.

SUMMARY OF THE INVENTION

In one aspect of the present invention, in general, the audio and multimedia acquisition capabilities of a set of devices may be exploited to aggregate acquired content and fuse the information in that content, for instance, for audio scene analysis. In some example embodiments, devices from a large population may be adaptively selected and/or configured according to triggering events detected at the devices or by the network. Relating to the audio scene, the information sensed and acquired from one or more devices may be processed, customized and personalized to consumers to mitigate, amplify or pass-through acoustic and other information to users, based on factors such as models of users' requirements and users' past information consumption behavior. Thus an exemplary system of the present invention may mediate ambient and explicitly supplied information, especially audio information, and may act as an arbiter of information for the user. Some of the system actions may be based on information from one device, while other actions may be based on information from multiple devices. The information filtered to users may be utilized to form virtual communities based on shared interests and common information, and to ensure that relevant information including alerts, marketing information, and news reaches these communities.

According to another aspect of the present invention, in general, a distributed system may include a plurality of distributed devices, with at least one of a communication system or one or more of the distributed devices configured as a controller. Each device has at least a communication capability for interchanging information with other of the devices and/or with the communication system. At least one of the devices may include one or more sensors for acquiring sensor data related to the environment of the device. The controller is configured to perform functions including: determining locations of at least some of the devices, selecting devices from among the plurality of devices and receiving information based on the sensor data acquired at the selected devices, and combining the information received from multiple of the selected devices to determine one or more characteristics of the environment of one or more of the devices.

In other aspects of the present invention, the distributed system may include devices that mediate all audio information sensed at the device to mitigate, amplify or pass-through information. In some examples, such information is optionally logged and analyzed to determine trend-related information.

Other features and advantages of the invention are apparent from the following description, and from the claims.

BRIEF DESCRIPTION OF THE DRAWINGS

The invention may be understood from the following detailed description when read in connection with the accompanying drawing. It is emphasized, according to common practice, that various features of the drawings may not be drawn to scale. On the contrary, the dimensions of the various features may be arbitrarily expanded or reduced for clarity. Moreover, in the drawing, common numerical references are used to represent like features. Included in the drawing are the following figures:

FIGS. 11 and 12 illustrate an example of a footwear device configuration.

DETAILED DESCRIPTION

Figure 1:
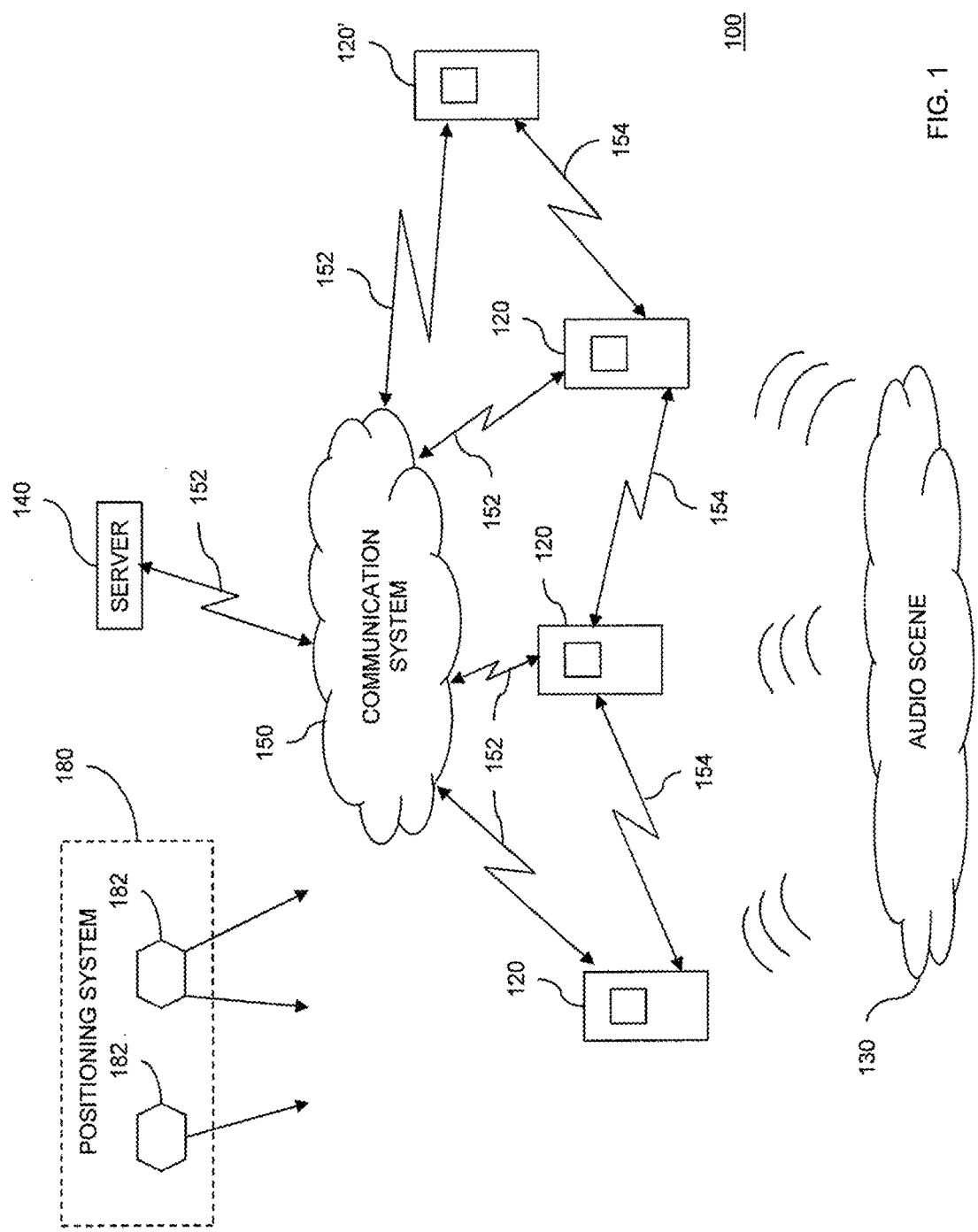
FIG. 1 is a functional block diagram of an information processing system, according to an exemplary embodiment of the present invention.

Personal wireless devices, as well as other types of computing or communication devices, have become ubiquitous in our environment. Generally, such devices have a number of sensors, which may include, for instance, microphones, cameras, accelerometers, and in some cases may even have sensors for biometric information, such as heart rate. Such devices also generally include one or more communication systems, for example, a cellular telephone radio system (e.g., Code Division Multiple access (CDMA) or Global System for Mobile Communications (GSM)), a wireless local area network system (e.g., Wi-Fi, IEEE 802.11), wired computer network connections (e.g., data network connections via USB cradles, possibly via desktop computer applications) and in some cases other systems based on radio frequency (e.g., Bluetooth®) or optical (e.g., infra-red) transmission. Finally, such devices generally are "location aware" and/or locatable by the infrastructure in which they operate. For example, such devices may have global positioning system (GPS) receivers, enhanced GPS (which operates in conjunction with cellular telephone infrastructure), and/or Wi-Fi based maps (which use a map of Wi-Fi access points to locate the device). The cellular infrastructure may, for example, be able to locate the device based on cellular signal strength and/or triangulation approaches.

In some aspects of the present invention, the combination of characteristics of these devices provides a potentially rich source of information that may be combined in a way that generates valuable information that is not necessarily available to any individual device. As an illustrative example, audio processed locally at many different devices may be combined to identify geographic or social group trends based on keywords spoken or other acoustic events (e.g., coughs) that are detected at the devices.

Detection of coughs is an example where detection of non-speech acoustic events may be useful. Because a cough is often a sudden and often repetitively occurring reflex, frequent coughing may indicate the presence of a disease (e.g., many viruses and bacteria benefit evolutionarily by causing the host to cough, which helps to spread the disease to new hosts). Most of the time, coughing is caused by a respiratory tract infection but can be triggered by choking, smoking, air pollution, asthma, gastro-esophageal reflux disease, post-nasal drip, chronic bronchitis, lung tumors, heart failure and medications such as ACE inhibitors. Detection of such events in the vicinity of the devices may provide significant information.

In other aspects of the present invention, the rich sensor capabilities of the devices may provide a way to track activity of a user (e.g., owner) of the device, to enhance the user's experience with various computing applications (such as searching or personalization). As an illustrative example, topics of conversation in the vicinity of the device may affect the ranking of search results or the ordering of presentation of news stories on the device.

In some aspects of the present invention, the rich source of information over many devices and the tracking of individual activity may be combined, to benefit from their synergy.

Referring to FIG. 1, a functional block diagram of an exemplary information processing system, designated generally as system 100, is shown. System 100 may include one or more distributed devices 120 (also referred to herein as devices 120) and device 120' (also referred to as controller 120') in an environment. One or more of devices 120 and device 120' may be configured to acquire information relating to audio scene 130. Device 120' may be the same as device 120, except that device 120' may be configured to act as a controller for selectively acquiring sensor information from among devices 120 and for determining a characteristic of audio scene 130. Although one device 120' is illustrated as being a controller, it is understood that multiple devices 120' may act as controllers.

Although device 120' is illustrated as a controller forgathering sensor information and determining a characteristic of audio scene 130, it is understood that communication system 150 and/or server 140 may also be configured to act as a controller. Communication system 150 or server 140 may collect at least one of sensor information from devices 120, 120', local data analysis information from devices 120, 120' or scene analysis information from device 120'.

Devices 120 and device 120' may be capable of direct communication with each other, via communication link 154. Devices 120 and device 120' may also be capable of communication with communication system 150, via communication link 152. Devices 120 and device 120' may also be in communication with central server 140, via communication system 150 and communication link 152. Devices 120, 120' may include wired or wireless devices. As discussed further below, devices 120, 120' may be at fixed positions or may be mobile devices.

In one exemplary embodiment, a number of devices 120 are present in an environment. In some examples, the devices 120 (and device 120') are cellular telephones (e.g., "smartphones"). The environment represented by audio scene 130 may be an urban environment, for example, with the devices 120, 120' being present on city streets, in office buildings, or in homes of the users. Generally, the devices 120, 120' may be personal to the users/owners (of the devices), and may be mobile devices, carried with the user throughout the day.

In FIG. 1, a small number of representative devices 120, 120' are illustrated. As discussed further below, the potentially enabled devices 120, 120' may be part of a large population of devices (e.g., a large fraction of the telephones in a metropolitan area) and system 100 may adaptively enable particular subsets of the devices 120 and/or selectively configure enabled devices 120. For instance, device 120' (or server 140) may enable and/or configure the devices 120 according to triggering events detected at one or more devices 120, 120'.

It should be understood that the description below focuses on smartphones as an example, and other types of fixed or mobile devices may be used in conjunction with or instead of smartphones. Also, the description below focuses on aggregation or combination of audio information as an example, but aggregation and processing of other forms of information, including video and biometric information may be performed in conjunction with or instead of the audio data examples described below.

As introduced above, any particular device 120, 120' is able to sense some aspect of an overall audio "scene" in its environment. Such a scene may include, for example, the device owner's own speech even when not carrying out a telephone call, other sounds made by the owner (such as coughing), the speech of others in proximity to the user and environmental sounds in proximity to the user (such as sirens, gunshots, etc.).

Generally, system 100 makes use of the audio acquisition capabilities of one or more of the devices 120, 120' in order to extract information related to the views of the audio scene 130 by the one or more devices 120, 120'. In one exemplary approach to acquisition of the raw content, every device 120 could continually transmit its acquired signals over communication system 150 to a central server 140 (via communication link 152). For example, the communication system 150 may comprise a cellular telephone system and/or a wireless data network. However, such continual transmission may not be feasible due to the sheer volume given the large number of devices 120, 120' that are fielded, and may raise other issues regarding privacy of those in the environments of the devices 120, 120'.

Another exemplary approach to extracting information is for each device 120, 120' to perform a local signal analysis based on the signals acquired by that device. However, such an approach may have limitations due to the computational limitations of the devices 120, 120'. Also, a purely local processing may lose advantages that could be gained by fusing of information from multiple devices 120, 120'.

An exemplary approach describe below addresses some of the limitations of a purely local or a purely centralized approach using a combination of one or more of the following features:

1) Local processing of acquired signals (on devices 120), at least to identify occurrences of events that may be of interest;
2) Local buffering of audio for selective transmission to device 120' or central server 140, for example, on an ongoing basis or based on a request from device 120' or server 140, or based on local identification of a local event (at one or more of devices 120); and
3) Selective enabling of acquisition and/or processing (or specification of the type of processing) at particular devices 120, 120', for example, based on their geographic location and/or other proximity metrics (e.g., a social network rather than a geographic distance metric).

Note that the locations of the devices 120, 120' (e.g., three-dimensional coordinates) are generally known by the devices 120, 120' and/or central server 140. As an example, a positioning system 180 makes use of units having known locations, such as GPS satellites 182, fixed cellular transmission towers, Wi-Fi access points, etc. to maintain an estimate of the positions of the devices.

Figure 2A:
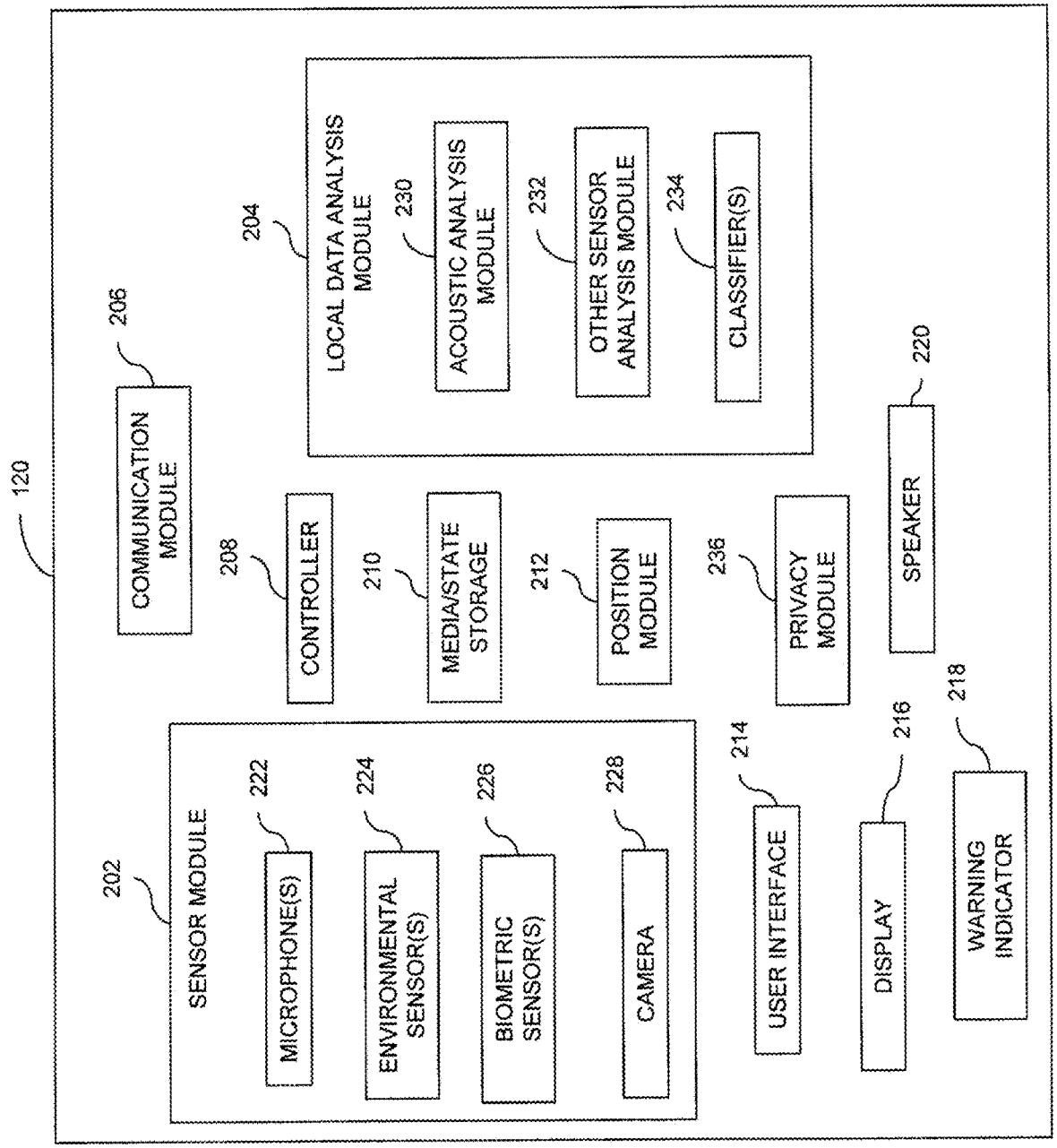
FIG. 2A is a functional block diagram of a distributed device of the system shown in FIG. 1, according to an exemplary embodiment of the present invention.

Referring to FIG. 2A, a functional block diagram of exemplary device 120 is shown. Device 120 may include one or more of sensor module 202, local data analysis module 204, communication module 206, controller 208, media/state storage 210, position module 212, user interface 214, display 216, warning indicator 218, speaker 220 and privacy module 236. A typical device 120 includes communication module 206, which provides a communication link 152 through the communication system 150 to sever 140 and/or a communication link 154 to other devices 120, 120'. Communication module 206 may also serve a role in acquiring positioning signals (e.g., GPS signals, Wi-Fi signal strengths, etc.), and may also provide a way to communicate directly with other devices 120.

Device 120 may include sensor module 202 for the acquisition of sensor information. Sensor module 202 may include one or more microphones 222 for collecting acoustic information regarding audio scene 130 (FIG. 1). Sensor module 202 may also include one or more environmental sensors (such as a temperature sensor, a motion sensor such as an accelerometer) for collecting environmental information associated with device 120. Sensor module 202 may also include one or more biometric sensors 226 (such as heart rate) for sensing biometric information regarding a user of device 120. Sensor module 202 may also include camera 228 (i.e., an image sensor) for capturing still images and/or video of the surrounding environment of device 120. Sensor module 202 may also include a compass for providing location information. In general, sensor module 202 may include any sensor capable of measuring a physical quantity and converting it into a signal that may be used by system 100. For example, sensors in sensor module 202 may also include, without limitation, one or more of light detection sensors, proximity sensors, gravity detection sensors, a magnetic field detection sensors, electrical field detection sensors, vibration sensors, pressure sensors, humidity sensors, moisture sensors, toxin detection sensors, nutrient detection sensors or pheromone detection sensors.

User interface 214 may include any suitable user interface capable of providing parameters for one or more of sensor module 202, local data analysis module 204, communication module 206, media/state storage 210, position module 212, display 216, warning indicator 218, speaker 220 and privacy module 236. User interface 214 may include, for example, a pointing device, a keyboard and/or a display device.

Device 120 may include display 216, warning indicator 218 and/or speaker 220 for presenting information to a user of device 120. Display 216 may include any suitable display device capable of presenting information on device 120. Warning indicator 218 may include any suitable visual indicator for presenting a warning on device 120. The warning may include, for example, an indication that audio information is being recorded. It is understood that speaker 220 may also audibly present a warning indication. Although user interface 214 and display 216 are illustrated as separate devices, it is understood that the functions of user interface 214 and display 216 may be combined into one device. According to an exemplary embodiment, device 120 may receive acoustic and/or other information (via display 216, warning indicator 218 and/or speaker 220) that has been mitigated, amplified and/or passed to device 120 from device 120' (FIG. 1) based on information acquired from one or more devices 120.

Device 120 may include position module 212, to maintain a position estimate for device 120. For example, position module 212 may use positioning system 180 (FIG. 1) to obtain the position estimate.

Media/state storage 210 may store at least one of raw sensor information (from sensor module 202), locally analyzed information (from local data analysis module 204) or location information (from position module 212). Media/state storage 210 may include, for example, a magnetic disk, an optical disk, flash memory or a hard drive.

Controller 208 may be coupled, for example, via a data and control bus (not shown) to one or more of sensor module 202, local data analysis module 204, communication module 206, media/state storage 210, position module 212, user interface 214, display 216, warning indicator 218, speaker 220 and privacy module 236. Controller 208 may be configured to control acquisition of sensor information, local analysis of sensor information, transmission and/or receipt of sensor information, transmission and/or receipt of local analysis information, as well as any presentation of information by device 120 (such as via display 216, warning indicator 218 and/or speaker 220). Controller 208 may include, for example, a logic circuit, a digital signal processor or a microprocessor. It is understood that one or more functions of local data analysis module 204 may be performed by controller 208.

Local data analysis module 204 may be configured to analyze information collected locally by sensor module 202 for device 120. Local data analysis module 204 may include acoustic analysis module 230 for analyzing audio information (such as from one or more microphones 222). The audio information may include speech, music as well as environmental sounds (such as an approaching train). The speech may be generated by a user of device 120, as well as by other individuals proximate to device 120. Local data analysis module 204 may perform the analysis either locally or with the aid of backend server architecture or similar mechanisms.

Local data analysis module 204 may also include other sensor analysis module 232 for analyzing information from other sensors of sensor module 202. For example, other sensor analysis module 232 may analyze information from one or more of environmental sensor(s) 224, biometric sensor(s) 226 and/or camera 228. Local data analysis module 204 may combine results from acoustic analysis module 230 (such as keywords, target sounds) and other sensor analysis module 232 to determine the occurrence of one or more particular events (and/or a characteristic of audio scene 130).

Acoustic analysis module 230 and/or other sensor module 232 may also pre-process the respective sensor information, for example, to substantially remove or reduce noise. Modules 230, 232 may also filter the noise-reduced sensor information to identify high value signals which may be indicative of the occurrence of particular events.

Local data analysis module 230 may include classifiers 234 associated with acoustic analysis module and/or other sensor analysis module. Classifiers 234 may be used to build profiles of audio information, environmental information, biometric information and/or image information.

In an exemplary embodiment, acoustic analysis module 230 may preprocess the audio information to recognize speech, perform keyword spotting on speech information, and in addition build voice models of various speakers within the auditory range of the device. The models may, for example, use classifiers 234 and machine learning methods to identify gender, probable age range, nationality and other demographic features from the speech signals.

In addition, there may be classifiers 234, for instance, to recognize any slurring due to the influence of alcohol or similar substances, accent classifiers to detect and identify accent patterns belonging to specific language groups, and emotion classifiers to classify speakers and speech into happy, sad, stressed, angry or other emotional states. Thus, given any audio input that includes any speech, individual devices 120 or system 100 (FIG. 1) as a whole may be able to build an acoustic profile of each speech participant in that input, where the profile not only includes the keywords spotted, but also other data such as demographic data about each speaker including gender, probable age, possible nationality etc., as well as classifier results about emotional state, and/or whether the speaker is under the influence.

The acquisition of keywords with demographic data may help advertisers target their sales, based on factors such as gender, age and potential levels of disposable income, and to track their sale cycle from users noticing their advertisements to those users who actually make a purchase. Emotion indicators may be used to take palliative or preventative steps to avoid customer dissatisfaction. Other information like slurring may be used as corroboratory information in situations such as accidents or may be used to prevent accidents.

Privacy module 236 may include mechanisms to implement privacy and/or security requirements and policies for applications relating to the acquisition and use of information of various kinds, including audio information, by one or more devices associated with a number of carriers. These policies and mechanisms may control the use of devices 120 (and device 120' (FIG. 1)) including the ability to remotely switch on and switch off sensing (e.g., listening), the ownership of any audio information garnered by these devices 120 (and device 120' (FIG. 1)), the users' ability to easily control sensing and information acquisition, mechanisms to opt-in and opt-out of applications, carrier-wide or network-wide data gathering, the protection of any audio personally identifiable information (PII) that is gathered, and any aggregated data that is created from a number of devices 120 (device 120' (FIG. 1) and networks. Policies or standard practices may also be established for private or semi-private situations where not all users present have opted-in for data acquisition. For example, when system 100 (FIG. 1) records speech from users that are not likely to be opted-in to the information acquisition, system 100 may provide a warning indication to all devices 120 in the immediate vicinity to indicate that audio information is being recorded. The warning indication may be provided on warning indicator 218.

Figure 2B:
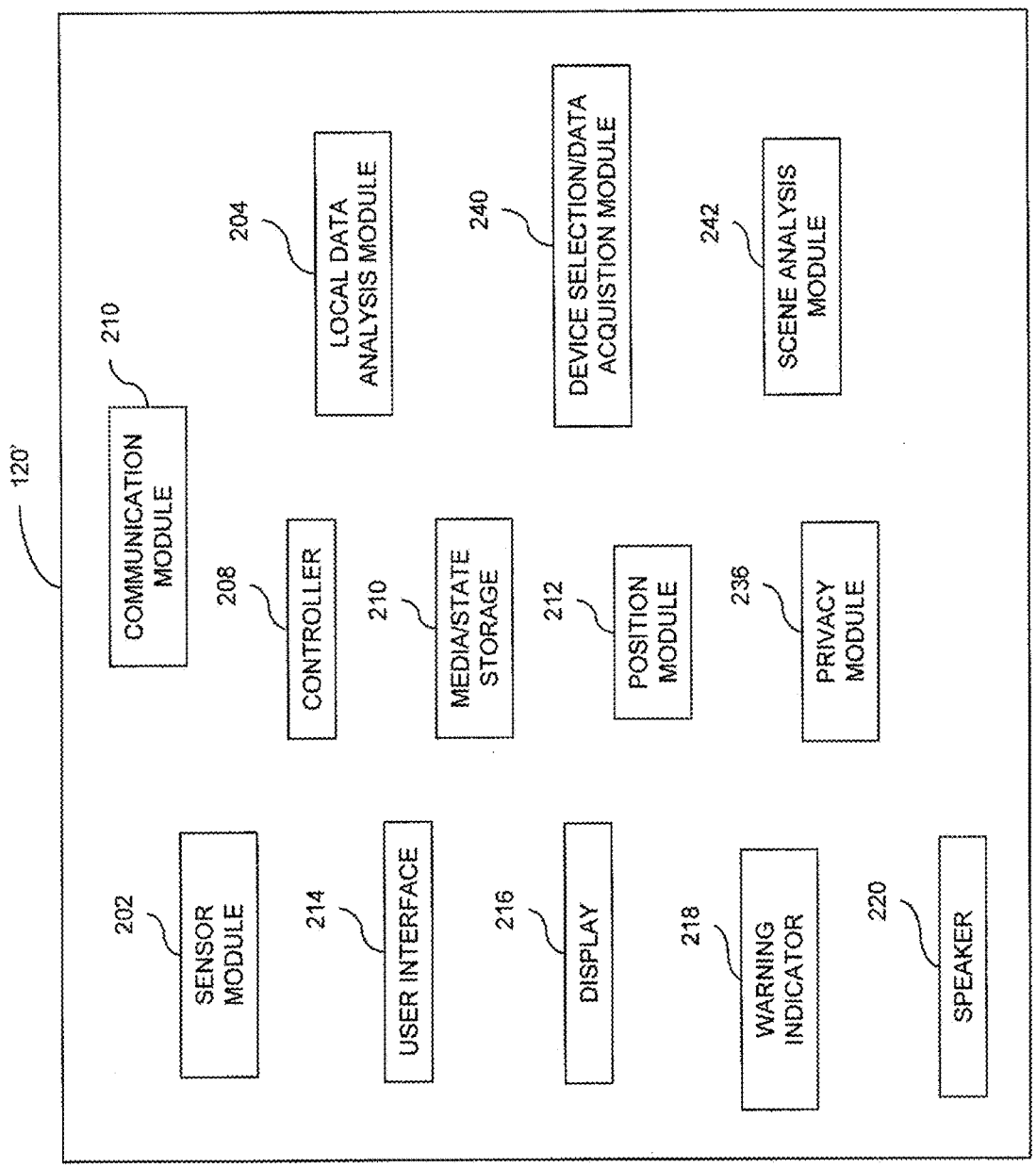
FIG. 2B is a functional block diagram of a controller of the system shown in FIG. 1, according to an exemplary embodiment of the present invention.

Referring next to FIG. 2B, a functional block diagram of exemplary device 120' is shown. Device 120' is similar to device 120 (FIG. 2A), except that device 120' may also include device selection/data acquisition module 240 and scene analysis module 242. Similarly, to device 120 (FIG. 2A), components of device 120' may be coupled together via a data and control bus (not shown).

Device selection/data acquisition module 240 (also referred to herein as module 240) may receive sensor information and/or locally analyzed information from selected devices 120 (FIG. 1). Scene analysis module 242 may combine the sensor information and/or locally analyzed information from among the selected devices, in order to determine at least one characteristic of audio scene 130 (or the environment, in general).

Module 240 may determine the locations of at least some of devices 120 (FIG. 1). Module 240 may select one or more devices 120 (FIG. 1) from among plural devices 120, for example, based on the location of these devices 120 as well as any characteristics (such as an event) determined by scene analysis module 242. Accordingly, as a characteristic is detected (by scene analysis module 242), module 240 may adaptively acquire information from selected devices 120 (FIG. 1), in order to better analyze audio scene 130. Module 240 may also configure selected devices 120 (FIG. 1) to acquire specific information, (for example one device 120 may acquire image data via camera 228 (FIG. 2A) whereas another sensor may be configured to acquire audio data via microphone 222 (FIG. 2A). As another example, module 240 may configure multiple devices 120 to acquire audio data via respective microphones 222 (FIG. 2A), so that the multiple microphones 222 form a beam forming array.

Referring generally to FIGS. 1, 2A and 2B, system 100 makes use of one or more of enabling and configuring of devices (via device selection/data acquisition module 240) for prospective monitoring, access to logged data for retrospective analysis, and real-time notification of events (such as by scene analysis module 242). This adaptation of system 100 may be based on detection of triggering events at the devices 120, 120'. For example, device 120' may enable detection of certain acoustic events (e.g., words, spoken topics, music, and environmental sounds) and may adapt the configurations on selected devices 120 based on reports from other devices 120.

Device 120' (and devices 120) may include software for coordinating the set of devices 120. The software may have centralized control, peer-to-peer control or a hybrid model involving centralized, peer-to-peer and other control mechanisms. Individual devices 120, 120' may switch between being master devices controlling other devices, or slave devices under the temporary partial control of other devices. The network of devices 120, 120' may so configure itself to optimize power consumption on individual devices 120 by distributing the sensing load across a number of devices 120, 120', or by other mechanisms such as sharing bandwidth across devices 120, 120'. The networking used may be based on ideas related to mobile ad hoc networks (MANET), Scatternet or other mechanisms.

For example, system 100 may dynamically organize and reorganize its nodes into hierarchies or graphs, with some devices 120, 120' chosen to be master nodes while other possibly geographically proximate devices to be slave nodes. Slave nodes may perform actions based on instructions from master nodes. They may preprocess information and convey processed information to master nodes, instead of conveying all information acquired, thus distributing computation among nodes and reducing the communication bandwidth. In addition, communication requirements may improve because only a few master nodes may communicate with each other, instead of all, say N devices trying to communicate with each other, which would require (N.sup.2/2) connections.

Because each node knows its location, depending on system requirements, the network may organize itself into one or more linear chains or local groups, where information is passed between physically proximate devices, very much like a bucket brigade conveying information. With a peer-to-peer architecture, individual devices 120, 120'—either just master nodes or both master nodes and slave nodes—may record information about neighboring nodes and their capabilities and features, so that, for instance, connectivity between any pair of nodes can easily and effectively be established at low computational cost.

Other optimization techniques may also be adopted—for instance, when data logs are recorded, the system may determine if several devices are in the same audio or other sensor context. For example, if several phones 120, 120' are located in the same context, not every phone 120, 120' has to record all data—the system 100 may designate a scribe node which acts as a local repository for data and for ensuring the data gets stored to some centralized server 140 (or device 120') in the cloud. This may save considerable logging effort on the part of the other nodes.

Alternatively. or in addition, the system 100 may distribute sensor load among devices 120, 120' so that not every node has to acquire information via all of its sensors in sensor module 202. Some sensor modules 202 may concentrate on acquiring audio information, while other devices 120, 120' may acquire position information and still other sensor modules 202 may acquire temperature or altitude information, and so on. This may reduce power and communication bandwidth requirements for the entire system 100. Several such schemes may be devised to optimize the throughput and efficiency of the system as a whole. According to an exemplary embodiment, system 100 may also distribute processing of sensor information among devices 120, 120', so that different individual tasks are performed by devices 120, 120'. This may reduce the computational burden on some devices 120 (or device 120') which may not have suitable processing capabilities for a specific task.

The system 100 as a whole may use carrier-agnostic handlers in the cloud. Specifically, the networking may utilize services from a number of wireless telephony, Wi-Fi or other carriers, and suitable policies may be put in place to enable carrier-agnostic behaviors. Specifically, so that no user may be denied sharing of information because of association with specific carriers, and so that digital bridges exist to share information across carriers where desired. In a variant, some features may be made unique to a carrier for marketing reasons.

It is understood that devices 120, 120' do not have to be phones. Devices 120, 120' may be stand-alone devices, or may be an integral part of a GPS, hearing aid, mobile phone. TV remote, car key fob, portable game controller or similar device.

Device 120 (and/or device 120') may be carried by the user on his person, or be installed in or on a vehicle such as a car. For certain applications, devices 120 (and/or device 120') may be fixed and installed at home, or be part of fixed telephones, desktop computers, TV sets or game consoles. Each device 120 (and/or device 120') may include one or more sensors with associated software. Different kinds of devices 120, 120' may include different sensors and/or different software. If device 120 or device 120' is more like a smartphone, system 100 may have access to textual data including electronic mail, chat transcripts and documents, and audio data including phone conversations, music on the device or streamed to the device, ambient audio picked up by microphones, and user search logs. All of this data may be relevant to the user. This data, along with the user's context and environmental variables, may be used for personalization of information consumed by the user and then where appropriate repurposed for commercial applications to the user or the community at large.

Figure 3:
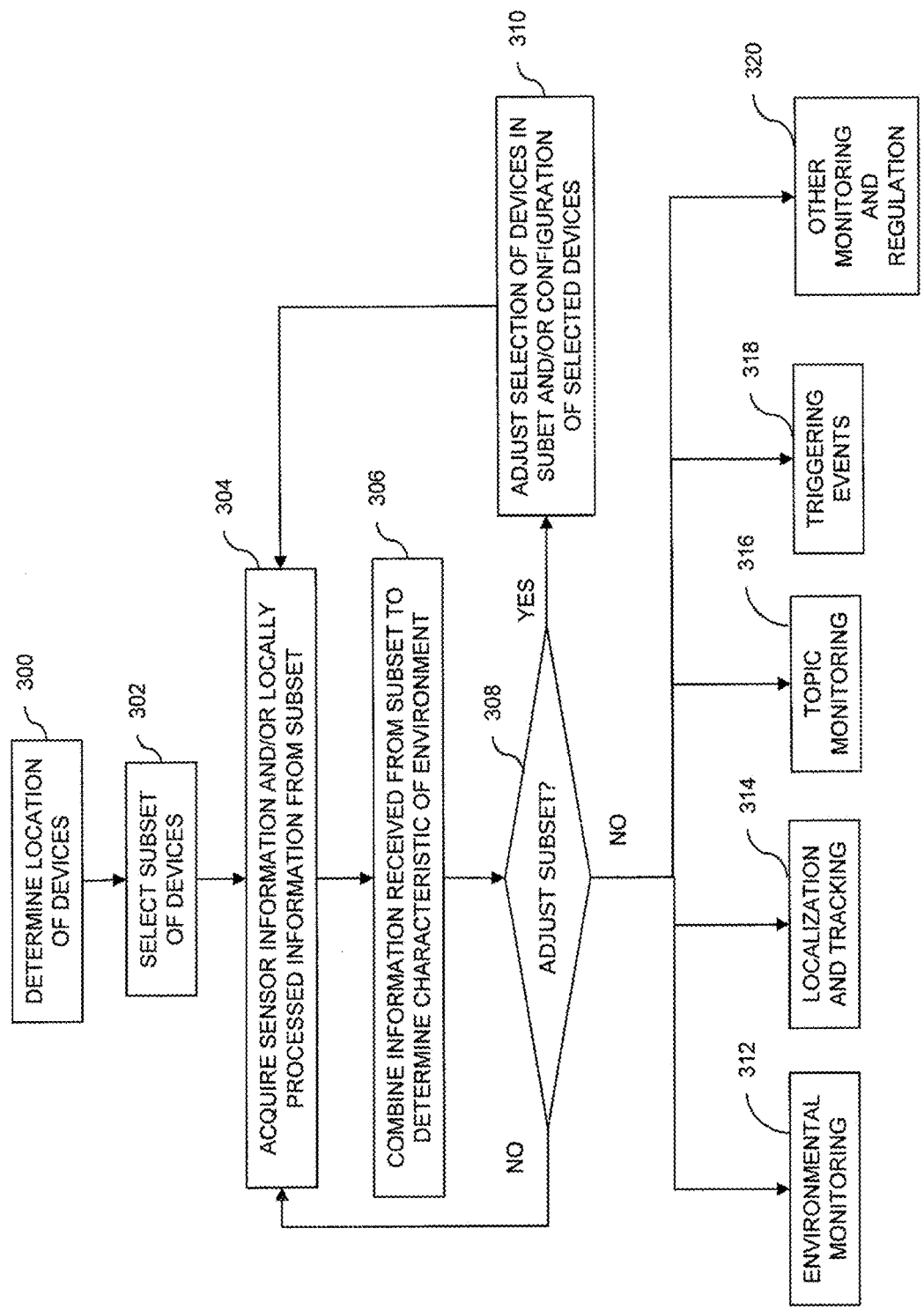
FIG. 3 is a flowchart diagram of an exemplary method for processing information from a plurality of distributed devices, according to an exemplary embodiment of the present invention.

Referring to FIG. 3, a flowchart diagram of an exemplary method for processing information from a plurality of distributed devices is shown. The steps illustrated in FIG. 3 represent an example embodiment of the present invention. It is understood that certain steps may be performed in an order different from what is shown. It is also understood that certain steps may be eliminated.

At step 300, the location of devices 120 (FIG. 1) may be determined, for example, by controller 120' based on information previously received from devices 120. For example, controller 120' (FIG. 1) may directly communicate with devices 120 to determine their locations. As another example, the location of devices 120 (FIG. 1) may be known from communication with communication system 150 and/or sever 140.

At step 302, a subset of devices 120 (FIG. 1) may be selected, for example by device selection/data acquisition module 240 (FIG. 2B) of controller 120'. For example, controller 120' (FIG. 1) may select one or more devices 120 based on a predetermined characteristic of the environment and the location of devices 120.

At step 304, sensor information and/or locally processed information may be received by controller 120' (FIG. 1) from the selected subset, for example, by device selection/data acquisition module 240 (FIG. 2B). For example, controller 120' (FIG. 1) may receive raw sensor information from respective sensor modules 202 (FIG. 2A) and/or locally processed information from respective local data analysis modules 204 (FIG. 2A). Controller 120' (FIG. 2B) may also acquire sensor information and/or locally processed information from its own sensor module 202 and local data analysis module 204. The information from at least one of the devices 120 may be received responsive to a confirmation indication from the respective device 120, to indicate an allowance by device 120 to release its respective information to the controller. For example, the confirmation indication may be provided manually by a user of the respective device 120, or may be provided automatically by the respective device 120, based on the privacy settings of the device 120.

At step 306, information received from the subset (as well as, optionally, from controller 120' (FIG. 1)) is combined to determine a characteristic of the environment, for example, by scene analysis module 242 (FIG. 2B) of controller 120'.

At step 308, it is determined whether the subset should be adjusted, for example, by device selection/data acquisition module 240 (FIG. 2B) of controller 120'. For example, the subset may be adjusted based on an event detected by a local data analysis module 204 (FIG. 2A) of one or more devices 120, the characteristic of the environment, any context from the characteristic, the location of devices 120 (FIG. 1) (e.g., position, orientation in space), demographics from the characteristic, any social-graph membership among devices 120, etc. For example, if one device 120 (FIG. 1) detects a gunshot, device 120' may expand the subset of devices 120 to additional devices (to triangulate the location of the gunshot) and/or to send a warning indication to all devices 120 in range.

If it is determined, at step 308, that the subset should be adjusted, step 308 proceeds to step 310. At step 310, selection of the devices in the subset may be adjusted and/or a configuration of selected devices of the subset may be adjusted, for example, by device selection/data acquisition module 240 (FIG. 2B). For example, different devices 120 (FIG. 1) may be switched on or off. As another example, different sensors of sensor modules 202 (FIG. 2A) may be configured to acquire sensor information.

If it is determined, at step 308, that the subset should not be adjusted, step 308 may proceed to step 304, to continually determine a characteristic of the environment.

Alternately, step 308 may proceed to step 312 (environmental monitoring), step 314 (localization and tracking), step 316 (topic monitoring), step 318 (triggering events) and/or step 320 (other monitoring and regulation). The characteristic of the environment may be used for a number of different applications, which are described further below.

Referring generally to FIG. 1, in an exemplary embodiment, a platform may be developed to enable users to develop applications that: harness a set of these devices 120; acquire signals from devices 120; switch subsets of devices 120 on or off (based on information about context, including position, orientation in space, social-graph membership, and demographics); process and analyze information obtained from sensors of devices 120; set triggers to enable or disable sensing, processing or analysis; and adapt system 100 to sensed, processed or analyzed information. The platform may allow individual devices 120, 120' to be customized and personalized to users (consumers) to mitigate, amplify or pass-through acoustic and other information to users based on acoustic and other information acquired from one or more devices.

Once such a platform is developed, applications may be developed for many of the scenarios and use-cases described herein. The platform may specify minimum hardware requirements, such as minimal sensor numbers and configuration, minimal onboard computing resources in terms of hardware and software, and an application programming interface (API) to allow developers to access all the features and resources available on the device.

An example platform specification may include: one or more microphones or a microphone array; one or more accelerometers typically to cover two or three axes of motion or orientation; a compass; an on-board GPS system; zero or more other sensors such as contact or non-contact temperature sensors; cameras with a minimal required resolution, with Bluetooth®, Wi-Fi and other capabilities; software including classifiers to analyze speech, to analyze media including music, video, and still images; software to acquire environmental metrics and analyze them in various contexts such as urban vs. suburban, and residential vs. industrial; software to preprocess signals acquired to remove or reduce noise, filter the remaining signals to identify high value signals and to transmit them to a server 140 in a compressed form if desired; a database of sound signatures; and software to handle reactive mechanical tasks in response to sensor data—all with enough power to provide a realistic and acceptable user experience.

2.0 Example Use Cases

In this section, a number of example use cases are provided to illustrate how an exemplary system 100 (FIG. 1), described above, may be used in practice.

2.1 Environmental Monitoring

A number of uses relate to monitoring an environment of a set of smartphones. In a public health monitoring example, the on-board audio processor may be configured detect occurrences of coughs, typically by the owner of the device or by other people in the proximity of the device. Such detection may use, for example, statistical spotting techniques (e.g., Hidden Markov Model (HMM) techniques, Gaussian Mixture Model (GMM) techniques) trained on a corpus of recordings of coughs know as a Universal Background Model. Communication of locally aggregated results, for example, a number of coughs per hour, may be uploaded to the central server 140 or device 120' on a schedule, or when the rate deviates from an expected or maximum value. In this way, the controller 120' (or server 140) may be able to identify local "hot spots" of coughing.

Other educational and public health uses may be possible with epidemiological applications of such systems. For example, pertussis (whooping cough) is a highly contagious disease and one of the leading causes of deaths world-wide that is preventable with the use of vaccines. Exemplary system 100 may be used to provide information to parents of children with coughs or with other symptoms such as asthmatic symptoms to help them decide when to seek medical help, and to provide epidemiological data about pertussis, asthma and related illnesses.

In some scenarios of such monitoring, only a limited subset of devices may be initially configured to perform the local processing needed to detect the coughs. However, when controller 120' determines that there is a possible hot spot of activity, controller 120' may enable further devices in the geographic proximity of the hot spot to gain further information about the extent of the situation. In some examples, the controller 120' may enable further devices based on a social proximity, for example, to account for the possible transmission of an illness to others that are close in a social sense. In addition to enabling further devices, the controller 120' may disable devices and control the overall monitoring set for the task.

In a variant, the system 100 may use sensed information to alert patients to asthmatic attacks in children, along with information on the child's environment at the onset of the attack, to enable them to ensure that prompt remedial or palliative action is taken.

In yet another variant, the system may be used to alert patients of breathing disorders such as sleep apnea. Sleep apnea is a disorder that is characterized by abnormal low breathing or abnormal pauses in breathing during sleep, often accompanied by snoring. Often the snorer is not aware that they snore or that they could have a life threating medical issue, and they suffer from fatigue, daytime sleepiness and other symptoms, often for years and years. Diagnosis often requires an overnight sleep study in a special lab set up with sensors. Knowledge about snoring and having a record of snoring behavior can help in the diagnosis and remediation of this condition. System 100 may be trained to recognize snoring, and to distinguish it from other kinds of similar noises, and help in detecting and recording snoring behavior to help people with breathing disorders identify their problems and seek appropriate help.

In another monitoring use case, the devices 120 may be used to monitor environmental sound levels (e.g., sound pressure level), for example, for workers in a factory workplace. Devices 120 of workers monitor the noise level and maintain a record, for example, cumulative durations of various ranges of noise level. This locally-determined information may be provided on regular or locally triggered basis, for example, if the noise level exceeds certain prescribed limits (e.g., an absolute limit, a limit for accumulated time above a prescribed sound pressure level, etc.). The controller 120' (or server 140) may query further devices 120 to determine the location of high noise levels, for example, based on locally logged detailed information that correlate noise level and location within the workplace. Also, other characteristics of environmental sound, for instance, related to the source of the sound may be detected. For example, a machine type (e.g., whistle, engine, press, saw, drill etc.) may be discriminated, for instance using pattern matching techniques (e.g., HMM, GMM techniques).

A similar sound-level monitoring may be used to track environmental sounds levels, for example, in particular restaurants, on particular streets, etc. and such monitoring may also identify time-of-day variation of such levels. Ornithologists may be interested in the ability to monitor the presence or absence of bird songs over time and space. Others might be interested in using sound arrays to monitor insect infestations. Exemplary system 100 may make it possible to compare treatment areas with controls to measure the effectiveness of proposed countermeasures. In some examples, if the device 120 is not connected to the communication system 150, information is logged, time stamped and stored in a non-volatile memory and then uploaded when the device 120 is once again connected or its memory is interrogated. This may be typical after an automobile accident or other fatal or non-fatal incidents.

If a large number of cars on the same highway suddenly decelerate at the same time, then the network could decide to issue a warning to cars a few miles behind the obstacle. In addition, the ability to measure traffic flow using an array of smartphones (equipped with communication networks and sensors such as accelerometers and microphones and GPS/location sensors) has the potential to improve traffic routing in the short term, and traffic planning in the long term. Many of the applications envisioned in the present invention may have both short-term and long-term benefits. Short-term benefits use networks with low latency (such as the radio stack), whereas long-term applications can make use of networks with longer latency (such as uploading information at the end of the day when the device is docked in a networked cradle).

In another monitoring use, phones may be enabled to "name that tune" in the environment, and both provide the owner to download that song to their device library and upload the location of the playing to the central controller, which monitors the aggregated presence of different songs. Consider a music festival with several stages, where different groups are playing. As the user walks around these stages, a network of systems may be continuously acquiring audio data, detecting and isolating, for instance, music, identifying the music and showing users the name of the piece being played, the album, the artistes playing etc. The system may provide a mechanism for users to purchase the music if it is of interest to them. There are stand-alone programs to identify music being played, but they require a single device to collect a good sample of music, send it to a server and then possibly identify the music. In contrast, by having a network of devices 120 collect data, data acquisition is more robust and distributed, and users are able to get their music identified faster.

Detection of particular music being played in the environment of devices may be aggregated to determine marketing related information. By monitoring what people hear as they go about their lives, the system may acquire considerable information about the media segment. The information captured on music played, the artiste/group being played, the volume of music purchased etc. is very valuable, especially when pivoted on various dimensions. In addition, in stores where music is sold, features such as the audio background and lingering behavior may also be valuable.

These devices may also be used to share information about what users listen to or see, or to find out what their friends are seeing or listening to. Currently users have to take the effort to tweet or post their music-playing or video-watching behavior. However, a few days of this can get tedious, and soon users may no longer post information on their listening or viewing habits. Exemplary devices 120 may automatically identify songs or TV programs, inform friends in the users' social graph or create virtual communities of users with similar listening or viewing interests.

2.2 Localization and Tracking

Some use cases take advantage of the multiple locations of the devices 120 to perform localization and/or tracking of audio sources. In one example, aircraft noise data may be obtained by having a "jet detector" implemented in the on-board audio processor of a set of devices 120. Upon detection of a loud jet noise, which is reported to the controller 120' (or server 140), other devices 120 in the proximity of the reporting device(s) 120 are enabled. Buffered time stamped audio and device location data is uploaded to the controller 120' (or server 140), where a triangulation approach may be used to determine a track of the detected audio source. Based on the track, further devices 120 may be enabled along the project track so that the audio source may continue to be tracked. If the source is lost (i.e., doesn't follow a predicted tract), more devices 120 over a larger area may be enabled to re-acquire the location of the audio source. In this way, an overall assessment of the audio tracks of loud aircraft may be determined based on the aggregated acquired audio data.

The selected set of devices 120 effectively acts as a configurable microphone mesh for acquiring audio data. In other examples, the devices 120 can act as a configurable accelerometer mesh for acquiring spatially and/or temporally distributed motion-related data.

Similar tracking information may be used, for example, to track sirens in a city. Such tracking may be used, for example, to predict traffic flow in a city that may be affected by an emergency.

Another type of localization may be used in near real-time or in an after-the-fact forensic mode. For example, the devices 120 may be carried by police officers or bystanders near the scene of a shooting. After detection of a gunshot event by one or more of the devices 120 (e.g., the officers' devices), the controller 120' (or server 140) may upload locally buffered audio from the officers' devices 120 or other devices 120 in the environment, and perform a localization of the source of the shooter's location. In a near real-time example, this information may be provided to the police officers to aid in their police duties. A similar type of arrangement may be used in a military situation in which audio is buffered at devices 120 carried by multiple soldiers, and the combined information may be used to estimate the direction of a sniper location.

Note that a central server 140 is not necessarily required. For example, devices 120 may locally exchange information to perform aggregated analysis, such as localization. In one such example, each device 120 may include a detector for an event of interest (e.g., gunshot), and upon detection of the event may pass the raw audio or a partially processed version of the audio (e.g., an intensity time profile) to nearby devices 120 (e.g., using ad hoc wireless communication), which perform local assessments of shooter direction based on the information they obtain.

In yet another scenario, these devices 120 may be used for adaptive crowd control. In situations with high traffic, whether vehicular or pedestrian traffic, these devices 120 may be configured as a mobile ad hoc network to estimate traffic flow from noise, with no requirement for any fixed or embedded sensors. Using the dynamically acquired traffic pattern information, the system 100 may broadcast instructions though the devices 120 or through other means to direct people through paths of lower traffic density, open up different gates or paths, or use sonification or acoustic visualization to alert users to high traffic versus low traffic paths.

A related idea is to create mobile sound-based security systems where the system 100 is able to quickly learn about ambient conditions and sound trends, and use this to signal situations away from normal conditions.

In another use case, these devices 120 may use sentiment detection and emotion detection to identify centroids of trouble in large crowds. A variant of this system 100 can be used to detect user dissatisfaction in their language, or in non-speech audio to alert management to, for example, open more counters in stores.

When users try to meet up with friends in large auditoria or sports stadia, it is often impossible to use mobile phones or to hear conversations on phones. The system 100 may use knowledge of users' social graphs to indicate the presence of friends using directional sonic visualization or sonification, with some variation in tone or volume as users approach their friends. Using the peer to peer architecture of the system 100 along with the knowledge in each device 120 about its neighboring devices 120 and their features, the system 100 can quickly and effectively determine the possible locations of friends. By utilizing the position information, and the orientation information acquired from the user's device 120, the system 100 can provide differential tones, volumes or other signals to indicate whether the user is moving towards or away from their friends (and whether they are pointed towards or away from their friends), and provide an indication about how far away they are. The precision of this indication may go up with the number of peer devices 120 contributing information to the system 100.

In another localization use case, a number of devices 120 may be enabled to sense audio, for example, for a group conference call. The locally acquired audio may be used to identify the location of the speaker, and to control which device 120 (or devices 120) are used to generate the audio for the call. For example, a device 120 closest to the person speaking, or the device 120 providing the highest signal quality or intelligibility, may be selected, thereby providing an improved audio quality.

In another localization use case, devices 120 may be tracked during a shopping trip, for example, in a grocery store or at a mall. The track taken by the user with corresponding audio or video information may be used to identify areas of customer focus and interest, and provide user-specific information, for example, promotional information related to purchase opportunities in the vicinity of the device 120.

After-the-fact analysis of a track may be used to correlate movement with actual purchases made, or to possible interest in various classes of items. For example, a relatively high time spent in the vicinity of a product type may indicate an interest in that product type. Users may be interested in opting in to having their path tracked in exchange for receiving promotions 2.3 Topic Monitoring In another use example, a device 120 may be enabled to monitor the owner's environment as they converse during the day, and as they listen to media broadcasts. Topic detection techniques, for instance, based on spotting topic-related keywords, may be used to assess topics of interest to the user. During the day, or in a periodic summary, the user is presented with collateral information related to the topics. For instance, if the user enters into a conversation about a particular topic, recent news or background material may be offered on the device 120. Such topic monitoring may also be useful to provide other targeted material to the user, for example, in the form of advertising that is relevant to the user's interests.

The configuration of other devices 120 may be adapted based on what is detected at the user's device 120. For example, other devices 120 in geographic or social proximity to the user's device 120 may be configured to detect the presence of similar topics. In this way, the other devices 120 may have a higher likelihood of correctly detecting the topics. Furthermore, the controller 120' or server 140 may be able to track the extent of interest in a topic.

Another topic-related monitoring use may be related to a third party requesting detection of audio signals, such as audio components of advertising to determine where these advertisements have been played. For example, an advertiser may have controller 120' or server 140 configure devices 120 to detect an advertisement, and then determine where the advertisement has been played and potentially heard.

In a related use case, the system 100 may use information garnered from the sensors of devices 120 and from other sources such as electronic program guides (EPG) to identify what programs users have been listening to or viewing, to get Nielsen-like viewership statistics or to acquire business intelligence. Current systems tend to rely on home systems or manually created diaries, both of which are prone to error. Using exemplary devices 120 and exemplary system 100 may allow for this monitoring to be done wherever the user is, and whatever media device they use, and to use information from user activity to distinguish active listening or viewing from, for instance, a TV playing to an empty room.

2.4 Triggering Events

Generally, use cases described above use various triggering events to begin local logging of audio and/or to initiate communication with the server 140, device 120' and/or other nearby devices 120. In addition to audio-based events (e.g., specific words, spoken topics, music, sounds, etc.), other events may trigger monitoring and/or communication. For instance, content of text communication (e.g., Short Message Service (SMS) messages) may initiate monitoring and/or configure what is to be searched for. Other data, such as accelerometer data, biometric data, and detection of a video image (such as change in luminance, etc.) that is available to the device may also be used in a trigger. For example, high acceleration may be associated with a vehicle accident or a fall, and this may initiate audio monitoring or communication with the server 140 (or device 120'), which may be able to determine if an accident has occurred based on the audio scene 130, in which case emergency help may be summoned.

The system 100 may also be used in the care of the elderly and the disabled. Currently senior citizens and the disabled can purchase a conventional device to signal when they need help, for example if they fall or feel dizzy. However, these conventional systems require the user to consciously make a decision and press a button on the device to ask for help. The problem is that there may be situations where the user cannot make the decision, may be too embarrassed to ask for help, may feel their problem is not critical enough to ask for help, or may not even be able to access the button to call for help. For instance when the user has a stroke or if they have a fall, it may be difficult for an elderly user to press the button. The system 100 described here may use data fusion ideas to combine speech and noise detection from one or more devices 120 along with other accelerometer data to detect calls for help, or sounds from falls, dropped objects, etc., distinguish between false alarms and real problems, and summon help when required as well. System 100 may also be able to turn on the speaker phone to have a dialog with the "help" side of the call.

In another form of triggering event, when a device 120 is removed from the direct acoustic environment, for example, by being put in a user's pocket, the change in audio signal characteristics may trigger a message to the controller 120' or server 140 to indicate that the device 120 is no longer available for acquiring audio based on a poor signal-to-noise ratio (SNR) operating environment. Similarly, when the device 120 is taken out of the pocket, it may again start monitoring the environment and/of notify the controller 120' (or server 140) that it is once again available. In addition, when the device is no longer obtaining adequate SNR, the device 120 may be able to enable other devices 120 within its proximity to acquire the signal and thus improve the overall SNR. In addition, many devices are now manufactured with multiple microphones (primarily used for beam forming) as to obtain an improved SNR for the user. As the user may often carry the device 120 in their pocket or purse, system 100 may be able to select which microphone in the device 120 is desirably enabled or what beam forming array would be best evoked to obtain a maximum SNR In some examples, vehicle texting is disabled by the system 100. By detecting an acceleration signature consistent with being in a moving vehicle and/or by picking up the type of sounds picked up while driving, the device 120 can detect road noise, the engine noise, wheel bearing noise, breaking noise All of these sounds may be used to either disable or enable the user from utilizing their device 120 for texting while the car is in motion. The device 120 may query its proximity and determine if other devices 120 were present within the body of the automobile. Assuming the answer were yes, further analysis may be used to provide limitations on the driver's device 120 from texting while still allowing the balance of the individuals to text. Some cars also disable or limit select navigational controls for safety reasons when the car is in motion. If the device 120 is able to detect a front seat passenger, the system may choose not to limit navigational controls.

In some examples, key word spotting obtained from in-situ conversations is aggregated from both the sender and recipient. During the course of normal telephone conversations, the device 120 may identify specific sounds, words, etc. being uttered by both parties of a conversation. The system 100 may interrogate these sounds and provide the user with information either thru a graphical user interface (GUI), or audio based or text based feedback. As an example, assuming a call was about a trip to Paris, the device 120 could render information about promotional pricing on an airline to Paris.

One or more of these devices 120 may be used to identify trends in audio and other information acquired by these devices 120, for example using keyword spotting in audio streams. Keyword trends may be used to adaptively mediate or modify information consumed by users. In one scenario, information sources such as news media, search engines and similar information outlets may acquire information on trends from individual users or groups of users, and show different items to different users based on keyword trending. Specifically such a system 100 may choose topics users have been known to prefer.

Trending on non-speech audio may be used to identify patterns of people flow or vehicular flow. Aggregated logs of speech and non-speech audio may be used for a number of diverse applications, including identifying less noisy apartments or houses to rent or buy and areas of hotels or theater halls that may be better soundproofed. Longer term trending and identification of trends and periodic variations may be used for soundproofing or weatherproofing offices and residences.

2.5 Other Aspects and Uses

The ability to aggregate information over many smartphones can be provided with or without the cooperation of the carriers. It could be done, for example, with a third party application, which doesn't need the approval of a particular carrier and communicates via Wi-Fi or Bluetooth®. In this way, information can be aggregated across phones serviced by multiple competing carriers.

In some exemplary embodiments of the system 100, the system 100 may trigger off key events such as rapid deceleration of several cars at the same time and place, sirens, keywords, etc. The ability to collect vast quantities of data may improve the triggering capability. Search companies are providing better search relevancy than ever before, largely because they are collecting more data than was possible before, the popularity of modern search engines. But with the exemplary system 100, it may become possible to collect even more data. If every phone were collecting audio, biometric, environmental data for an hour a day, the aggregate data resource would be much larger and much more valuable than the data collections currently collected by even the largest search companies.

In some exemplary embodiments of the system 100, if a device 120 in the system 100 may detect certain important keywords and phrases like "fire," then the system 100 may respond appropriately. The importance and urgency of a term depends both on the consequences of inaction as well as term weighting concepts that are well known in the field of Information Retrieval.

Similarly, if a system 100 hears an important term (such as a keyword like "fire" or a non-word like a cough or an event picked up on some other sensor of device 120 such as a rapid deceleration), then the system may turn on numerous other nearby sensors in the array to confirm the event, to improve the signal to noise ratio and/or to localize the event in time and space.

In some uses, trending analysis may use the large amount of data available through the system 100. Consider the cough example mentioned above. Aggregations of coughs over time and space may provide tracking of health over time and space. The approach is similar some approaches to prediction of the flu based on queries where they showed that they could predict flu a couple of weeks faster than the Centers for Disease Control and Prevention (CDC). But the proposed cough metric should have even better resolution over time and space since it is based on a larger quantity of sensed data.

Collection of large amounts of sensed data provides a way to systematically predict (e.g., according to a statistical model) sequences or sets of sensed events of other information. Such prediction may effectively be exploited based on principles related to Shannon's Noisy Channel Model, for example, to improve transmission capacity for such events. For example, such data can allow one to create a better "language model" for events, which will do a better job of predicting what sounds to expect to hear (the prior for the noisy channel model) as well as sounds that are anonymous (triggers that should sound alarms and start recording).

In some examples, workplace monitoring (and monitoring of the environment) may be enabled by the system 100. The system 100 may effectively provide "smartdust" on smartphones, which is able to monitor workplaces for health issues by measuring acoustical events like coughs. Moreover, in some uses, the system 100 may sense correlates of stress such as noise. Some call centers, for example, have more stress related illnesses because the call volume has relatively large numbers of unhappy customers. It may be possible to predict risk of certain types of illnesses well before symptoms develop, both at work as well as elsewhere.

An ad hoc network of devices 120 may be used to fine-tune a number of features. Consider concert-hall acoustics, for instance. Concert halls are typically tuned for the major uses of their space. For example, a symphony hall may be tuned especially for a large group of artistes and their instruments, and may not be as well suited to, for example, solo vocalists. Sound quality in a hall is also dependent on the size of the audience, their ambient noise characteristics etc. The network of system 100 may enable data to be acquired from a large number of devices 120 in the audience, so that the hall management can adapt to the ambient noise levels and fine-tune sound levels for any performance, with any number of performers and instruments, and with different audiences.

The ad hoc network can also be used for monitoring and regulatory purposes. Sound pressure levels or similar measures of rock concerts, gym classes and other potentially noisy environments may be monitored against safe listening levels, and infractions reported to the appropriate management or regulatory agency.

A similar scheme may be used to fine-tune the temperature in large auditoria, rooms or halls, based on data acquired from a number of devices 120 and individual sensors in that space. Large spaces have their own airflow and heating and cooling patterns, based on placement of air ducts, windows, doors and other openings. Heating and cooling is typically based on measuring temperature in one and occasionally more sensing locations. If the sensor is near a sunny window or a draft caused by a constantly open door, the temperature in that space can be unsatisfactory. By measuring temperature in several locations using a set of devices 120 as described in this invention, it will be possible to have finer, more localized control of temperature.

Some exemplary embodiments of the system 100 may make predictions based on a small sample of "opt ins." The system 100 (e.g., "cloud") may be equipped with appropriate logic to determine how to make appropriate inferences based on information gathered from those phones 120 that choose to opt into the system 100. Many of these inferences are relatively straightforward, though care may need to be taken to account for the fact that the sample is not a random sample. The set of people that own a smartphone and/or other wearables and choose to participate will be skewed toward certain demographics, at least in the near term.

3 Backup Communication Uses

In some versions of the system, the mesh-like features of the set of personal devices 120 may be exploited. Cell phones may be viewed as relatively passive (receive only) devices, but there are times, such as during an emergency, where it could be desirable to be able to deploy an active communication network very quickly as an overlay to more traditional telephone and internet networks.

During an emergency such as a man-made event like 9/11 or a natural disaster such as a major hurricane, it is possible that parts of key communication infrastructures could be down. There was a time when telecommunication networks were much more protected than they are these days. The telephone network used to be more reliable than the power grid. Central offices are typically backed up with batteries and generators (and submarine doors in places like New Orleans that are subject to flooding). Plain old telephone service (POTS) handsets used to be powered from the central office, so the service could stay up even if the standard power grid was down.

These days, most handsets sold in popular stores depend on the power grid. Most phones have lots of features and a power cord. Some have battery backup, but there is little incentive to replace the battery. Soon, the battery backup feature may be a thing of the past because many people aren't willing to pay for such features. Engineers like to design bridges for the hundred years' flood, but it is hard to persuade customers to pay for features they probably won't use. Given these realities, it is desirable to develop a way to deploy a backup network just-in-time. Unlike batteries and generators, which are expensive whether we use them or not, a backup network based on phones typically won't cost the public much if any additional capital, because most of the equipment is already in place.

Key Features of a Backup Network:
1. Two-way communication: Telephone receivers normally receive but they can also be used to store and forward information. Thus, for example, if a phone was on a mobile platform (say in a pocket or in a car), then the phone could be used in sneakernet mode to store a signal in one place and repeat it from another place.
2. Damage Assessment (the ability to determine quickly and easily what is working and what is not): During 9/11, there were many outages (e.g., fiber cuts under #7 World Trade Center, cell towers on the rooftops, switches under both #1 and #2 World Trade Center, police and fire radio communication in certain places), but some things were working (e.g., cell towers in New Jersey, BlackBerry™ email, systems based on satellites). A key requirement is to determine what is working and what is not, and to communicate workarounds to those that need them. An array of cell phones in a multitude of pockets and cars could determine fairly quickly what is working and what is not. Hopefully, some of these devices may be connected to something that is working (such as a satellite) or would eventually move out of the affected area so enough of them could report an accurate and timely damage assessment picture back to the cloud. Using this information, both digital and real world traffic may be adaptively rerouted.

3. Workarounds: Municipal vehicles such as buses have batteries and generators. Soon, such vehicles may also have Wi-Fi that is connected to satellites. The cloud could direct such resources where they are needed most.

An acoustical array, such as what is described herein, may also be used in damage assessment. For example, the acoustical array may determine both whether there is too much noise (e.g., explosions) as well as too little noise (e.g., absence of human activity), aggregated over time and space.

4 Authorization and Privacy

In some exemplary embodiments of the system 100, privacy considerations may be addressed using one or more features, which may include the following. First, monitoring may be enabled on a device 120 only if the user explicitly "opts in" to permit particular monitoring options. A reason that a user may accept such monitoring is that he, in return, obtains information that is valuable to him, for example, by being provided more relevant search results or other information. Another feature relates to encryption of the monitored information. For example, audio may be encrypted in a manner than prevents interception during uploading and/or processing by a controller 120' or server 140. Furthermore, in systems 100 in which multiple central controllers are used (e.g., one controller 120' or server 140 per cellular telephone carrier), the user may explicitly permit sharing between or among controllers.

In some examples, devices 120 may have features that inhibit collection of audio environment data. Such features may be mechanical (for example, mechanically preventing audio pickup with a shutter mechanism) or can be electronic (for example, with an electronic slider switch on the device).

In some examples, sensors can be selectively turned on or off both at the edge of the network (in the smartphone), as well as in the network (in the cloud), as well as elsewhere. For example, the operator of a movie theatre may have the ability to turn off speakers that would annoy others in the movie theatre, and similarly the operator of an airplane should have the ability to turn off communication features that could jeopardize the safety of fellow passengers. Moreover, after an incident, such as a plane accident, the authorities should have the ability to probe (via a wired or wireless interface to the memory of the phone-could be non-volatile) the smartphones on the plane for information that could be helpful in the investigation. In other words, the array of smartphones on the plane could serve as a kind of "black box" to prevent similar such incidents in the future.

However, privacy is also important in at least some versions of the system 100. In some exemplary embodiments, the owner of the smartphone should have the ability to pull the curtain with confidence that the phone is not invading the user's privacy, even if the phone has been taken over by a virus. When the curtain is pulled, the user wants to be sure that the phone is not recording information that could be embarrassing or self-incriminating. The phone should not be recording information that could be subject to subpoena or a court order such as discovery. The user should have the ability to opt out in a way that cannot be overridden by the owner of the network, government authority, or anyone else (such as a malicious hacker). For example, privacy may be implemented by a switch, as described further below.

Feature interaction can be a tricky problem in a communication network. While it is desirable that many parties have the ability to turn on and off certain features in certain ways, as discussed above, it is also important that it be clear to all parties what happens when different parties issue commands that may conflict with one another in complicated and unanticipated ways.

In particular, in at least some exemplary embodiments of the system, the owner of the phone ought to be in charge. In such embodiments, the owner may have the ability to physically disconnect the sensors in a way that cannot be overruled by any other party. One such method may include a physical switch that would disconnect the sensors in a way that the user can verify by visual inspection of the phone. The physical switch may be operated manually by the user and cannot be overridden remotely under software control.

In addition to the physical switch, there may also be a software controlled switch that may empower authorized parties to turn on and off features such as recording of sensors, recognizing keywords and uploading appropriate information to the cloud where inferences can be made that aggregate over space and time. Policies may eventually be determined regarding who is allowed to do what, and what is appropriate and what is not.

5 Other Devices

As introduced above, the exemplary approaches described above are not limited to smartphones. For example, in-vehicle systems (e.g., navigation devices), media devices (e.g., televisions, set-top boxes, desktop computers, laptop computers), and other fixed or mobile devices may be used in similar ways. For example, in the case of an in-vehicle navigation system, an in-vehicle conversation may be monitored and information about a location (e.g., a restaurant) that is being discussed may be provided on the device's display.

Another type of device that may be used in such a system is an earpiece that provides audio input and output for a telephone (device). An advantage of monitoring with the earpiece is that it is exposed to the acoustic environment even when the associated phone is not exposed to the environment, for example, when the phone is in a user's pocket, thereby providing an improved signal-to-noise ratio (SNR). Another embodiment may have the entire mobile communication (cell phone) being integrated into the earpiece.

Another type of device 120 that may be used in such a system 100 is a hearing aid. The hearing aid may allow the entire feature set thus described in herein to be made practical. The advantage of this is data which could be mined from this age population is thought to be very different for the generation of users who typically use headphones for their communication activities.

Use of earpieces as described above can be thought of as ownership or control of the "last inch," which is similar to the ownership of the "last mile," which has been strategically important in the telephone business. The same dynamic underlies the debate over net neutrality. So too, ownership over the last inch will become strategically important in the war over eyes and ears. The web is currently about eyeballs and mouse clicks, but soon the war will move to a struggle for access to ears as well as eyes. The hearing aid or earpiece could be viewed as a chief of staff. It gets to decide what the user hears and what the user doesn't hear. The hearing aid could give the wife preferred access. It could also block spam, and filter out unwanted commercials. Alternatively, the hearing aid or earpiece could run an auction similar to a paid search, where the hearing aid is a market maker that attempts to find an equilibrium between the need of the user for relevance and utility to the advertiser.

These auctions typically use a Vickrey auction to encourage advertisers to bid their true utility. If the user chooses to follow up on an ad (with a mouse click), then the advertiser pays the second highest bid. The hearing aid or earpiece could work in a similar way though, perhaps, instead of clicking on an ad, it might be easier for the user to participate by some other means such as a spoken command.

Although the invention has been described in terms of systems and methods for processing information from a plurality of distributed devices, it is contemplated that one or more steps and/or components may be implemented in software for use with microprocessors/general purpose computers (not shown). In this embodiment, one or more of the functions of the various components and/or steps described above may be implemented in software that controls a computer. The software may be embodied in non-transitory tangible computer readable media (such as, by way of non-limiting example, a magnetic disk, optical disk, flash memory, hard drive, etc.) for execution by the computer.

For example, some of the software may include instructions for execution at the personal devices 120 and device 120'. This software may be stored on a non-transitory tangible computer readable medium at a central location, for example, at a server 140 for distribution to the devices 120, 120', may be transferred over a digital communication medium, and/or stored in a machine readable medium at the devices 120, 120' (e.g., as downloaded applications/applets). Some of the software may be hosted at central servers 140 (e.g., in a distributed "cloud" of processors) and made accessible by storing it on non-transitory tangible computer-readable media for execution on processors of the servers 140.

Although the invention is illustrated and described herein with reference to specific embodiments, the invention is not intended to be limited to the details shown. Rather, various modifications may be made in the details within the scope and range of equivalents of the claims and without departing from the invention.

Figure 4:
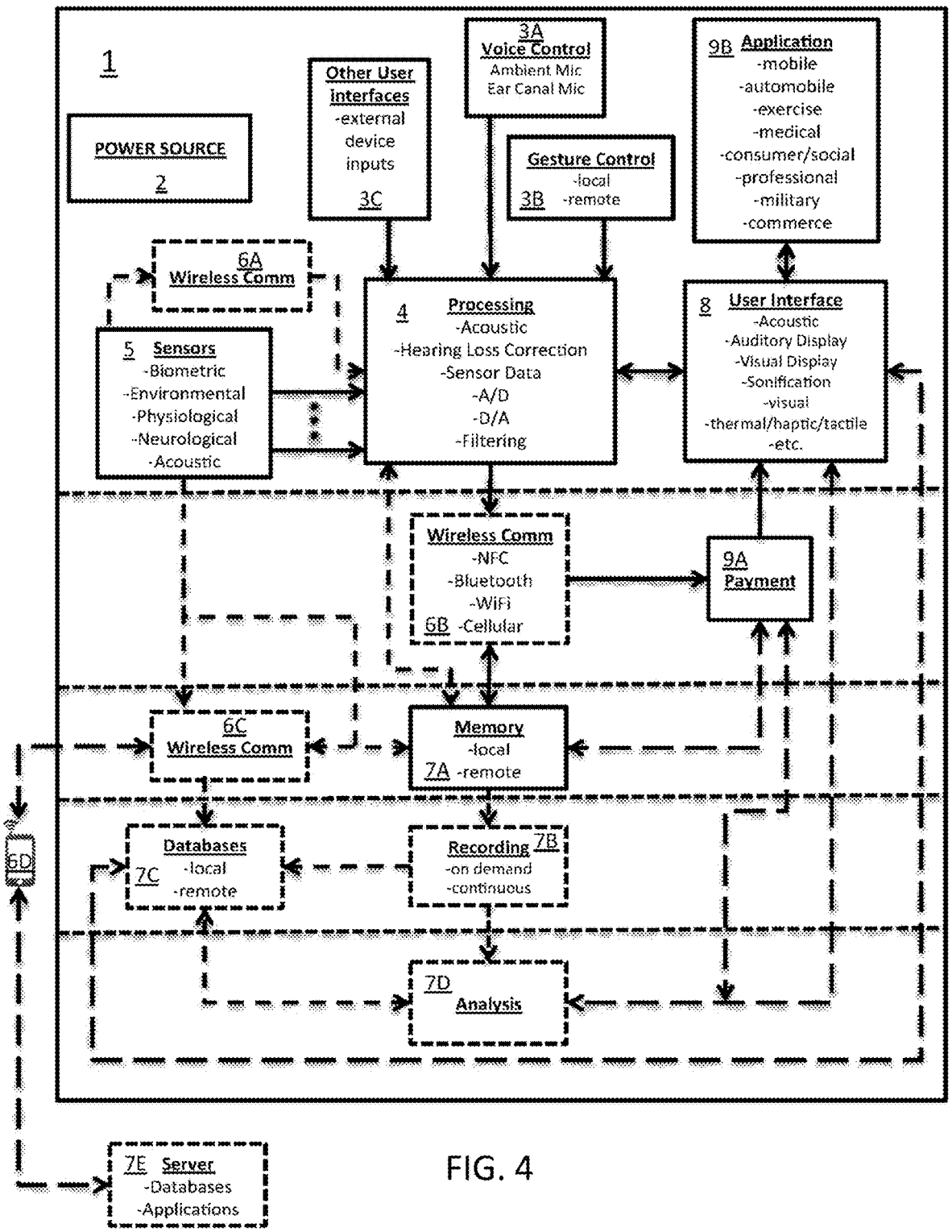
FIG. 4 and FIG. 5 are block diagrams of a telemetric devices for physiological and/or environmental monitoring and personal communication, according to some embodiments herein.
Figure 5:
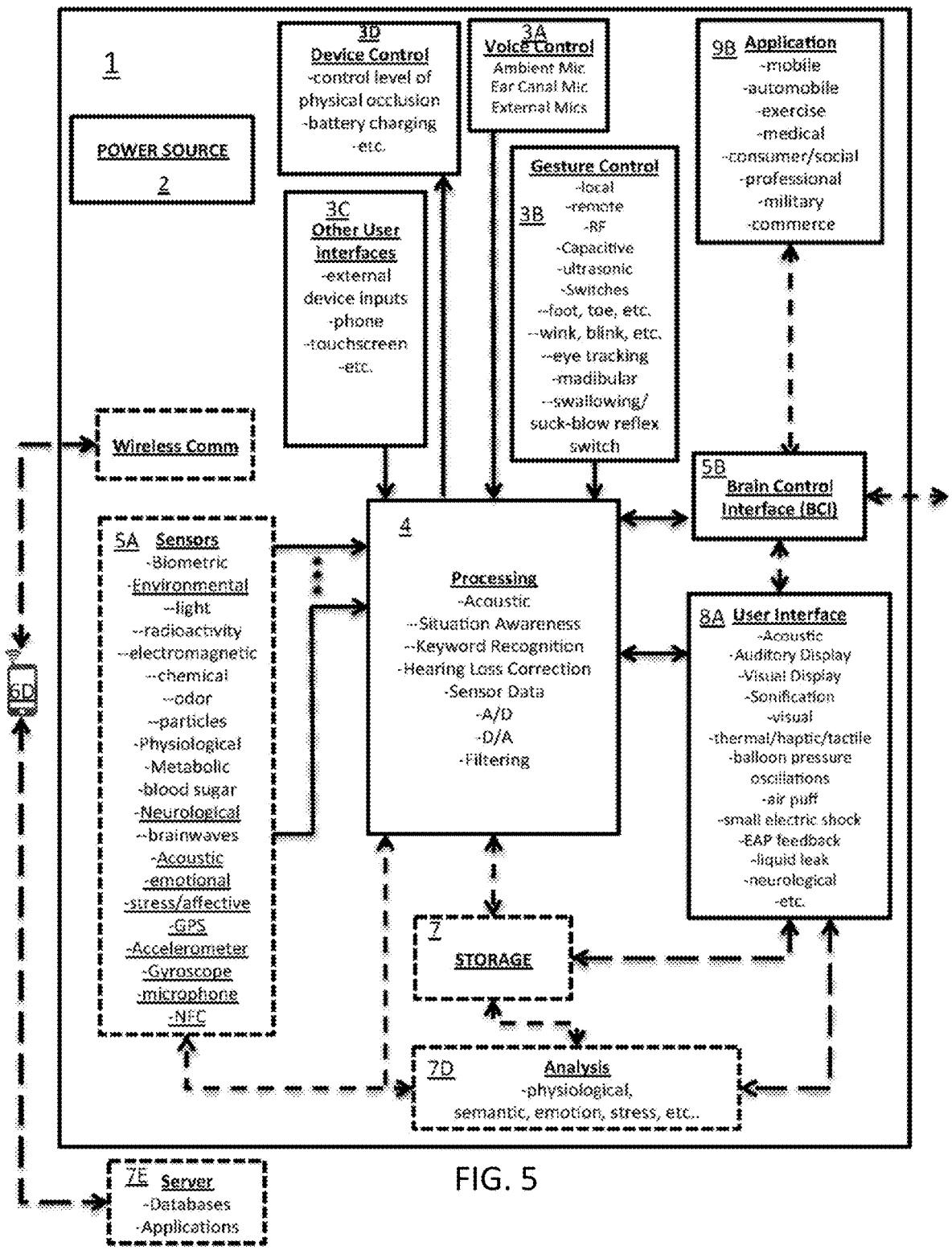

FIG. 4 and FIG. 5 are block diagrams of a telemetric device 1 for physiological and/or environmental monitoring and personal communication, according to some embodiments herein. Device 1 can be a computer, phone, earphone, watch, rings, bracelets, shoes, clothing, or any other wearable that can monitor a user (e.g., biometrics) or environment (e.g., temperature, acoustics), or could be embedded into a non-wearable, such as a book, shelves, floors, tables, etc. . . .

The device can include processing 4 capability such as from a processor, generic or DSP. The signal processor 4 provides a means of converting the digital or analog signals from the sensors into data that can be transmitted wirelessly by the transmitter 6A-C. The signal processor 4 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 4 processes signals received by a wireless communication receiver into signals that can be heard or viewed by the user. The received signals may also contain protocol information for linking various telemetric modules together, and this protocol information can also be processed by the signal processor 4 or alternatively by a remote processor or server (not shown).

The signal processor 4 may utilize one or more compression/decompression algorithms (CODECs) used in digital media for processing data. The communication modules (6A-C) can be comprised of one or transmitters that can be a variety of compact electromagnetic transmitters. A standard compact antenna can be used in the standard Bluetooth® headset protocol, but any kind of electromagnetic antenna suitable for transmitting at human-safe electromagnetic frequencies may be utilized. The communication modules (6A-C) can also include a communication receiver that can also include an antenna. In some embodiments, the receiving antenna and the transmitting antenna are physically the same. The receiver/transmitter can be, for example, a non-line-of-sight (NLOS) optical scatter transmission system. These systems typically use short-wave (blue or UV) optical radiation or "solar blind" (deep-UV) radiation in order to promote optical scatter, but IR wavelengths can also be used.

A device control (3D) can provide a level of control of device 1. For example 3D can be a battery charging system. The device can also include several user interfaces 3C, for examples a button, touch screen, touch control surface, or voice control 3A, using microphones. Additionally, the device 1 can be controlled by gestures 3B or even use electrode pickup for brain control interface 5B. In general user interface 8C can take various forms for example, acoustic, auditory display, visual display, sonification, visual, thermal, haptic, tactile, air puff, small electric current, EAP feedback liquid leak, or neurological (stimulate via electrode apportion of the brain).

In some embodiments, the transmitter/receiver (6A-C) is configured to transmit signals from the signal processor 4 to a remote terminal following a predetermined time interval. For example, the transmitter may delay transmission until a certain amount of detection time has elapsed, until a certain amount of processing time has elapsed, etc. In some cases, the transmitter/receiver is configured to transmit signals to the remote terminal dependent on information sensed by the sensors (5A). For example, if an unstable pulse rate is sensed, a warning message may be sent to a remote terminal to communicate a need for help at a particular location as determined by a GPS device operatively coupled to the device 1.

A physiological sensor (5A) can be any compact sensor for monitoring the physiological functioning of the body, such as, but not limited to, sensors for monitoring: heart rate, pulse rate, breathing rate, blood flow, heartbeat signatures, cardio-pulmonary health, organ health, metabolism, electrolyte type and concentration, physical activity, caloric intake, caloric metabolism, metabolomics, physical and psychological stress levels and stress level indicators, physiological and psychological response to therapy, drug dosage and activity (drug dosimetry), physiological drug reactions, drug chemistry in the body, biochemistry, position & balance, body strain, neurological functioning, brain activity, brain waves, blood pressure, cranial pressure, hydration level, auscultatory information, auscultatory signals associated with pregnancy, physiological response to infection, skin and core body temperature, eye muscle movement, blood volume, inhaled and exhaled breath volume, physical exertion, exhaled breath physical and chemical composition, the presence, identity, and concentration of viruses & bacteria, foreign matter in the body, internal toxins, heavy metals in the body, anxiety, fertility, ovulation, sex hormones, psychological mood, sleep patterns, hunger & thirst, hormone type and concentration, cholesterol, lipids, blood panel, bone density, body fat density, muscle density, organ and body weight, reflex response, sexual arousal, mental and physical alertness, sleepiness, auscultatory information, response to external stimuli, swallowing volume, swallowing rate, sickness, voice characteristics, tone, pitch, and volume of the voice, vital signs, head tilt, allergic reactions, inflammation response, auto-immune response, mutagenic response, DNA, proteins, protein levels in the blood, body hydration, water content of the blood, pheromones, internal body sounds, digestive system functioning, cellular regeneration response, healing response, stem cell regeneration response, and the like. Vital signs can include pulse rate, breathing rate, blood pressure, pulse signature, body temperature, hydration level, skin temperature, and the like. A physiological sensor may include an impedance plethysmograph for measuring changes in volume within an organ or body (usually resulting from fluctuations in the amount of blood or air it contains). For example, the device 1 may include an impedance plethysmograph to monitor blood pressure in real-time. Note that one or more of these physiological sensors can be incorporated within or on the expandable element or balloon.

An external energy sensor (5A), serving primarily as an environmental sensor, can be any compact sensor for monitoring the external environment in the vicinity of the body, such as, but not limited to, sensors for monitoring: climate, humidity, temperature, pressure, barometric pressure, pollution, automobile exhaust, soot density, airborne particle density, airborne particle size, airborne particle shape, airborne particle identity, volatile organic chemicals (VOCs), hydrocarbons, polycyclic aromatic hydrocarbons (PAHs), carcinogens, toxins, electromagnetic energy (optical radiation, X-rays, gamma rays, microwave radiation, terahertz radiation, ultraviolet radiation, infrared radiation, radio waves, and the like), EMF energy, atomic energy (alpha particles, beta-particles, gamma rays, and the like), gravity, light properties (such as intensity, frequency, flicker, and phase), ozone, carbon monoxide, greenhouse gases, CO2, nitrous oxide, sulfides, airborne pollution, foreign material in the air, biological particles (viruses, bacteria, and toxins), signatures from chemical weapons, wind, air turbulence, sound and acoustical energy (both human audible and inaudible), ambient noise, ultrasonic energy, noise pollution, human voices, animal sounds, diseases expelled from others, the exhaled breath and breath constituents of others, toxins from others, bacteria & viruses from others, pheromones from others, industrial and transportation sounds, allergens, animal hair, pollen, exhaust from engines, vapors & fumes, fuel, signatures for mineral deposits or oil deposits, snow, rain, thermal energy, hot surfaces, hot gases, solar energy, hail, ice, vibrations, traffic, the number of people in a vicinity of the user, the number of people encountered throughout the day, other earpiece module users in the vicinity of the earpiece module user, coughing and sneezing sounds from people in the vicinity of the user, loudness and pitch from those speaking in the vicinity of the user, and the like.

In some embodiments, a physiological sensor and/or an environmental sensor may be configured to identify a person, such as biometric identification of a person, to whom the device 1 is attached (or may be configured to identify other persons in the vicinity of the person wearing the device 1). In some embodiments, the device 1 can be used for biometric user identification or multimodal voice authentication or for voice identification such that multiple sensors (acoustic, heart signature, fingerprint, etc.) can provide a more robust or secure authentication or identification. Voice identification may be done among a group of known existing voice identities or profiles.

In some embodiments, a physiological sensor and/or an environmental sensor may be configured to monitor physical aging rate (relative to an actual age) of a person or subject. Aging rate can be assessed from an analysis of any of a number of parameters including, but not limited to cell density, heart signature, voice acoustics, lung function, a level of mobility, blood pressure, body composition, blood pressure, and other information that can be obtained from a user profile. The signal processor 4 may be configured to process information from a physiological sensor and/or an environmental sensor or other sensors to assess aging rate. Physiological sensors configured to assess aging rate may include pulse rate sensors, blood pressure sensors, activity sensors, and psychosocial stress sensors. Environmental sensors configured to assess aging rate may include UV sensors and pollution sensors. Device 1 can keep track of biometric data historically, for example strides from previous runs or walks.

In some embodiments, a physiological sensor and/or an environmental sensor may be configured to be regenerated through a physical and/or chemical change. For example, it is anticipated that the device 1, incorporating physiological and/or environmental sensors according to embodiments of the present invention, may be coupled to an apparatus that is configured to "recharge" or regenerate one or more environmental and/or physiological sensors via a physical process or a chemical process, etc. For example, a recharging module for recharging electric power to the device 1 may also user electrical energy to reverse a chemical or physical change in one of the sensors. One example of such a sensor would be a sensor that requires the absorption or desorption of water vapor for resetting to baseline operation. Another example is a sensor that is reset (recharged) through oxidation or reduction in order to change the surface properties for monitoring vapors, such as some metal oxide sensors.

The signal processor 4 provides a means of converting the digital or analog signals from the sensors into data that can be transmitted wirelessly by the transmitter 6A-C. The signal processor 4 may be composed of, for example, signal conditioners, amplifiers, filters, digital-to-analog and analog-to-digital converters, digital encoders, modulators, mixers, multiplexers, transistors, various switches, microprocessors, or the like. For personal communication, the signal processor 4 processes signals received by a wireless communication receiver into signals that can be heard or viewed by the user. The received signals may also contain protocol information for linking various telemetric modules together, and this protocol information can also be processed by the signal processor 4 or alternatively by a remote processor or server (not shown).

The signal processor 4 may utilize one or more compression/decompression algorithms (CODECs) used in digital media for processing data. The communication modules (6A-C) can be comprised of one or transmitters that can be a variety of compact electromagnetic transmitters. A standard compact antenna can be used in the standard Bluetooth® headset protocol, but any kind of electromagnetic antenna suitable for transmitting at human-safe electromagnetic frequencies may be utilized. The communication modules (6A-C) can also include a communication receiver that can also include an antenna. In some embodiments, the receiving antenna and the transmitting antenna are physically the same. The receiver/transmitter can be, for example, a non-line-of-sight (NLOS) optical scatter transmission system. These systems typically use short-wave (blue or UV) optical radiation or "solar blind" (deep-UV) radiation in order to promote optical scatter, but IR wavelengths can also be used.

Additionally, a sonic or ultrasonic transmitter can be used as the receiver/transmitter of the device 1, but preferably using sounds that are higher or lower than the human hearing range. A variety of sonic and ultrasonic receivers and transmitters are available in the marketplace and may be utilized in accordance with embodiments. If a telecommunication device receiving wireless data signals from the device 1 is in close proximity to the device 1, and the wearable module is an earpiece module, a variety of transmission schemes can be used. For communicating audible conversational information directly to the earpiece user, encoded telemetric conversational data received by the receiver can be decoded by the signal processing module 4 to generate an electrical signal that can be converted into audible sound.

In some embodiments, the transmitter/receiver (6A-C) is configured to transmit signals from the signal processor 4 to a remote terminal following a predetermined time interval. For example, the transmitter may delay transmission until a certain amount of detection time has elapsed, until a certain amount of processing time has elapsed, etc. In some cases, the transmitter/receiver is configured to transmit signals to the remote terminal dependent on information sensed by the sensors (5A). For example, if an unstable pulse rate is sensed, a warning message may be sent to a remote terminal to communicate a need for help at a particular location as determined by a GPS device operatively coupled to the device 1.

The power source can be any portable power source 2 capable of fitting inside the housing 23. According to some embodiments, the power source 2 is a portable rechargeable lithium-polymer or zinc-air battery. Additionally, portable energy-harvesting power sources can be integrated into the in-ear device 20 and can serve as a primary or secondary power source. For example, a solar cell module (as will be further detailed) can be integrated into the device 1 for collecting and storing solar energy. Additionally, piezoelectric devices or microelectromechanical systems (MEMS) can be used to collect and store energy from body movements, electromagnetic energy, and other forms of energy in the environment or from the user himself. A thermoelectric or thermovoltaic device can be used to supply some degree of power from thermal energy or temperature gradients. In some embodiments, a cranking or winding mechanism can be used to store mechanical energy for electrical conversion or to convert mechanical energy into electrical energy that can be used immediately or stored for later. Biocompatible battery chemistry can be used within the balloon for biological applications and other battery chemistries can be used when non-biological applications are considered.

The communication module may be used for, but not limited to: processing or generating an audible sound from information received via the receiver (from a cell phone, computer, network, database, or the like) and/or processing or generating an electrical signal from an audible sound from the user such that the electrical signal can be transmitted telemetrically via the transmitter. For example, in standard Bluetooth® protocol, communication electronics are used to convert an audible conversation into an electrical signal for telemetric conversation; communication electronics are also used to convert a digitized telemetric conversation into an audible conversation for the earpiece user. Additionally, the communication module can be used to store, process, or play analog or digital information from music, radio shows, videos, or other audible entertainment and to communicate this information to an earpiece user. In many cases, this information includes information received by the receiver. In many cases, the analog or digital information is not stored in the communication module but, rather, is stored in a portable telecommunication device such as a cell phone. In such case, the communication module is used for converting the analog or digital information into audible sound for the earpiece user. The communication module may contain at least one microphone, speaker, signal processor, and digital memory. In some embodiments, the communication module may apply at least one CODEC for encoding or decoding information. The communication module may utilize non-audible forms of communication with the user, such as visual, physical, or mental (i.e., brainwaves or neural stimulation) communication with the user.

In some embodiments, an audible communicator is provided that is configured to communicate therapeutic sounds (e.g., music therapy, etc.) to a person in response to physiological or psychosocial stress. The audible communicator may be embodied in the communication module or may be a separate speaker. In some embodiments, light therapy may be provided to a person in response to physiological or psychosocial stress. In some embodiments, the communication module may be configured to communicate a treatment, therapy, and/or plan of action to the person upon detection of physiological and/or environmental concerns. For example, if it is detected that the person is being exposed to unhealthy doses of UV radiation, the communication module may audibly instruct the person to move away from the person's current location (e.g., move indoors, etc.). Mechanical vibrational therapy and electrical stimulation therapy are also examples of automated therapies that may be invoked by programs inside the device 1 in response to sensor readings from health and/or environmental sensors.

A health and environmental monitoring system according to embodiments that may incorporate device 1. The terms "wearable", "wearable monitoring device" and "sensor module" are used interchangeably herein in accordance with various embodiments. The health and environmental monitoring system is composed of at least one sensor module at least one portable telecommunication module that can be part of the in-ear device or be part of a communications device operatively coupled to the device such as a cell phone, at least one transmission system such as a Bluetooth module, at least one user interface, at least one personal database, and at least one anonymous database.

In at least one embodiment, data is transmitted from device 1 to a remote communication system 6D, that can save or received data from a remote server 7E.

In some embodiments, a system or device 1, can be part of an integrated miniaturized earpiece (or other body worn or embedded device) that includes all or a portion of the components shown. In other embodiments, a first portion of the components shown comprise part of a system working with an earpiece having a remaining portion that operates cooperatively with the first portion. In some embodiments, an fully integrated system or device 1 can include an earpiece having a power source 2 (such as button cell battery, a rechargeable battery, or other power source) and one or more processors 4 that can process a number of acoustic channels, provide for hearing loss correction and prevention, process sensor data, convert signals to and from digital and analog and perform appropriate filtering. In some embodiments, the processor 4 is formed from one or more digital signal processors (DSPs). The device can include one or more sensors 5 operationally coupled to the processor 4. Data from the sensors can be sent to the processor directly or wirelessly using appropriate wireless modules 6A and communication protocols such as Bluetooth, WiFi, NFC, RF, and Optical such as infrared for example. The sensors can constitute biometric, physiological, environmental, acoustical, or neurological among other classes of sensors. In some embodiments, the sensors can be embedded or formed on or within an expandable element or balloon that is used to occlude the ear canal. Such sensors can include noninvasive contactless sensors that have electrodes for EEGs, ECGs, transdermal sensors, temperature sensors, transducers, microphones, optical sensors, motion sensors or other biometric, neurological, or physiological sensors that can monitor brainwaves, heartbeats, breathing rates, vascular signatures, pulse oximetry, blood flow, skin resistance, glucose levels, and temperature among many other parameters. The sensor(s) can also be environmental including, but not limited to, ambient microphones, temperature sensors, humidity sensors, barometric pressure sensors, radiation sensors, volatile chemical sensors, particle detection sensors, or other chemical sensors. The sensors 5 can be directly coupled to the processor 4 or wirelessly coupled via a wireless communication system 6A. Also note that many of the components shown can be wirelessly coupled to each other and not necessarily limited to the wireless connections shown.

Even if the device 1 is primarily driven by acoustical means (e.g., an earpiece using an ambient microphone or an ear canal microphone for example), the device 1 can be a multimodal device that can be controlled by not only voice using a speech or voice recognition engine 3A (which can be local or remote), but by other user inputs such as gesture control 3B, or other user interfaces 3C can be used (e.g., external device keypad, camera, etc.). Similarly, the outputs can primarily be acoustic, but other outputs can be provided. The gesture control 3B, for example, can be a motion detector for detecting certain user movements (finger, head, foot, jaw, etc.) or a capacitive or touch screen sensor for detecting predetermined user patterns detected on or in close proximity to the sensor. The user interface 3C can be a camera on a phone or a pair of virtual reality (VR) or augmented reality (AR) "glasses" or other pair of glasses for detecting a wink or blink of one or both eyes. The user interface 3C can also include external input devices such as touch screens or keypads on mobile devices operatively coupled to the device 1. The gesture control can be local to the earpiece or remote (such as on a phone). As an earpiece, the output can be part of a user interface 8 that will vary greatly based on the application 9B (which will be described in further detail below). The user interface 8 can be primary acoustic providing for a text to speech output, or an auditory display, or some form of sonification that provides some form of non-speech audio to convey information or perceptualize data. Of course, other parts of the user interface 8 can be visual or tactile using a screen, LEDs and/or haptic device as examples.

In one embodiment, the User Interface 8 can use what is known as "sonification" to enable wayfinding to provide users an auditory means of direction finding. For example, and analogous to a Geiger counter, the user interface 8 can provide a series of beeps or clicks or other sound that increase in frequency as a user follows a correct path towards a predetermined destination. Straying away from the path will provide beeps, clicks or other sounds that will then slow down in frequency. In one example, the wayfinding function can provide an alert and steer a user left and right with appropriate beeps or other sonification. The sounds can vary in intensity, volume, frequency, and direction to assist a user with wayfinding to a particular destination. Differences or variations using one or two ears can also be exploited.

Head-related transfer function (HRTF) cues can be provided. A HRTF is a response that characterizes how an ear receives a sound from a point in space; a pair of HRTFs for two ears can be used to synthesize a binaural sound that seems to come from a particular point in space. Humans have just two ears, but can locate sounds in three dimensions in terms of range (distance), in terms of direction above and below, in front and to the rear, as well as to either side. This is possible because the brain, inner ear and the external ears (pinna) work together to make inferences about location. This ability to localize sound sources may have developed in humans and ancestors as an evolutionary necessity, since the eyes can only see a fraction of the world around a viewer, and vision is hampered in darkness, while the ability to localize a sound source works in all directions, to varying accuracy, regardless of the surrounding light. Some consumer home entertainment products designed to reproduce surround sound from stereo (two-speaker) headphones use HRTFs and similarly, such directional simulation can be used with earpieces to provide a wayfinding function.

In some embodiments, the processor 4 is coupled (either directly or wirelessly via module 6B) to memory 7A which can be local to the device 1 or remote to the device (but part of the system). The memory 7A can store acoustic information, raw or processed sensor data, or other information as desired. The memory 7A can receive the data directly from the processor 4 or via wireless communications 6B. In some embodiments, the data or acoustic information is recorded (7B) in a circular buffer or other storage device for later retrieval. In some embodiments, the acoustic information or other data is stored at a local or a remote database 7C. In some embodiments, the acoustic information or other data is analyzed by an analysis module 7D (either with or without recording 7B) and done either locally or remotely. The output of the analysis module can be stored at the database 7C or provided as an output to the user or other interested part (e.g., user's physician, a third party payment processor. Note that storage of information can vary greatly based on the particular type of information obtained. In the case of acoustic information, such information can be stored in a circular buffer, while biometric and other data may be stored in a different form of memory (either local or remote). In some embodiments, captured or harvested data can be sent to remote storage such as storage in "the cloud" when battery and other conditions are optimum (such as during sleep).

In some embodiments, the device 1 can be used in various commercial scenarios. One or more of the sensors used in the monitoring device can be used to create a unique or highly non-duplicative signature sufficient for authentication, verification or identification. Some human biometric signatures can be quite unique and be used by themselves or in conjunction with other techniques to corroborate certain information. For example, a heart beat or heart signature can be used for biometric verification. An individual's heart signature under certain contexts (under certain stimuli as when listening to a certain tone while standing or sitting) may have certain characteristics that are considered sufficiently unique. The heart signature can also be used in conjunction with other verification schemes such as pin numbers, predetermined gestures, fingerprints, or voice recognition to provide a more robust, verifiable and secure system. In some embodiments, biometric information can be used to readily distinguish one or more speakers from a group of known speakers such as in a teleconference call or a videoconference call.

In some embodiments, the device 1 can be part of a payment system 9A that works in conjunction with the one or more sensors 5. In some embodiments, the payment system 9A can operate cooperatively with a wireless communication system 6B such as a 1-3 meter Near Field Communication (NFC) system, Bluetooth wireless system, WiFi system, or cellular system. In one embodiment, a very short range wireless system uses an NFC signal to confirm possession of the device in conjunction with other sensor information that can provide corroboration of identification, authorization, or authentication of the user for a transaction. In some embodiments, the system will not fully operate using an NFC system due to distance limitations and therefore another wireless communication protocol can be used.

In one embodiment, the sensor S can include a Snapdragon Sense ID 3D fingerprint technology by Qualcomm or other designed to boost personal security, usability and integration over touch-based fingerprint technologies. The new authentication platform can utilize Qualcomm's Secure MSM technology and the FIDO (Fast Identity Online) Alliance Universal Authentication Framework (UAF) specification to remove the need for passwords or to remember multiple account usernames and passwords. As a result, in the future, users will be able to login to any website which supports FIDO through using their device and a partnering browser plug-in which can be stored in memory 7A or elsewhere. solution) The Qualcomm fingerprint scanner technology is able to penetrate different levels of skin, detecting 3D details including ridges and sweat pores, which is an element touch-based biometrics do not possess. Of course, in a multimodal embodiment, other sensor data can be used to corroborate identification, authorization or authentication and gesture control can further be used to provide a level of identification, authorization or authentication. Of course, in many instances, 3D fingerprint technology may be burdensome and considered "over-engineering" where a simple acoustic or biometric point of entry is adequate and more than sufficient. For example, after an initial login, subsequent logins can merely use voice recognition as a means of accessing a device. If further security and verification is desired for a commercial transaction for example, then other sensors as the 3D fingerprint technology can be used.

In some embodiments, an external portion of the device (e.g., an end cap) can include a fingerprint sensor and/or gesture control sensor to detect a fingerprint and/or gesture. Other sensors and analysis can correlate other parameters to confirm that user fits a predetermined or historical profile within a predetermined threshold. For example, a resting heart rate can typically be within a given range for a given amount of detected motion. In another example, a predetermined brainwave pattern in reaction to a predetermined stimulus (e.g., music, sound pattern, visual presentation, tactile stimulation, etc.) can also be found be within a given range for a particular person. In yet another example, sound pressure levels (SPL) of a user's voice and/or of an ambient sound can be measured in particular contexts (e.g., in a particular store or at a particular venue as determined by GPS or a beacon signal) to verify and corroborate additional information alleged by the user. For example, a person conducting a transaction at a known venue having a particular background noise characteristic (e.g., periodic tones or announcements or Music playing in the background at known SPL levels measured from a point of sale) commonly frequented by the user of the monitoring device can provide added confirmation that a particular transaction is occurring in a location by the user. In another context, if a registered user at home (with minimal background noise) is conducting a transaction and speaking with a customer service representative regarding the transaction, the user may typically speak at a particular volume or SPL indicative that the registered user is the actual person claiming to make the transaction. A multimodal profile can be built and stored for an individual to sufficiently corroborate or correlate the information to that individual. Presumably, the correlation and accuracy becomes stronger over time as more sensor data is obtained as the user utilizes the device 1 and a historical profile is essentially built. Thus, a very robust payment system 9A can be implemented that can allow for mobile commerce with the use of the earpiece alone or in conjunction with a mobile device such as a cellular phone. Of course, information can be stored or retained remotely in server or database and work cooperatively with the device 1. In other applications, the pay system can operate with almost any type of commerce.

Additionally, the device 1 can include local or remote memory, local or remote databases, and features for recording can all be represented by the storage device 7 which can be coupled to an analysis module 7D. As before, the device 1 can be powered by a power source 2. The device 1 can include one or more processors 4 that can process a number of acoustic channels and process such channels for situational awareness and/or for keyword or sound pattern recognition, as well as daily speech the user speaks, coughs, sneezes, etc. The processor(s) 4 can provide for hearing loss correction and prevention, process sensor data, convert signals to and from digital and analog and perform appropriate filtering as needed. In some embodiments, the processor 4 is formed from one or more digital signal processors (DSPs). The device can include one or more sensors 5 operationally coupled to the processor 4. The sensors can be biometric and/or environmental. Such environmental sensors can sense one or more among light, radioactivity, electromagnetism, chemicals, odors, or particles. The sensors can also detect physiological changes or metabolic changes. In some embodiments, the sensors can include electrodes or contactless sensors and provide for neurological readings including brainwaves. The sensors can also include transducers or microphones for sensing acoustic information. Other sensors can detect motion and can include one or more of a GPS device, an accelerometer, a gyroscope, a beacon sensor, or NFC device. One or more sensors can be used to sense emotional aspects such as stress or other affective attributes. In a multimodal, multisensory embodiment, a combination of sensors can be used to make emotional or mental state assessments or other anticipatory determinations.

User interfaces can be used alone or in combination with the aforementioned sensors to also more accurately make emotional or mental state assessments or other anticipatory determinations. A voice control module 3A can include one or more of an ambient microphone, an ear canal microphone or other external microphones (e.g., from a phone, lap top, or other external source) to control the functionality of the device 1 to provide a myriad of control functions such as retrieving search results (e.g., for information, directions) or to conduct transactions (e.g., ordering, confirming an order, making a purchase, canceling a purchase, etc.), or to activate other functions either locally or remotely (e.g., turn on a light, open a garage door). The use of an expandable element or balloon for sealing an ear canal can be strategically used in conjunction with an ear canal microphone (in the sealed ear canal volume) to isolate a user's voice attributable to bone conduction and correlate such voice from bone conduction with the user's voice picked up by an ambient microphone. Through appropriate mixing of the signal from the ear canal microphone and the ambient microphone, such mixing technique can provide for a more intelligible voice substantially free of ambient noise that is more recognizable by voice recognition engines such as SIRI by Apple, Google Now by Google, or Cortana by Microsoft.

The voice control interface 3A can be used alone or optionally with other interfaces that provide for gesture control 3B. Alternatively, the gesture control interface(s) 3B can be used by themselves. The gesture control interface(s) 3B can be local or remote and can be embodied in many different forms or technologies. For example, a gesture control interface can use radio frequency, acoustic, optical, capacitive, or ultrasonic sensing. The gesture control interface can also be switch-based using a foot switch or toe switch. An optical or camera sensor or other sensor can also allow for control based on winks, blinks, eye movement tracking, mandibular movement, swallowing, or a suck-blow reflex as examples.

The processor 4 can also interface with various devices or control mechanisms within the ecosystem of the device 1. For example, the device can include various valves that control the flow of fluids or acoustic sound waves. More specifically, in one example the device 1 can include a shutter or "aural iris" in the form of an electro active polymer that controls a level or an opening size that controls the amount of acoustic sound that passes through to the user's ear canal. In another example, the processor 4 can control a level of battery charging to optimize charging time or optimize battery life in consideration of other factors such as temperature or safety in view of the rechargeable battery technology used.

A brain control interface (BCI) 5B can be incorporated in the embodiments to allow for control of local or remote functions including, but not limited to prosthetic devices. In some embodiments, electrodes or contactless sensors in the balloon of an earpiece can pickup brainwaves or perform an EEG reading that can be used to control the functionality of the earpiece itself or the functionality of external devices. The BCI 5B can operate cooperatively with other user interfaces (8A or 3C) to provide a user with adequate control and feedback. In some embodiments, the earpiece and electrodes or contactless sensors can be used in Evoked Potential Tests. Evoked potential tests measure the brain's response to stimuli that are delivered through sight, hearing, or touch. These sensory stimuli evoke minute electrical potentials that travel along nerves to the brain, and can be recorded typically with patch-like sensors (electrodes) that are attached to the scalp and skin over various peripheral sensory nerves, but in these embodiments, the contactless sensors in the earpiece can be used instead. The signals obtained by the contactless sensors are transmitted to a computer, where they are typically amplified, averaged, and displayed. There are 3 major types of evoked potential tests including: 1) Visual evoked potentials, which are produced by exposing the eye to a reversible checkerboard pattern or strobe light flash, help to detect vision impairment caused by optic nerve damage, particularly from multiple sclerosis; 2) Brainstem auditory evoked potentials, generated by delivering clicks to the ear, which are used to identify the source of hearing loss and help to differentiate between damage to the acoustic nerve and damage to auditory pathways within the brainstem; and 3) Somatosensory evoked potentials, produced by electrically stimulating a peripheral sensory nerve or a nerve responsible for sensation in an area of the body which can be used to diagnose peripheral nerve damage and locate brain and spinal cord lesions The purpose of the Evoked Potential Tests include assessing the function of the nervous system, aiding in the diagnosis of nervous system lesions and abnormalities, monitoring the progression or treatment of degenerative nerve diseases such as multiple sclerosis, monitoring brain activity and nerve signals during brain or spine surgery, or in patients who are under general anesthesia, and assessing brain function in a patient who is in a coma. In some embodiments, particular brainwave measurements (whether resulting from Evoked Potential stimuli or not) can be correlated to particular thoughts and selections to train a user to eventually consciously make selections merely by using brainwaves. For example, if a user is given a selection among A. Apple B. Banana and C. Cherry, a correlation of brainwave patterns and a particular selection can be developed or profiled and then subsequently used in the future to determine and match when a particular user merely thinks of a particular selection such as "C. Cherry". The more distinctively a particular pattern correlates to a particular selection, the more reliable the use of this technique as a user input.

User interface 8A can include one or more among an acoustic output or an "auditory display", a visual display, a sonification output, or a tactile output (thermal, haptic, liquid leak, electric shock, air puff, etc.). In some embodiments, the user interface 8A can use an electroactive polymer (EAP) to provide feedback to a user. As noted above, a BCI 5B can provide information to a user interface 8A in a number of forms. In some embodiments, balloon pressure oscillations or other adjustments can also be used as a means of providing feedback to a user. Also note that mandibular movements (chewing, swallowing, yawning, etc.) can alter balloon pressure levels (of a balloon in an ear canal) and be used as way to control functions. (Also note that balloon pressure can be monitored to correlate with mandibular movements and thus be used as a sensor for monitoring such actions as chewing swallowing and yawning).

Other user interfaces 3C can provide external device inputs that can be processed by the processor(s) 4. As noted above, these inputs include, but are not limited to, external device keypads, keyboards, cameras, touch screens, mice, and microphones to name a few.

The user interfaces, types of control, and/or sensors may likely depend on the type of application 9B. In a mobile application, a mobile phone microphone(s), keypad, touchscreen, camera, or GPS or motion sensor can be utilized to provide a number of the contemplated functions. In a vehicular environment, a number of the functions can be coordinated with a car dash and stereo system and data available from a vehicle. In an exercise, medical, or health context, a number of sensors can monitor one or more among, heart beat, blood flow, blood oxygenation, pulse oximetry, temperature, glucose, sweat, electrolytes, lactate, pH, brainwave, EEG, ECG or other physiological, or biometric data. Biometric data can also be used to confirm a patient's identity in a hospital or other medical facility to reduce or avoid medical record errors and mix-ups. In a social networking environment, users in a social network can detect each other's presence, interests, and vital statistics to spur on athletic competition, commerce or other social goals or motivations. In a military or professional context, various sensors and controls disclosed herein can offer a discrete and nearly invisible or imperceptible way of monitoring and communicating that can extend the "eyes and ears" of an organization to each individual using an earpiece as described above. In a commercial context, a short-range communication technology such as NFC or beacons can be used with other biometric or gesture information to provide for a more robust and secure commercial transactional system. In a call center context or other professional context, the earpiece could incorporate a biosensor that measures emotional excitement by measuring physiological responses. The physiological responses can include skin conductance or Galvanic Skin Response, temperature and motion.

In yet other aspects, some embodiments can monitor a person's sleep quality, mood, or assess and provide a more robust anticipatory device using a semantics acoustic engine with other sensors. The semantic engine can be part of the processor 4 or part of the analysis module 7D that can be performed locally at the device 1 or remotely as part of an overall system. If done remotely at a remote server, the system 1 can include a server (or cloud) that includes algorithms for analysis of gathered sensor data and profile information for a particular user. In contrast to other schemes, the embodiments herein can perform semantic analysis based on all biometrics, audio, and metadata (speaker ID, etc.) in combination and also in a much "cleaner" environments within a sealed EAC sealed by a proprietary balloon that is immune to many of the detriments in other schemes used to attempt to seal an EAC. Depending on the resources available at a particular time such as processing power, semantic analysis applications, or battery life, the semantic analysis would be best performed locally within a monitoring earpiece device itself, or within a cellular phone operationally coupled to the earpiece, or within a remote server or cloud or a combination thereof.

Though the methods herein may apply broadly to a variety of form factors for a monitoring apparatus (device 1), in some embodiments herein a 2-way communication device in the form of an earpiece with at least a portion being housed in an ear canal can function as a physiological monitor, an environmental monitor, and a wireless personal communicator. Because the ear region is located next to a variety of "hot spots" for physiological an environmental sensing—including the carotid artery, the paranasal sinus, etc.—in some cases an earpiece monitor takes preference over other form factors. Furthermore, the earpiece can use the ear canal microphone to obtain heart rate, heart rate signature, blood pressure and other biometric information such as acoustic signatures from chewing or swallowing or from breathing or breathing patterns. The earpiece can take advantage of commercially available open-architecture, ad hoc, wireless paradigms, such as Bluetooth®, Wi-Fi, or ZigBee. In some embodiments, a small, compact earpiece contains at least one microphone and one speaker, and is configured to transmit information wirelessly to a recording device such as, for example, a cell phone, a personal digital assistant (PDA), and/or a computer. In another embodiment, the earpiece contains a plurality of sensors for monitoring personal health and environmental exposure. Health and environmental information, sensed by the sensors is transmitted wirelessly, in real-time, to a recording device or media, capable of processing and organizing the data into meaningful displays, such as charts. In some embodiments, an earpiece user can monitor health and environmental exposure data in real-time, and may also access records of collected data throughout the day, week, month, etc., by observing charts and data through an audio-visual display. Note that the embodiments are not limited to an earpiece and can include other body worn or insertable or implantable devices as well as devices that can be used outside of a biological context (e.g., an oil pipeline, gas pipeline, conduits used in vehicles, or water or other chemical plumbing or conduits). Other body worn devices contemplated herein can incorporate such sensors and include, but are not limited to, glasses, jewelry, watches, rings, anklets, bracelets, contact lenses, headphones, earphones, earbuds, canal phones, hats, caps, shoes, mouthpieces, or nose plugs to name a few. In addition, all types of body insertable devices are contemplated as well.

Figure 6:
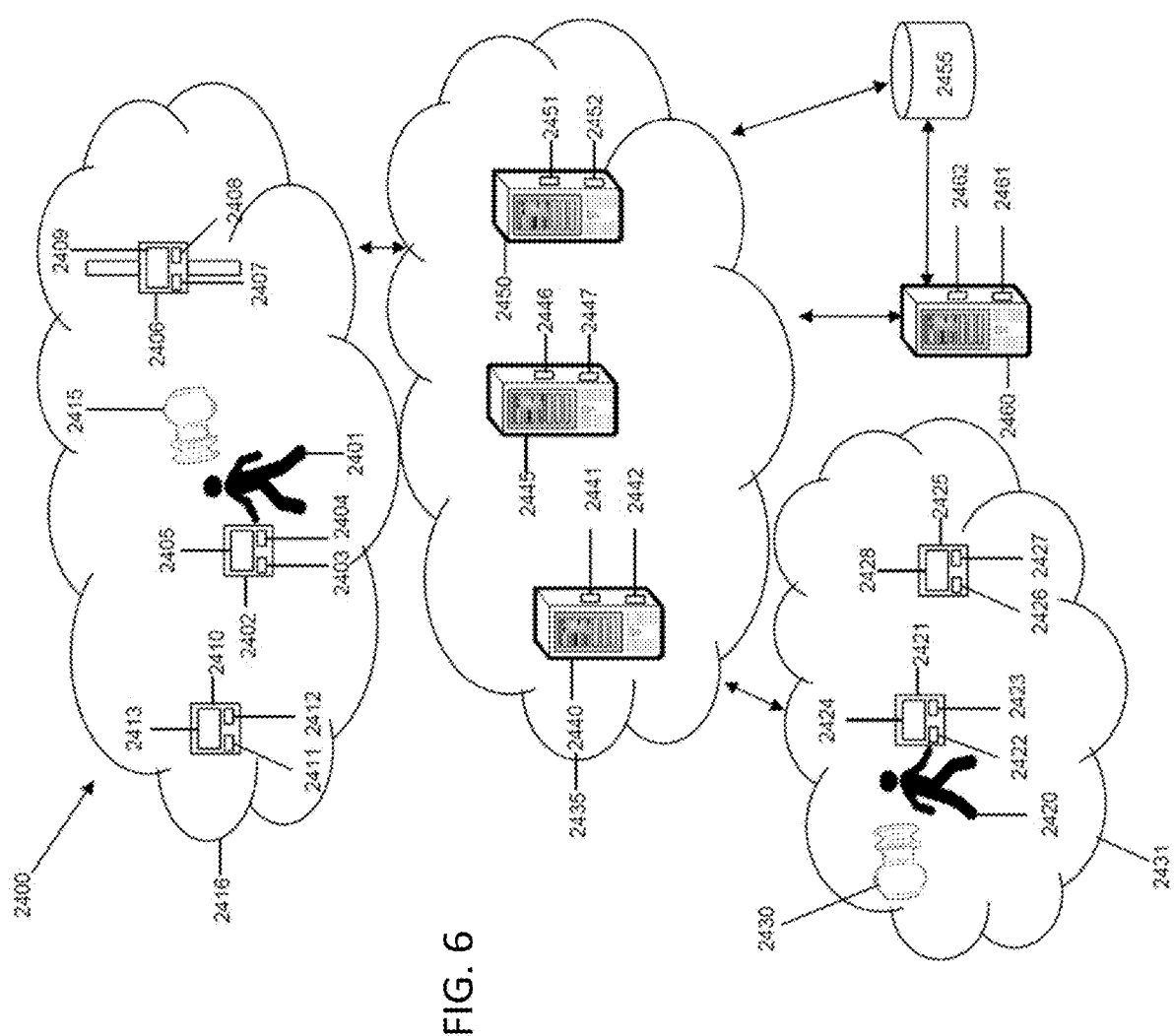
FIG. 6 is a schematic diagram of a system for utilizing devices according to an embodiment of the present disclosure.

As shown in FIG. 6, a system 2400 and methods for utilizing device(s) 1 in general. Although an example may refer to an earphone device (e.g., 2415) the systems and methods are applicable to any device 1 (e.g., ring, watch, phone).

The system 2400 may be configured to support, but is not limited to supporting, data and content services, audio processing applications and services, audio output and/or input applications and services, applications and services for transmitting and receiving audio content, authentication applications and services, computing applications and services, cloud computing services, internet services, satellite services, telephone services, software as a service (SaaS) applications, platform-as-a-service (PaaS) applications, gaming applications and services, social media applications and services, productivity applications and services, voice-over-internet protocol (VoIP) applications and services, speech-to-text translation applications and services, interactive voice applications and services, mobile applications and services, and any other computing applications and services. The system may include a first user 2401, who may utilize a first user device 2402 to access data, content, and applications, or to perform a variety of other tasks and functions. As an example, the first user 2401 may utilize first user device 2402 to access an application (e.g. a browser or a mobile application) executing on the first user device 2402 that may be utilized to access web pages, data, and content associated with the system 2400. In certain embodiments, the first user 2401 may be any type of user that may potentially desire to listen to audio content, such as from, but not limited to, a music playlist accessible via the first user device 2402, a telephone call that the first user 2401 is participating in, audio content occurring in an environment in proximity to the first user 2401, any other type of audio content, or a combination thereof. For example, the first user 2401 may be an individual that may be participating in a telephone call with another user, such as second user 2420.

The first user device 2402 utilized by the first user 2401 may include a memory 2403 that includes instructions, and a processor 2404 that executes the instructions from the memory 2403 to perform the various operations that are performed by the first user device 2402. In certain embodiments, the processor 2404 may be hardware, software, or a combination thereof. The first user device 2402 may also include an interface 2405 (e.g. screen, monitor, graphical user interface, etc.) that may enable the first user 2401 to interact with various applications executing on the first user device 2402, to interact with various applications executing within the system 2400, and to interact with the system 2400 itself. In certain embodiments, the first user device 2402 may include any number of transducers, such as, but not limited to, microphones, speakers, any type of audio-based transducer, any type of transducer, or a combination thereof. In certain embodiments, the first user device 2402 may be a computer, a laptop, a tablet device, a phablet, a server, a mobile device, a smartphone, a smart watch, and/or any other type of computing device. Illustratively, the first user device 2402 is shown as a mobile device in FIG. 6. The first user device 2402 may also include a global positioning system (GPS), which may include a GPS receiver and any other necessary components for enabling GPS functionality, accelerometers, gyroscopes, sensors, and any other componentry suitable for a mobile device.

In addition to using first user device 2402, the first user 2401 may also utilize and/or have access to a second user device 2406 and a third user device 2410. As with first user device 2402, the first user 2401 may utilize the second and third user devices 2406, 2410 to transmit signals to access various online services and content. The second user device 2406 may include a memory 2407 that includes instructions, and a processor 2408 that executes the instructions from the memory 2407 to perform the various operations that are performed by the second user device 2406. In certain embodiments, the processor 2408 may be hardware, software, or a combination thereof. The second user device 2406 may also include an interface 2409 that may enable the first user 2401 to interact with various applications executing on the second user device 2406 and to interact with the system 2400. In certain embodiments, the second user device 2406 may include any number of transducers, such as, but not limited to, microphones, speakers, any type of audio-based transducer, any type of transducer, or a combination thereof. In certain embodiments, the second user device 2406 may be and/or may include a computer, any type of sensor, a laptop, a set-top-box, a tablet device, a phablet, a server, a mobile device, a smartphone, a smart watch, and/or any other type of computing device. Illustratively, the second user device 2402 is shown as a smart watch device in FIG. 6.

The third user device 2410 may include a memory 2411 that includes instructions, and a processor 2412 that executes the instructions from the memory 2411 to perform the various operations that are performed by the third user device 2410. In certain embodiments, the processor 2412 may be hardware, software, or a combination thereof. The third user device 2410 may also include an interface 2413 that may enable the first user 2401 to interact with various applications executing on the second user device 2406 and to interact with the system 2400. In certain embodiments, the third user device 2410 may include any number of transducers, such as, but not limited to, microphones, speakers, any type of audio-based transducer, any type of transducer, or a combination thereof. In certain embodiments, the third user device 2410 may be and/or may include a computer, any type of sensor, a laptop, a set-top-box, a tablet device, a phablet, a server, a mobile device, a smartphone, a smart watch, and/or any other type of computing device. Illustratively, the third user device 2410 is shown as a smart watch device in FIG. 6.

The first, second, and/or third user devices 2402, 2406, 2410 may belong to and/or form a communications network 2416. In certain embodiments, the communications network 2416 may be a local, mesh, or other network that facilitates communications among the first, second, and/or third user devices 2402, 2406, 2410 and/or any other devices, programs, and/or networks of system 2400 or outside system 2400. In certain embodiments, the communications network 2416 may be formed between the first, second, and third user devices 2402, 2406, 2410 through the use of any type of wireless or other protocol and/or technology. For example, the first, second, and third user devices 2402, 2406, 2410 may communicate with one another in the communications network 2416, such as by utilizing Bluetooth Low Energy (BLE), classic Bluetooth, ZigBee, cellular, NFC, Wi-Fi, Z-Wave, ANT+, IEEE 802.15.4, IEEE 802.22, ISA100a, infrared, ISM band, RFID, UWB, Wireless HD, Wireless USB, any other protocol and/or wireless technology, satellite, fiber, or any combination thereof. Notably, the communications network 2416 may be configured to communicatively link with and/or communicate with any other network of the system 2400 and/or outside the system 2400.

The system 2400 may also include an earphone device 2415, which the first user 2401 may utilize to hear and/or audition audio content, transmit audio content, receive audio content, experience any type of content, process audio content, adjust audio content, store audio content, perform any type of operation with respect to audio content, or a combination thereof. The earphone device 2415 may be an earpiece, a hearing aid, an ear monitor, an ear terminal, a behind-the-ear device, any type of acoustic device, or a combination thereof. The earphone device 2415 may include any type of component utilized for any type of earpiece. In certain embodiments, the earphone device 2415 may include any number of ambient sound microphones that may be configured to capture and/or measure ambient sounds and/or audio content occurring in an environment that the earphone device 2415 is present in and/or is proximate to. In certain embodiments, the ambient sound microphones may be placed at a location or locations on the earphone device 2415 that are conducive to capturing and measuring ambient sounds occurring in the environment. For example, the ambient sound microphones may be positioned in proximity to a distal end (e.g. the end of the earphone device 2415 that is not inserted into the first user's 2401 ear) of the earphone device 2415 such that the ambient sound microphones are in an optimal position to capture ambient or other sounds occurring in the environment. In certain embodiments, the earphone device 2415 may include any number of ear canal microphones, which may be configured to capture and/or measure sounds occurring in an ear canal of the first user 2401 or other user wearing the earphone device 2415. In certain embodiments, the ear canal microphones may be positioned in proximity to a proximal end (e.g. the end of the earphone device 2415 that is inserted into the first user's 2401 ear) of the earphone device 2415 such that sounds occurring in the ear canal of the first user 2401 may be captured more readily.

The earphone device 2415 may also include any number of transceivers, which may be configured transmit signals to and/or receive signals from any of the devices in the system 2400. In certain embodiments, a transceiver of the earphone device 2415 may facilitate wireless connections and/or transmissions between the earphone device 2415 and any device in the system 2400, such as, but not limited to, the first user device 2402, the second user device 2406, the third user device 2410, the fourth user device 2421, the fifth user device 2425, the earphone device 2430, the servers 2440, 2445, 2450, 2460, and the database 2455. The earphone device 2415 may also include any number of memories for storing content and/or instructions, processors that execute the instructions from the memories to perform the operations for the earphone device 2415, and/or any type integrated circuit for facilitating the operation of the earphone device 2415. In certain embodiments, the processors may comprise, hardware, software, or a combination of hardware and software. The earphone device 2415 may also include one or more ear canal receivers, which may be speakers for outputting sound into the ear canal of the first user 2401. The ear canal receivers may output sounds obtained via the ear canal microphones, ambient sound microphones, any of the devices in the system 2400, from a storage device of the earphone device 2415, or any combination thereof.

The ear canal receivers, ear canal microphones, transceivers, memories, processors, integrated circuits, and/or ear canal receivers may be affixed to an electronics package that includes a flexible electronics board. The earphone device 2415 may include an electronics packaging housing that may house the ambient sound microphones, ear canal microphones, ear canal receivers (i.e. speakers), electronics supporting the functionality of the microphones and/or receivers, transceivers for receiving and/or transmitting signals, power sources (e.g. batteries and the like), any circuitry facilitating the operation of the earphone device 2415, or any combination thereof. The electronics package including the flexible electronics board may be housed within the electronics packaging housing to form an electronics packaging unit. The earphone device 2415 may further include an earphone housing, which may include receptacles, openings, and/or keyed recesses for connecting the earphone housing to the electronics packaging housing and/or the electronics package. For example, nozzles of the electronics packaging housing may be inserted into one or more keyed recesses of the earphone housing so as to connect and secure the earphone housing to the electronics packaging housing. When the earphone housing is connected to the electronics packaging housing, the combination of the earphone housing and the electronics packaging housing may form the earphone device 2415. The earphone device 2415 may further include a cap for securing the electronics packaging housing, the earphone housing, and the electronics package together to form the earphone device 2415.

In certain embodiments, the earphone device 2415 may be configured to have any number of changeable tips, which may be utilized to facilitate the insertion of the earphone device 2415 into an ear aperture of an ear of the first user 2401, secure the earphone device 2415 within the ear canal of an ear of the first user 2401, and/or to isolate sound within the ear canal of the first user 2401. The tips may be foam tips, which may be affixed onto an end of the earphone housing of the earphone device 2415, such as onto a stent and/or attachment mechanism of the earphone housing. In certain embodiments, the tips may be any type of eartip as disclosed and described in the present disclosure. The eartips as disclosed in the present disclosure may be configured to facilitate distributed reduced contact force, sound isolation for sound in the ear canal of the first user 2401 (i.e. between the ambient environment and the ear canal environment within an ear of the first user 2401), mold into a variety of forms and/or positions, encapsulate volumes upon insertion into an ear aperture of the first user 2401, have a pressure adjusting design, facilitate notched stent retention (i.e. on a stent of the earphone housing), facilitate stent insertion into an ear canal of the first user 2401 via an ear aperture of the first user 2401, or any combination thereof. In certain embodiments, the eartip may be designed to provide sound isolation capability that is at least as effective as conventional foam and/or flange tips. Notably, the eartips may be manufactured and configured to be made in any desired size specifications and/or materials, and may be tailored to each individual user, such as first user 2401. In contrast to conventional foam or flange tips, an eartip according to the present disclosure may be adjusted for size without having to substitute the eartip with another eartip, may have an EPA NRR rating of NRR=18, may have a unique flatter high frequency attenuation profile so as to maintain audio quality, may have ease of manufacturability, and may be designed to distribute contact force and minimize radial force against a user's ear canal walls when positioned in a user's ear canal. Additionally, an eartip according to the present disclosure may be made of a non-porous material that is not closed cell foam or open cell foam.

In certain embodiments, the eartip may be designed so that the earphone device's 2415 retention force on the ear canal walls of the first user 2401 may be distributed over a larger area than traditional foam or flange tips allow, thereby reducing the pressure on the ear canal walls of the first user 2401. Unlike foam tips, which primarily provide a restoring radial force that exerts pressure against the ear canal walls of a user, the eartip is designed to move both radially and axially, which allows for more give and redistribution of contact over a larger area, and, thus, decreases the retention pressure. As a result, this allows for increased comfort for the user and allows the user to utilize the eartip for an extended period of time when compared to traditional foam and/or flange tips. In certain embodiments, the eartip utilized with the earphone device 2415 may be configured to encapsulate a volume of gas and/or liquid. In either case (i.e. gas or liquid), the bulk of sound isolation provided by the eartip is achieved through the reflection of ambient sound waves so that the encapsulated volume can be low mass. In certain embodiments, portions of the eartip may encapsulate a volume with the ability to release volume when pressed upon without having to incorporate complicated valves. The encapsulated volume may be achieved by the ear canal wall pressing radially and/or axially against the outer surfaces of the eartip, which may force the outer portion of the eartip to seal with the inner portion of the eartip. In certain embodiments, the inner portion of the eartip may be small than the outer diameter of the stent of the earphone housing upon which the eartip is placed so that upon insertion of the eartip on the stent, the inner portion stretches outward to meet the outer surface of the eartip, which further facilitates the sealing of the ear canal of the first user 2401.

In certain embodiments, the stent of the eartip, over which the eartip is placed, may be designed to have a smaller diameter front end and a larger diameter middle section to promote retention of the eartip on the stent itself. In certain embodiments, a portion of the eartip may have an inner core diameter that is smaller than the stent outer diameter so that the eartip provides radial compression upon the stent so as to enhance sealing and to add friction to prevent axial slippage within the ear canal of the first user 2401. In certain embodiments, an increased mid-section inner core diameter of the eartip may be utilized (i.e. larger than the smaller inner core diameter of the eartip), which may be configured to line up with the mid-section outer diameter of the stent of the earphone housing of the earphone device 2415. This may provide axial stability for the earphone device 2415, while simultaneously preventing axial slippage from the ear canal of the first user 2401. In certain embodiments, the eartip may have an insertion end that has a funnel shape, which aids in inserting the eartip onto the stent of the earphone housing of the earphone device 2415.

In certain embodiments, the eartip has a configuration that applies minimal force against the first user's 2401 ear canal.

Additionally, the eartip can seal the first user's 2401 ear canal by providing at least 15 dB of attenuation across frequency. To facilitate manufacturability, the eartip may be molded inverted, thereby allowing inexpensive mass production. Lips of the eartip may then be folded to contact ledges to for the eartip that may be utilized by the first user 2401. Sealing and comfort depend upon an accurate fit within the first user's 2401 ear canal, and, as a result, eartips according to the present disclosure may be manufactured in several single sizes, and, because of the unique design of the eartips, a single eartip may be adjusted to fit multiple sizes, which minimizes manufacturing costs, while allowing for more flexibility, versatility, and for a greater number of sizes for the eartip. Notably, any of the features of any of the eartips described in the present disclosure may be combined and/or interchanged with any other eartips described in the present disclosure. Furthermore, the shape, size, features and/or functionality of any of the components of the earphone device and/or hearbud housing device described in the present disclosure may be modified for each particular user for the shape and size of each user's ear aperture and/or ear canal, or a combination thereof.

In further embodiments, the eartip may be configured to have an open configuration prior to insertion onto a stent of the earphone housing and/or the earphone device 2415 itself. By having an open configuration, the eartip may be mass produced using conventional molding techniques and/or by utilizing 3D commercial printers. The open configuration of the eartip also facilitates molding, and can be 3D printed, where the open configuration allows for resin removal. For example, resin removal may be achieved by utilizing commercial 3D printers that allow the use of lower durometer materials, such as Stratasys machines and the like. In certain embodiments, since the eartip has an open configuration, which is then sealed, any additional pressure can force encapsulated gas out of the eartip relieving the feedback pressure so as to keep the comfort level for the first user 2401 relatively stable.

In addition to the first user 2401, the system 2400 may include a second user 2420, who may utilize a fourth user device 2421 to access data, content, and applications, or to perform a variety of other tasks and functions. Much like the first user 2401, the second user 2420 may be may be any type of user that may potentially desire to listen to audio content, such as from, but not limited to, a storage device of the fourth user device 2421, a telephone call that the second user 2420 is participating in, audio content occurring in an environment in proximity to the second user 2420, any other type of audio content, or a combination thereof. For example, the second user 2420 may be an individual that may be listening to songs stored in a playlist that resides on the fourth user device 2421. Also, much like the first user 2401, the second user 2420 may utilize fourth user device 2421 to access an application (e.g. a browser or a mobile application) executing on the fourth user device 2421 that may be utilized to access web pages, data, and content associated with the system 2400. The fourth user device 2421 may include a memory 2422 that includes instructions, and a processor 2423 that executes the instructions from the memory 2422 to perform the various operations that are performed by the fourth user device 2421. In certain embodiments, the processor 2423 may be hardware, software, or a combination thereof. The fourth user device 2421 may also include an interface 2424 (e.g., a screen, a monitor, a graphical user interface, etc.) that may enable the second user 2420 to interact with various applications executing on the fourth user device 2421, to interact with various applications executing in the system 2400, and to interact with the system 2400. In certain embodiments, the fourth user device 2421 may include any number of transducers, such as, but not limited to, microphones, speakers, any type of audio-based transducer, any type of transducer, or a combination thereof. In certain embodiments, the fourth user device 2421 may be a computer, a laptop, a tablet device, a phablet, a server, a mobile device, a smartphone, a smart watch, and/or any other type of computing device. Illustratively, the fourth user device 2421 may be a computing device in FIG. 6. The fourth user device 2421 may also include any of the componentry described for first user device 2402, the second user device 2406, and/or the third user device 2410. In certain embodiments, the fourth user device 2421 may also include a global positioning system (GPS), which may include a GPS receiver and any other necessary components for enabling GPS functionality, accelerometers, gyroscopes, sensors, and any other componentry suitable for a computing device.

In addition to using fourth user device 2421, the second user 2420 may also utilize and/or have access to a fifth user device 2425. As with fourth user device 2421, the second user 2420 may utilize the fourth and fifth user devices 2421, 2425 to transmit signals to access various online services and content. The fifth user device 2425 may include a memory 2426 that includes instructions, and a processor 2427 that executes the instructions from the memory 2426 to perform the various operations that are performed by the fifth user device 2425. In certain embodiments, the processor 2427 may be hardware, software, or a combination thereof. The fifth user device 2425 may also include an interface 2428 that may enable the second user 2420 to interact with various applications executing on the fifth user device 2425 and to interact with the system 2400. In certain embodiments, the fifth user device 2425 may include any number of transducers, such as, but not limited to, microphones, speakers, any type of audio-based transducer, any type of transducer, or a combination thereof. In certain embodiments, the fifth user device 2425 may be and/or may include a computer, any type of sensor, a laptop, a set-top-box, a tablet device, a phablet, a server, a mobile device, a smartphone, a smart watch, and/or any other type of computing device. Illustratively, the fifth user device 2425 is shown as a tablet device in FIG. 6.

The fourth and fifth user devices 2421, 2425 may belong to and/or form a communications network 2431. In certain embodiments, the communications network 2431 may be a local, mesh, or other network that facilitates communications between the fourth and fifth user devices 2421, 2425, and/or any other devices, programs, and/or networks of system 2400 or outside system 2400. In certain embodiments, the communications network 2431 may be formed between the fourth and fifth user devices 2421, 2425 through the use of any type of wireless or other protocol and/or technology. For example, the fourth and fifth user devices 2421, 2425 may communicate with one another in the communications network 2416, such as by utilizing BLE, classic Bluetooth, ZigBee, cellular, NFC, Wi-Fi, Z-Wave, ANT+, IEEE 802.15.4, IEEE 802.22, ISA100a, infrared, ISM band, RFID, UWB, Wireless HD, Wireless USB, any other protocol and/or wireless technology, satellite, fiber, or any combination thereof. Notably, the communications network 2431 may be configured to communicatively link with and/or communicate with any other network of the system 2400 and/or outside the system 2400.

Much like first user 2401, the second user 2420 may have his or her own earphone device 2430. The earphone device 2430 may be utilized by the second user 2420 to hear and/or audition audio content, transmit audio content, receive audio content, experience any type of content, process audio content, adjust audio content, store audio content, perform any type of operation with respect to audio content, or a combination thereof. The earphone device 2430 may be an earpiece, a hearing aid, an ear monitor, an ear terminal, a behind-the-ear device, any type of acoustic device, or a combination thereof. The earphone device 2430 may include any type of component utilized for any type of earpiece, and may include any of the features, functionality and/or components described and/or usable with earphone device 2415. For example, earphone device 2430 may include any number of transceivers, ear canal microphones, ambient sound microphones, processors, memories, housings, eartips, foam tips, flanges, any other component, or any combination thereof.

In certain embodiments, the first, second, third, fourth, and/or fifth user devices 2402, 2406, 2410, 2421, 2425 and/or earphone devices 2415, 2430 may have any number of software applications and/or application services stored and/or accessible thereon. For example, the first and second user devices 2402, 2411 may include applications for processing audio content, applications for playing, editing, transmitting, and/or receiving audio content, streaming media applications, speech-to-text translation applications, cloud-based applications, search engine applications, natural language processing applications, database applications, algorithmic applications, phone-based applications, product-ordering applications, business applications, e-commerce applications, media streaming applications, content-based applications, database applications, gaming applications, internet-based applications, browser applications, mobile applications, service-based applications, productivity applications, video applications, music applications, social media applications, presentation applications, any other type of applications, any types of application services, or a combination thereof. In certain embodiments, the software applications and services may include one or more graphical user interfaces so as to enable the first and second users 2401, 2420 to readily interact with the software applications. The software applications and services may also be utilized by the first and second users 2401, 2420 to interact with any device in the system 2400, any network in the system 2400 (e.g. communications networks 2416, 2431, 2435), or any combination thereof. For example, the software applications executing on the first, second, third, fourth, and/or fifth user devices 2402, 2406, 2410, 2421, 2425 and/or earphone devices 2415, 2430 may be applications for receiving data, applications for storing data, applications for auditioning, editing, storing and/or processing audio content, applications for receiving demographic and preference information, applications for transforming data, applications for executing mathematical algorithms, applications for generating and transmitting electronic messages, applications for generating and transmitting various types of content, any other type of applications, or a combination thereof. In certain embodiments, the first, second, third, fourth, and/or fifth user devices 2402, 2406, 2410, 2421, 2425 and/or earphone devices 2415, 2430 may include associated telephone numbers, internet protocol addresses, device identities, or any other identifiers to uniquely identify the first, second, third, fourth, and/or fifth user devices 2402, 2406, 2410, 2421, 2425 and/or earphone devices 2415, 2430 and/or the first and second users 2401, 2420. In certain embodiments, location information corresponding to the first, second, third, fourth, and/or fifth user devices 2402, 2406, 2410, 2421, 2425 and/or earphone devices 2415, 2430 may be obtained based on the internet protocol addresses, by receiving a signal from the first, second, third, fourth, and/or fifth user devices 2402, 2406, 2410, 2421, 2425 and/or earphone devices 2415, 2430 or based on profile information corresponding to the first, second, third, fourth, and/or fifth user devices 2402, 2406, 2410, 2421, 2425 and/or earphone devices 2415, 2430. The system 2400 may also include a communications network 2435. The communications network 2435 may be under the control of a service provider, the first and/or second users 2401, 2420, any other designated user, or a combination thereof. The communications network 2435 of the system 2400 may be configured to link each of the devices in the system 2400 to one another. For example, the communications network 2435 may be utilized by the first user device 2402 to connect with other devices within or outside communications network 2435. Additionally, the communications network 2435 may be configured to transmit, generate, and receive any information and data traversing the system 2400. In certain embodiments, the communications network 2435 may include any number of servers, databases, or other componentry. The communications network 2435 may also include and be connected to a mesh network, a local network, a cloud-computing network, an IMS network, a VoIP network, a security network, a VoLTE network, a wireless network, an Ethernet network, a satellite network, a broadband network, a cellular network, a private network, a cable network, the Internet, an internet protocol network, MPLS network, a content distribution network, any network, or any combination thereof. Illustratively, servers 2440, 2445, and 2450 are shown as being included within communications network 2435. In certain embodiments, the communications network 2435 may be part of a single autonomous system that is located in a particular geographic region, or be part of multiple autonomous systems that span several geographic regions.

Notably, the functionality of the system 2400 may be supported and executed by using any combination of the servers 2440, 2445, 2450, and 2460. The servers 2440, 2445, and 2450 may reside in communications network 2435, however, in certain embodiments, the servers 2440, 2445, 2450 may reside outside communications network 2435. The servers 2440, 2445, and 2450 may provide and serve as a server service that performs the various operations and functions provided by the system 2400. In certain embodiments, the server 2440 may include a memory 2441 that includes instructions, and a processor 2442 that executes the instructions from the memory 2441 to perform various operations that are performed by the server 2440. The processor 2442 may be hardware, software, or a combination thereof. Similarly, the server 2445 may include a memory 2446 that includes instructions, and a processor 2447 that executes the instructions from the memory 2446 to perform the various operations that are performed by the server 2445. Furthermore, the server 2450 may include a memory 2451 that includes instructions, and a processor 2452 that executes the instructions from the memory 2451 to perform the various operations that are performed by the server 2450. In certain embodiments, the servers 2440, 2445, 2450, and 2460 may be network servers, routers, gateways, switches, media distribution hubs, signal transfer points, service control points, service switching points, firewalls, routers, edge devices, nodes, computers, mobile devices, or any other suitable computing device, or any combination thereof. In certain embodiments, the servers 2440, 2445, 2450 may be communicatively linked to the communications network 2435, the communications network 2416, the communications network 2431, any network, any device in the system 2400, any program in the system 2400, or any combination thereof.

The database 2455 of the system 2400 may be utilized to store and relay information that traverses the system 2400, cache content that traverses the system 2400, store data about each of the devices in the system 2400 and perform any other typical functions of a database. In certain embodiments, the database 2455 may be connected to or reside within the communications network 2435, the communications network 2416, the communications network 2431, any other network, or a combination thereof. In certain embodiments, the database 2455 may serve as a central repository for any information associated with any of the devices and information associated with the system 2400. Furthermore, the database 2455 may include a processor and memory or be connected to a processor and memory to perform the various operation associated with the database 2455. In certain embodiments, the database 2455 may be connected to the earphone devices 2415, 2430, the servers 2440, 2445, 2450, 2460, the first user device 2402, the second user device 2406, the third user device 2410, the fourth user device 2421, the fifth user device 2425, any devices in the system 2400, any other device, any network, or any combination thereof.

The database 2455 may also store information and metadata obtained from the system 2400, store metadata and other information associated with the first and second users 2401, 2420, store user profiles associated with the first and second users 2401, 2420, store device profiles associated with any device in the system 2400, store communications traversing the system 2400, store user preferences, store information associated with any device or signal in the system 2400, store information relating to patterns of usage relating to the first, second, third, fourth, and fifth user devices 2402, 2406, 2410, 2421, 2425, store audio content associated with the first, second, third, fourth, and fifth user devices 2402, 2406, 2410, 2421, 2425 and/or earphone devices 2415, 2430, store audio content and/or information associated with the audio content that is captured by the ambient sound microphones, store audio content and/or information associated with audio content that is captured by ear canal microphones, store any information obtained from any of the networks in the system 2400, store audio content and/or information associated with audio content that is outputted by ear canal receivers of the system 2400, store any information and/or signals transmitted and/or received by transceivers of the system 2400, store any device and/or capability specifications relating to the earphone devices 2415, 2430, store historical data associated with the first and second users 2401, 2415, store information relating to the size (e.g. depth, height, width, curvatures, etc.) and/or shape of the first and/or second user's 2401, 2420 ear canals and/or ears, store information identifying and or describing any eartip utilized with the earphone devices 2401, 2415, store device characteristics for any of the devices in the system 2400, store information relating to any devices associated with the first and second users 2401, 2420, store any information associated with the earphone devices 2415, 2430, store log on sequences and/or authentication information for accessing any of the devices of the system 2400, store information associated with the communications networks 2416, 2431, store any information generated and/or processed by the system 2400, store any of the information disclosed for any of the operations and functions disclosed for the system 2400 herewith, store any information traversing the system 2400, or any combination thereof. Furthermore, the database 2455 may be configured to process queries sent to it by any device in the system 2400. The system 2400 may also include a software application, which may be configured to perform and support the operative functions of the system 2400, such as the operative functions of the first, second, third, fourth, and fifth user devices 2402, 2406, 2410, 2421, 2425 and/or the earphone devices 2415, 2430. In certain embodiments, the application may be a website, a mobile application, a software application, or a combination thereof, which may be made accessible to users utilizing one or more computing devices, such as the first, second, third, fourth, and fifth user devices 2402, 2406, 2410, 2421, 2425 and/or the earphone devices 2415, 2430. The application of the system 2400 may be accessible via an internet connection established with a browser program or other application executing on the first, second, third, fourth, and fifth user devices 2402, 2406, 2410, 2421, 2425 and/or the earphone devices 2415, 2430, a mobile application executing on the first, second, third, fourth, and fifth user devices 2402, 2406, 2410, 2421, 2425 and/or the earphone devices 2415, 2430, or through other suitable means. Additionally, the application may allow users and computing devices to create accounts with the application and sign-in to the created accounts with authenticating username and password log-in combinations. The application may include a custom graphical user interface that the first user 2401 or second user 2420 may interact with by utilizing a browser executing on the first, second, third, fourth, and fifth user devices 2402, 2406, 2410, 2421, 2425 and/or the earphone devices 2415, 2430. In certain embodiments, the software application may execute directly as an installed program on the first, second, third, fourth, and fifth user devices 2402, 2406, 2410, 2421, 2425 and/or the earphone devices 2415, 2430.

Computing System for Facilitating the Operation and Functionality of the System

Figure 7:
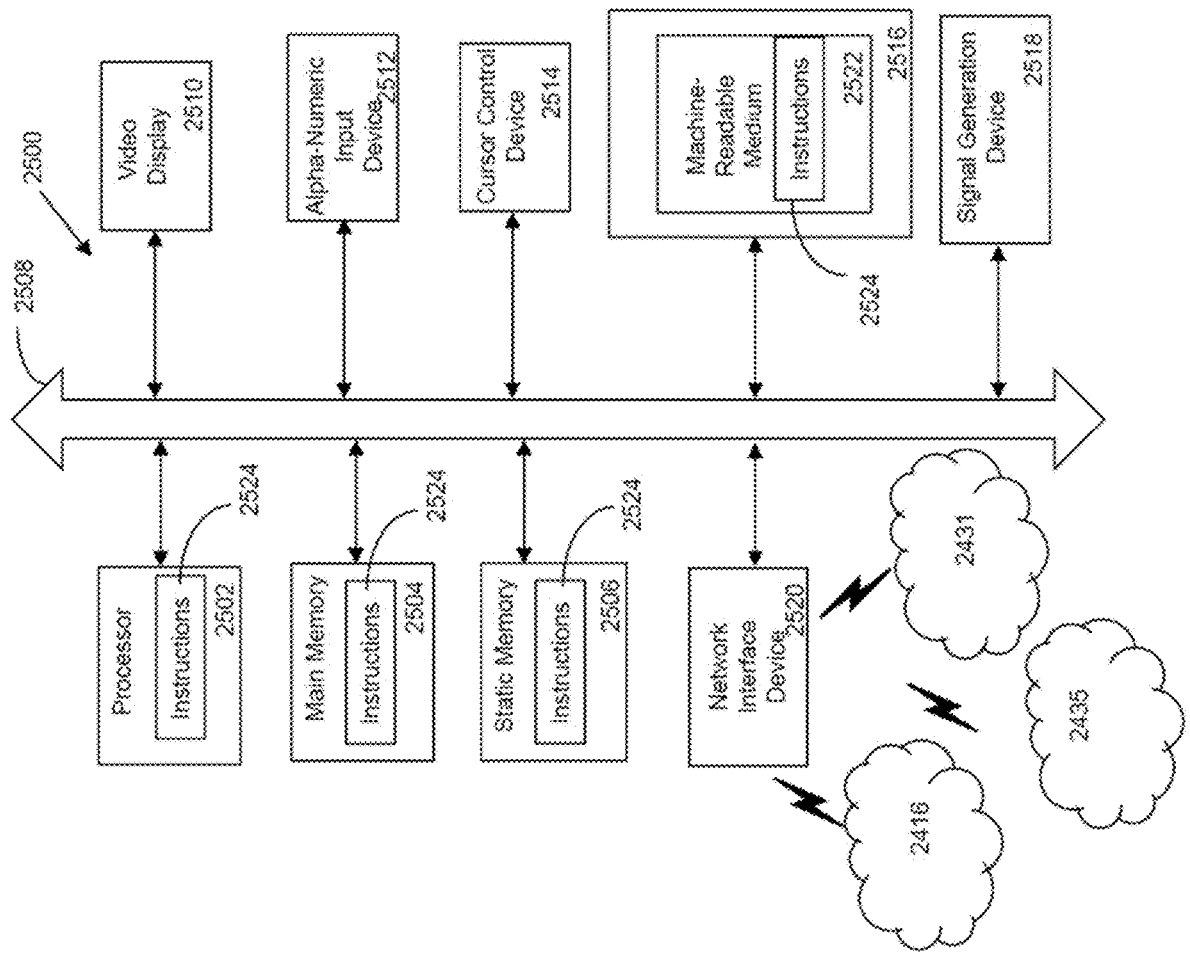
FIG. 7 is a schematic diagram of a machine in the form of a computer system which a set of instructions, when executed, may cause the machine to perform any one or more of the methodologies or operations of the systems and methods for utilizing an earphone according to embodiments of the present disclosure.

Referring now also to FIG. 7, at least a portion of the methodologies and techniques described with respect to the exemplary embodiments of the system 2400 can incorporate a machine, such as, but not limited to, computer system 2500, or other computing device within which a set of instructions, when executed, may cause the machine to perform any one or more of the methodologies or functions discussed above. The machine may be configured to facilitate various operations conducted by the system 2400. For example, the machine may be configured to, but is not limited to, assist the system 2400 by providing processing power to assist with processing loads experienced in the system 2400, by providing storage capacity for storing instructions or data traversing the system 2400, by providing functionality and/or programs for facilitating the operative functionality of the earphone devices 2415, 2430, and/or the first, second, third, fourth, and fifth user devices 2402, 2406, 2410, 2421, 2425 and/or the earphone devices 2415, 2430, by providing functionality and/or programs for facilitating operation of any of the components of the earphone devices 2415, 2430 (e.g. ear canal receivers, transceivers, ear canal microphones, ambient sound microphones, or by assisting with any other operations conducted by or within the system 2400.

In some embodiments, the machine may operate as a standalone device. In some embodiments, the machine may be connected (e.g., using communications network 2435, the communications network 2416, the communications network 2431, another network, or a combination thereof) to and assist with operations performed by other machines and systems, such as, but not limited to, the first user device 2402, the second user device 2411, the third user device 2410, the fourth user device 2421, the fifth user device 2425, the earphone device 2415, the earphone device 2430, the server 2440, the server 2450, the database 2455, the server 2460, or any combination thereof. The machine may be connected with any component in the system 2400. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 2500 may include a processor 2502 (e.g., a central processing unit (CPU), a graphics processing unit (GPU, or both), a main memory 2504 and a static memory 2506, which communicate with each other via a bus 2508. The computer system 2500 may further include a video display unit 2510, which may be, but is not limited to, a liquid crystal display (LCD), a flat panel, a solid state display, or a cathode ray tube (CRT). The computer system 2500 may include an input device 2512, such as, but not limited to, a keyboard, a cursor control device 2514, such as, but not limited to, a mouse, a disk drive unit 2516, a signal generation device 2518, such as, but not limited to, a speaker or remote control, and a network interface device 2520.

The disk drive unit 2516 may include a machine-readable medium 2522 on which is stored one or more sets of instructions 2524, such as, but not limited to, software embodying any one or more of the methodologies or functions described herein, including those methods illustrated above. The instructions 2524 may also reside, completely or at least partially, within the main memory 2504, the static memory 2506, or within the processor 2502, or a combination thereof, during execution thereof by the computer system 2500. The main memory 2504 and the processor 2502 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein can also be intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 2522 containing instructions 2524 so that a device connected to the communications network 2435, the communications network 2416, the communications network 2431, another network, or a combination thereof, can send or receive voice, video or data, and communicate over the communications network 2435, the communications network 2416, the communications network 2431, another network, or a combination thereof, using the instructions. The instructions 2524 may further be transmitted or received over the communications network 2435, another network, or a combination thereof, via the network interface device 2520.

While the machine-readable medium 2522 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

Figure 9:
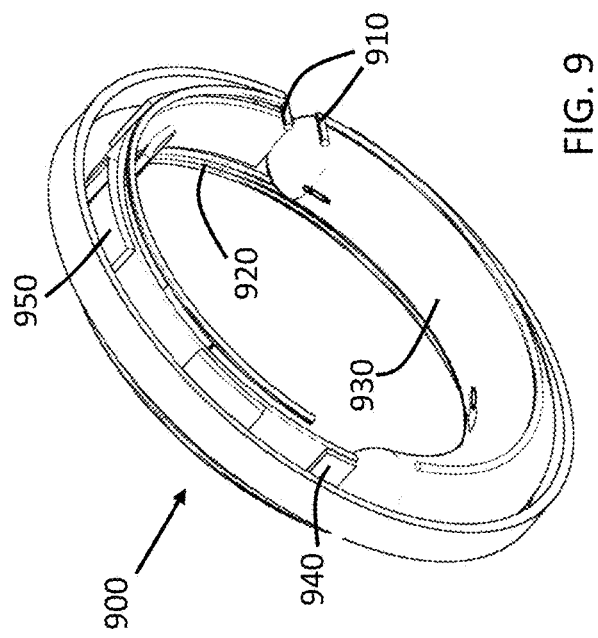
FIGS. 8, 9 and 10 illustrate an example of a ring or bracelet device configuration.
Figure 8:
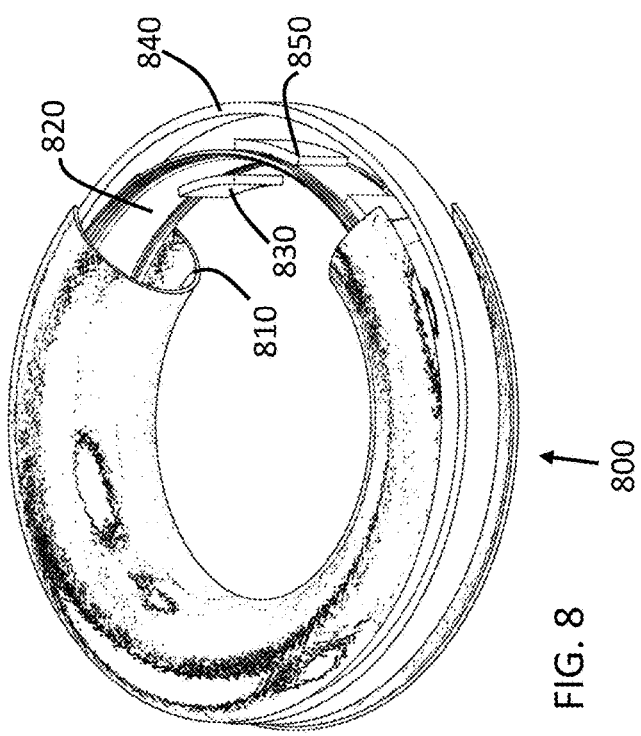
Figure 10:
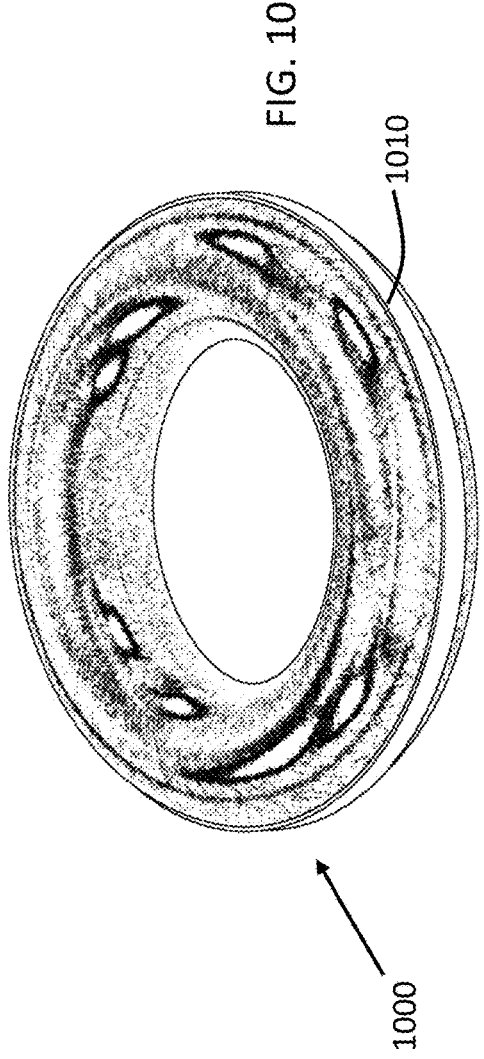

FIGS. 8, 9 and 10 illustrate an example of device 1 in a ring or bracelet configuration. FIG. 10 illustrates a ring/bracelet 1000 that includes a touch control surface 1010. The touch control surface 1010 can respond to pressure and/or electric field disruption by the close proximity of a finger. FIG. 8 shows a cut away of the outer surface 810 of the ring/bracelet 800. The interior can include a flexible or curved circuit board 820, a user interactive sensor 840 (e.g., touch sensor), biometric sensors 830, and a processor 850. FIG. 9 illustrates the outer surface or the ring/bracelet 900 totally removed exposing more of the internal electronics, which can include an antenna 910, a charging coil 920 (for contactless charging), a rechargeable battery 930, and other sensors 940 (e.g., accelerometers, environmental, microphones, speakers, LED emitter, etc. . . . ) and a transmitter 950. Data from the sensors 940 (note could only have one sensor in the ring/bracelet) can be stored in memory, not shown, and stored for later retrievable or sent via wireless connection to a second device and/or a remote server. The ring/bracelet 1000 can also communicate with other wearables, for example if the touch control surface 1010 is activated, a signal could be sent to a phone, watch, or other wearable to check if they are being held or used, so that the ring/bracelet can avoid mistaken touch commands. Upon receiving a user interface signal from the interactive sensor 840, the processor 850, evaluates the signal matching it to stored commands. Upon identification of the command, the processor 850 then enacts the commands. For example, instructions can be stored in memory associated with various operations (e.g., download data, establish a wireless link, record an audio, take a pulse measurement, take an blood oxygen measurement), and the processor can execute the instructions performing the operations associated with commands. Note that the ring/bracelet can include an RFID passive or active sensor. When queried the RFID can send back an identifier and data, acting as an automatic identification and adapt capture (AIDC). This can be used by a separate device to query the region around the separate device to see if any other devices are within the query RF. If so then the separate device processor can register those devices temporarily and query their data upon a command or event. Note that elements of the ring/bracelet can also be contained within a watch device.

FIGS. 11 and 12 illustrate an example of a footwear device configuration. FIG. 11 illustrates the top view of a shoe 1100, with front sensors 1110 embedded into the shoe. FIG. 12 shows the bottom view of a shoe 1200, having rear sensor(s) 1210 and bottom sensors 1220 and 1230. Each of the sensors 1110, 1210, 1220, and 1230 can be any type of sensor described above. Note that other types of sensors can be embedded as well. For example sensors 1110 can be microphones, sensors 1230 a force sensor, sensor 1220 a moisture sensor, and the rear sensors 1210 can be an ultrasonic sensor to detect movement from behind. Note that the device 1 can be other types of devices, such as watches, phones, glasses, etc. . . . Although details of other wearables have not been discussed with regards to components, one of ordinary skill would understand that components such as sensors can be reorganized to form watches, headbands, clothes, boots, shoes, hats, umbrellas, utensils, pencils and pens and other wearable items. The methods herein also apply to any non-wearable device that can include components of device 1 and communicate with other devices, such as book bindings, drink coasters, lamps, doors, windows, cups, plates, floors, etc. . . . For example, a store can place device 1 like items around the store for example lamps, mirrors, mats, shelves with embedded sensors that communicate information. This information can be used to identify shoplifters, or other criminal activity.

Figure 13:
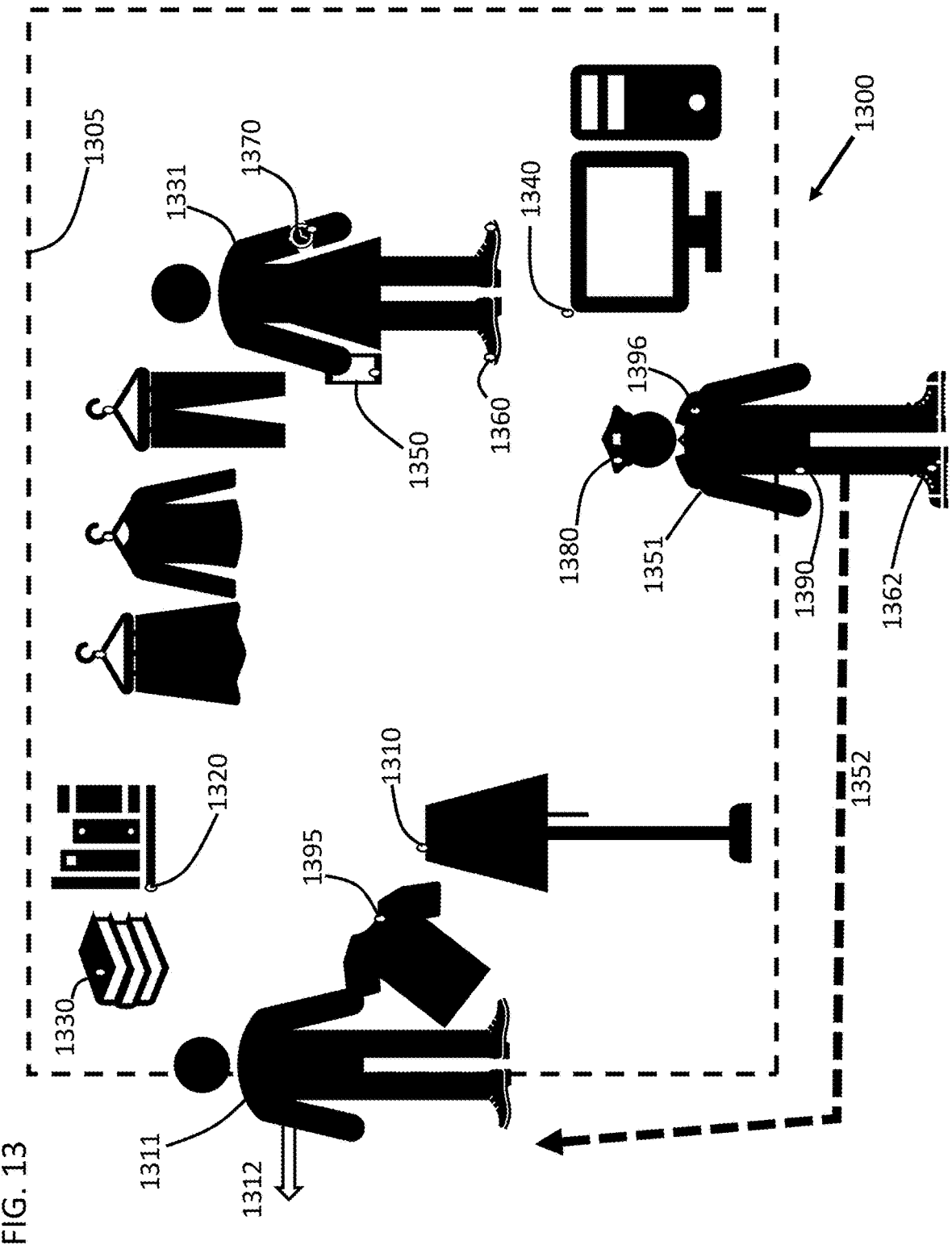
FIG. 13 illustrates a non-limiting example of the use of wearable and non-wearable devices.

FIG. 13 illustrates a store scenario 1300, having a perimeter 1305, contained within several non wearable device is placed about the store, for example, a lamp (1310), shelf (1320), book (1330), computer (1340) and several wearable device is, such as phone (1350), shoes (1360, 1362), watch (1370), hat (1380), trousers (1390), and shirt (1395, 1396). Various sensors are included with the various devices, the common theme being that they can be queried or initiate querying, and save and provide data. In the scenario shown in 1300, a perimeter 1305 has been set up such that any store wearable or non-wearable leaving the perimeter 1305 sends a signal to at least one of the other store wearable or non-wearables. A criminal 1311 seeks to leave 1312 the perimeter with a shirt 1395 that has not been paid for. The device embedded in shirt 1395, upon approaching the perimeter (e.g., within 1 m of a preset store perimeter setup) sends a signal to an other store wearable or non-wearable that has been designated to monitor the store items (e.g., computer 1340). The computer 1340, checks the shirt 1395 info to see if has been purchased. If so a signal can be sent back to the shirt 1395 that it has been paid for. If not computer 1340 can immediately notify nearby wearable and non-wearables to save buffered memory of sensor data, send the buffered data to the computer 1340 for saving, the wearables and non-wearables can purposely start recording with appropriate sensors. The store devices (e.g., 1330, 1310) can also send meta data or program to be stored on the criminal's devices, for example a virus that sends a periodic signal with location information to authorities. An alert to local authorities (e.g., security person 1380) can be sent with data obtained from the various devices. For example, the best picture (as determined by an AI in the computer), the weight (e.g., taken by a mat that the criminal walked on at the entrance of the store), height (e.g., as derived from sensor data such as ultrasonic sensors or imaging sensors), location (e.g., as relayed by the shirt 1395), along with a path 1352 to the criminal 1311. Even a fingerprint if a door handle is embedded with device sensors to monitor finger prints. The various devices can also share data, for example the shirt 1395 can send notice to the lamp 1310 which sends to the computer 1340 which sends a notice to a store clerk 1331, whom can politely remind the customer. Note that the device in shirt 1395 can also contain a damaging mode, that is activated to damage the shirt when it exceeds a distance out of the perimeter or a time. The store scenario 1300 is a non-limiting example of wearable and non-wearable devices sharing data with each other and with a controller, a selected device, to enact upon determined trigger events. The scenario could also be a fire, where embedded sensors in the devices (1320, 1330, 1370, 1350, 1360, 1310, 1340, 1395) can register elevated temperatures and when a threshold is exceeded notification is sent to a controlling device (e.g., 1340). If an acknowledgement signal is received from the controlling device, data can be sent to the controlling device to analyze the data and enact upon stored trigger event commands such as call authorities (e.g., fire department, mall security). The data can be sent to a remote server to save the data incase the controlling device becomes fire damaged. Additionally, the variation in temperatures in time as measured by the various devices can be used to determine the start point, expansion rate, and other evidence that can be used by investigators to determine the origin and likely accelerant if any. Another scenario can be if the shopping clerk 1331 has a health emergency, then devices 1370, 1350, 1360 can detect a health issue, for example the watch 1370 can detect heart rate, pressure and oxygenation. Shoes 1360 can detect a stumble, and phone 1350 can detect if it was dropped. Sudden changes from threshold values can trigger the devices into sending notification to a remote health server, notifying both remote emergency personnel, and local (e.g. mall security personnel).

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The terms and phrases used herein are not intended to be limiting but rather to provide an understandable description of the embodiments.

The terms "a" or "an", as used herein, are defied as one or more than one. The term "another", as used herein, is defined as at least a second or more. The terms "including" and/or "having" as used herein, are defined as comprising (i.e. open transition). The term "coupled" or "operatively coupled" as used herein, is defined as connected, although not necessarily directly, and not necessarily mechanically. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. Like numbers refer to like elements throughout. In the figures, the sizes of certain lines, layers, components, elements or features may be exaggerated for clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of a device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term earpiece or "earpiece module" includes any type of device that may be attached to or near the ear of a user and may have various configurations, without limitation. Such configurations include, but are not limited to, earpieces, ear buds, headphones, headsets, hearing aids, personal sound amplification products (PSAPS), and glasses.

The term "real-time" is used to describe a process of sensing, processing, or transmitting information in a time frame which is equal to or shorter than the minimum timescale at which the information is needed. For example, the real-time monitoring of pulse rate may result in a single average pulse-rate measurement every minute, averaged over 30 seconds, because an instantaneous pulse rate is often useless to the end user. Typically, averaged physiological and environmental information is more relevant than instantaneous changes. Thus, in the context of the present invention, signals may sometimes be processed over several seconds, or even minutes, in order to generate a "real-time" response.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" can include monitoring of blood gas levels, blood hydration, blood flow, and metabolite/electrolyte levels. In the embodiments herein, the term "physiological" is intended to be used broadly, covering both physical and psychological characteristics of or from the body of an organism. However, in some cases, the term "psychological" is called-out separately to emphasize aspects of physiology that are more related to brain activity and a state of being or mood rather than the activity of other organs, tissues, or cells. In this regard, multimodal monitoring can enhance the meaning or interpretation of psychological information, particularly with the analysis of voice, words, phrases and semantics in conjunction with other physiological measurements as further detailed below.

It should be understood that the embodiments herein can apply and be adapted to animals having vastly different anatomical structures than humans. For example, an earpiece attached or inserted into a cow, a dog, or a horse's ear (or other anatomical conduit) will have vastly different shapes or architectures, but can certainly be adapted to form sealed chambers or conduits sufficient to provide isolation in accordance with the embodiments. Thus, tracking or monitoring a cow's health, productivity or other parameters or a dog or a horse's speed or sentiment (during training) using some of the objective techniques herein for deciphering or understanding semantics (for humans) can equally apply to animals.

The term "health" refers generally to the quality or quantity of one or more physiological parameters with reference to an organism's functional abilities. Health can include both private and public information. In the private portion, health information is personalized for each subject that is stored. In the public portion, anonymous health is stored and is accessible by third parties. The private or public health information may also include environmental information or other data as well.

The term "ad hoc" refers generally to a wireless connection established for the duration of one session without the need for a base station. Instead, devices discover others within range to form a network. Bluetooth®, Low Energy Bluetooth, Zigbee, and Wi-Fi protocols are a few examples. The term "processor" typically refers to logic circuitry that responds to and processes basic instructions that drive a computer or other electronic devices. The term processor has generally replaced the term central processing unit (CPU) and can further refer to a microprocessor, a digital signal processor, a programmable logic device, an application specific integrated circuit or ASIC or any number of other logic devices. The processor in a personal computer or embedded in small devices is often called a microprocessor. The term "sensor" refers to a device that detects or measures a physical property and enables the recording, presentation or response to such detection or measurement using processor and optionally memory. A sensor and processor can take one form of information and convert such information into another form, typically having more usefulness than the original form. For example, a sensor may collect raw physiological or environmental data from various sensors and process this data into a meaningful assessment, such as pulse rate, blood pressure, or air quality using a processor. A "sensor" herein can also collect or harvest acoustical data for biometric analysis (by a processor) or for digital or analog voice communications. A "sensor" can include any one or more of a physiological sensor (e.g., blood pressure, heart beat, etc.), a biometric sensor (e.g., a heart signature, a fingerprint, etc.), an environmental sensor (e.g., temperature, particles, chemistry, etc.), a neurological sensor (e.g., brainwaves, EEG, etc.), or an acoustic sensor (e.g., sound pressure level, voice recognition, sound recognition, etc.) among others. A variety of microprocessors or other processors may be used herein. Although a single processor or sensor may be represented in the figures, it should be understood that the various processing and sensing functions can be performed by a number of processors and sensors operating cooperatively or a single processor and sensor arrangement that includes transceivers and numerous other functions as further described herein.

The term "clinical study" refers broadly to the application of science to health, where "health" may refer to both physical health as well as mental or psychological health. The term "clinical study" and "clinical trial" are used interchangeably herein. As an example, the interaction between a therapy and health or physiology—such as a drug therapy, exercise/diet plan, physical regime, etc.—can constitute a clinical study. As another example, the interaction between the health and the environmental exposure of individuals or groups can constitute a clinical study. In some cases a clinical study is performed by professionals in medicine or science. In other cases, a clinical study is performed by amateurs, computer programs, or individuals themselves, sometimes in the form of self help.

The term "marketing" refers to the act of bringing together buyers and sellers, and the term "marketing study" refers to the study of the needs and wants of buyers and sellers and how the buyers and sellers can come together.

The term "health study" refers to monitoring the health of an organism and studying the data regardless of the method of study.

The term "wellness" generally refers to a healthy balance of the mind-body and spirit that results in an overall feeling of well-being, and/or the state of being healthy. The term "wellness study" refers to the study of the quality of health and wellbeing. In some cases a wellness study is performed by professionals in medicine or science. In other cases, a clinical study is performed by amateurs, computer programs, or individuals themselves, sometimes in the form of self help.

The term "dieting plan" refers to a method of planning and/or regulating the intake of food or nutrients into the body. The term "exercise plan" refers to a method of planning or regulating physical activity. In many cases, a diet/exercise plan are used together to improve or reduce health. These plans can be operated by professionals, such as professional dieticians or physical trainers, or by amateurs. In some cases, these plans are regulated by computer programs or individuals themselves, sometimes in the form of self help.

The term "health study" refers to studying health as in its raw form, without necessarily being concerned about interactions between health and other factors.

The term "sickness and/or disease" refers generally to aspects of a sickness, disease, or injury in an individual or group of individuals.

The term "environmental exposure" refers to any environmental occurrence (or energy) to which an individual or group of individuals is exposed. For example, exposure to solar energy, air pollution, water pollution, temperature, nuclear radiation, humidity, particles, water, etc. which may all constitute environmental exposure. A variety of relevant environmental energies are listed elsewhere herein.

In many cases, the above cases overlap. As an example, a clinical study or wellness study may explore or record the interaction between physiological elements & environmental elements.

The term "aggregated" refers to information that is stored and/or grouped. In some cases, these groupings can be based on personal or demographical information, such as grouping based on ethnicity, sex, income, personal preferences or the like. Aggregated information, particularly in social media contexts, in addition to the personal or demographic information can also include current or recent location info, current or recent activity info, as well as current or recent biometric, physiological, or environmental information. For example, a device can enable the sharing of current location (e.g., at the Guggenheim Museum in NYC, or a pharmacy in Colorado), current or recently listened to content (whether reproduced in the ear (e.g., listening to a streaming or downloaded Andrea Bocelli album) or heard via an ambient microphone in the field (e.g., at a Cold Play concert) and recent keywords from a conversation or exchange with a third party (e.g., "I'll have a little of the red cab" or "Bartender, can I have a Sierra Nevada Pale Ale" or "Fill this prescription for Girl Scout Cookies or OG Kush for me dude"), and a current physiological measure (e.g., current heart rate or blood pressure) to create a possibly shared point of interest with another individual in a social network. As can be imagined, the results can be surprising The term "multimodal" refers to monitoring of at least two different parameters such as sound pressure level and blood pressure or heart rate. Note, the different parameters can be related types of measurements such as hear rate and blood pressure, but they can also quite different capture or harvested from acoustic, biologic, neurologic, motion, or vision sensors as examples. In some embodiments, multimodal monitoring can enhance the interpretation and analysis relating to semantics. For example, the reading of motion, brainwaves, sound pressure level, blood pressure, or heart rate along with voice recognition analysis of spoken words can provide richer contextual meaning. Assuming baseline readings exist for an individual, multimodal readings can more clearly determine if an elevated heart beat or blood pressure reading is an indication of potential sleep disorder or heart disease within the context of a typical daily activity (e.g., sleeping, walking or sitting) or within the context of a less typical daily activity (e.g., sprinting to catch a bus or rigorously exercising). Multimodal analysis or processing can enhance the logical interpretation given to words. In other words, multimodal analysis or processing can improve a semantics engine that interprets the logic and meaning in spoken words.

The terms "health and environmental network" and "health and environmental monitoring system" are used interchangeably herein. The terms "monitoring system" and "network" may be used interchangeably, as well. The term "biofeedback" relates to measuring a subject's bodily processes such as blood pressure, heart rate, skin temperature, galvanic skin response (sweating), muscle tension, etc., and conveying such information to the subject in real-time in order to raise the subject's awareness and conscious control of the related physiological activities. Herein, biofeedback is synonymous with personal physiological monitoring, where biochemical processes and environmental occurrences may be integrated into information for one or more individuals. For example, monitoring hormone levels and air quality through the innovative sensor network described herein for the purpose of tracking, predicting, and/or controlling ovulation is also considered biofeedback. Biofeedback is also considered a technique used to learn to control bodily functions, such as heart rate. With biofeedback, the user can be connected to electrical sensors that help the user receive information (feedback) about their body (bio). This feedback helps the user focus on making subtle changes in their body, such as relaxing certain muscles, to achieve the desired results, such as reducing pain. In essence, biofeedback gives the user the power to use their thoughts to control their body, often to help with a health condition or physical performance. Biofeedback is often used as a relaxation technique.

The term "profile" relates to a summary of noteworthy characteristics and/or habits of an individual or group of individuals. These characteristics may be physiological (health-related), environmental, statistical, demographical, behavioral, and the like. Age, location, gender, sex, weight, ethnicity, and/or height may be included in a profile. The profile and the aforementioned characteristics and/or habits can be used in the context of social media and further information in the interactions within a social media network can be extracted to form a part of a profile as well Additionally, a profile may reference the buying and/or spending habits of an individual or group and can further include a credit rating. Profiles may be utilized in making predictions about an individual or group.

The term "support," when used as a verb, means to assist and/or provide at least one method or outcome for something. For example, a method of supporting a therapy for something may refer to a method of assisting a therapeutic technique. In some cases, supporting a therapy may involve providing an entirely new method having a therapeutic outcome. As a more specific example, a noninvasive health and environmental monitor system/network may support a therapeutic drug study by noninvasively monitoring the real-time drug dosage in the body through multiwavelength pulse oximetry, monitoring core body temperature through thermal sensing of the tympanic membrane, and monitoring environments which may positively or negatively affect the quality of the drug therapy.

What is claimed is:

1. A system of monitoring an environment comprising:
a first wearable device comprising:
   a first microphone configured to generate a first microphone signal;
   a user interface;
   a memory configured to store instructions:
   a first biometric sensor; and
   a processor, wherein the processor executes the instructions to perform operations, the operations comprising:
      locating at least two linkable devices, wherein a first linkable device is a second wearable device that includes a second microphone and second linkable device is a first non-wearable device that includes a first sensor, wherein the first sensor is at least one of speaker or a second biometric sensor or an environmental sensor or a combination thereof;
      linking the at least two linkable devices with the first wearable device, wherein the at least two linkable devices can link with the first wearable device so that the first wearable device can receive data from the at least two linkable devices, and wherein the first wearable device can control at least one of the at least two linkable devices;
      receiving a first data from the second wearable device;
      sending a request to the first non-wearable device to send a second data to the processor;
      receiving the second data;
      presenting the first data and the second data to a user of the first wearable device;
      receiving a control command from the user using the user interface; and
      sending the control command to the first non-wearable device, wherein the control command alters the function of the first non-wearable device.

2. The system according to claim 1, wherein the first wearable device is a phone, a watch, a tablet or a laptop computer.

3. The system according to claim 2, wherein the second wearable device is at least one of a phone, an earphone, a ring, a bracelet, a watch, a shoe, a shirt, or a hat or a combination thereof.

4. The system according to claim 3, wherein the first non-wearable device is at least one of a computer, a book, a lamp, a TV, fixed sensors, a communication hub, or a mat.

5. The system according to claim 4, wherein the first biometric sensor measures at least one of a the temperature of a user, heart rate, blood pressure, a fingerprint, or a blood oxygenation level or a combination thereof.

6. The system according to claim 1, wherein the environmental sensor measures at least one of sound, temperature, pressure, or moisture or a combination thereof.

7. The system according to claim 1, wherein the first microphone measures an ambient sound environment about the first wearable device.

8. The system according to claim 7, wherein the operations further include:
analyzing a sound signal for a voice and if a voice is present analyzing the sound signal for a keyword, wherein the sound signal is the first microphone signal or a modified first microphone signal.

9. The system according to claim 8, wherein the second wearable device includes a second biometric sensor configured to generate second biometric data and wherein the operations further include:
sending the second biometric data to a remote server.

10. The system according to claim 8, wherein the first non-wearable device includes a second environmental sensor configured to generate second environmental data and wherein the operations further include:
sending the second environmental data to the remote server.

11. The system according to claim 8, wherein the operations further include:
sending the first microphone signal to a remote server.

12. The system according to claim 1, wherein the operations further include:
analyzing the first microphone signal or first data or second data or a combination thereof to detect a trigger event, wherein the trigger event is a fire or an intruder.

13. The system according to claim 8, wherein the modified first microphone signal is generated by applying at least one filter to the first microphone signal.

14. The system according to claim 8, wherein the modified first microphone signal is generated by applying at least one gain to the first microphone signal.

* * * * *